United States Patent
Wilson et al.

(10) Patent No.: US 9,303,262 B2
(45) Date of Patent: Apr. 5, 2016

(54) METHODS FOR IDENTIFYING APTAMER REGULATORS

(75) Inventors: Charles Wilson, Concord, MA (US); David Epstein, Belmont, MA (US); John L. Diener, Cambridge, MA (US)

(73) Assignee: ARCHEMIX LLC, San Francisco, CA (US)

( * ) Notice: Subject to any disclaimer, the term of this patent is extended or adjusted under 35 U.S.C. 154(b) by 1555 days.

(21) Appl. No.: 10/664,610

(22) Filed: Sep. 16, 2003

(65) Prior Publication Data

US 2004/0137010 A1    Jul. 15, 2004

Related U.S. Application Data

(60) Provisional application No. 60/411,414, filed on Sep. 17, 2002, provisional application No. 60/461,966, filed on Apr. 10, 2003, provisional application No. 60/490,237, filed on Jul. 25, 2003.

(51) Int. Cl.
  *A61K 39/21*  (2006.01)
  *C07K 14/16*  (2006.01)
  *C12N 15/115* (2010.01)
  *C07K 16/10*  (2006.01)

(52) U.S. Cl.
  CPC .......... *C12N 15/115* (2013.01); *C07K 16/1063* (2013.01); *C12N 2310/317* (2013.01); *C12N 2310/321* (2013.01); *C12N 2310/322* (2013.01); *C12N 2310/3513* (2013.01)

(58) Field of Classification Search
  USPC ...................................... 435/6, 455; 536/23.1
  See application file for complete search history.

(56) References Cited

U.S. PATENT DOCUMENTS

| | | |
|---|---|---|
| 4,683,195 A | 7/1987 | Mullis |
| 4,801,530 A | 1/1989 | Nogueira et al. |
| 4,894,325 A | 1/1990 | Engelhardt et al. |
| 4,935,363 A | 6/1990 | Brown et al. |
| 4,959,309 A | 9/1990 | Dattagupta et al. |
| 5,070,010 A | 12/1991 | Hsu |
| 5,118,801 A | 6/1992 | Lizardi et al. |
| 5,270,163 A | 12/1993 | Gold et al. |
| 5,338,671 A | 8/1994 | Scalice et al. |
| 5,459,015 A | 10/1995 | Janjic et al. |
| 5,496,938 A | 3/1996 | Gold et al. |
| 5,503,978 A | 4/1996 | Schneider et al. |
| 5,567,588 A | 10/1996 | Gold et al. |
| 5,580,737 A | 12/1996 | Polisky et al. |
| 5,635,615 A | 6/1997 | Allen et al. |
| 5,637,459 A | 6/1997 | Burke et al. |
| 5,648,214 A | 7/1997 | Nieuwlandt et al. |
| 5,654,151 A | 8/1997 | Allen et al. |
| 5,660,985 A | 8/1997 | Pieken et al. |
| 5,683,867 A | 11/1997 | Biesecker et al. |
| 5,691,145 A | 11/1997 | Pitner et al. |
| 5,705,337 A | 1/1998 | Gold et al. |
| 5,707,796 A | 1/1998 | Gold et al. |
| 5,723,323 A | 3/1998 | Kauffman et al. |
| 5,756,291 A * | 5/1998 | Griffin et al. ...................... 435/6 |
| 5,756,710 A | 5/1998 | Stein et al. ................... 536/24.5 |
| 5,763,173 A | 6/1998 | Gold et al. |
| 5,763,177 A | 6/1998 | Gold et al. |
| 5,789,157 A | 8/1998 | Jensen et al. |
| 5,859,223 A | 1/1999 | Janjic et al. |
| 5,861,254 A | 1/1999 | Schneider et al. |
| 5,958,691 A | 9/1999 | Pieken et al. |
| 5,989,823 A | 11/1999 | Jayasena |
| 6,011,020 A | 1/2000 | Gold et al. |
| 6,013,443 A | 1/2000 | Heilig et al. |
| 6,020,130 A | 2/2000 | Gold et al. |
| 6,051,698 A | 4/2000 | Janjic et al. |
| 6,287,765 B1 * | 9/2001 | Cubicciotti ....................... 435/6 |
| 2002/0127581 A1 | 9/2002 | Rajendran et al. ................. 435/6 |
| 2003/0064931 A1 * | 4/2003 | Gallivan ......................... 514/12 |
| 2003/0083294 A1 * | 5/2003 | Sullenger et al. ............... 514/44 |

FOREIGN PATENT DOCUMENTS

| | | |
|---|---|---|
| EP | 0592035 | 4/1994 |
| EP | 1 219 708 A1 | 7/2002 |
| GB | 2 183 661 A | 6/1987 |
| WO | WO89/06694 | 7/1989 |
| WO | WO91/14436 | 10/1991 |
| WO | WO 91/19813 | 12/1991 |
| WO | WO92/05285 | 4/1992 |
| WO | WO92/07065 | 4/1992 |
| WO | WO92/14842 | 9/1992 |
| WO | WO92/14843 | 9/1992 |
| WO | WO 96/40717 | 12/1996 |
| WO | WO98/18480 | 5/1998 |
| WO | WO99/31276 | 6/1999 |
| WO | WO 01/09158 a1 | 2/2001 |

OTHER PUBLICATIONS

Firer et al. Efficient elution of functional proteins in affinity chromatography. Journal of Biochemical and Biophysical Methods, Oct. 30, 2001, vol. 49, Issues 1-3, pp. 433-442.*
International Search Report for PCT/US03/29798, mailing date: Apr. 26, 2004.
Araki et al., (1998) "Allosteric regulation of a ribozyme activity through ligand-induced conformational change", *Nucl. Acids Res.*, 26(14):3379-3384.
Sayer et al., (2002) "Structural characterization of a 2'F-RNA aptamer that binds a HIV-1 SU glycoprotein, gp120", *Biochem. Biophys. Res. Commun.*, 293:924-931.
Supplementary Partial European Search Report for EP 03 75 2557, mailed Feb. 15, 2006.
Andrake (1988) "DNA polymerase of bacteriophage T4 is an autogenous translational repressor", *Proc. Natl. Acad. Sci. USA* 85:7942-7946.

(Continued)

*Primary Examiner* — Shanon A Foley
*Assistant Examiner* — Myron Hill
(74) *Attorney, Agent, or Firm* — Cooley LLP; Ivor Elrifi

(57) ABSTRACT

Methods are provided for identifying aptamer regulators. Aptamer regulators are aptamers that bind to a target wherein binding of the aptamer regulator to the target increases the binding affinity of the target for a target partner relative to the affinity of the target for the target partner when the target is not bound by the aptamer regulator such that binding of the aptamer regulator to the target is a prerequisite for target-target partner complex formation.

8 Claims, 12 Drawing Sheets

(56) References Cited

OTHER PUBLICATIONS

Barnett et al., (2001) "The ability of an oligomeric human immunodeficiency virus type 1 (HIV-1) envelope antigen to elicit neutralizing antibodies against primary HIV-1 isolates is improved following partial deletion of the second hypervariable region", J. Virol. 75:5526-5540.
Belshe et al., (1994) "HIV infection in vaccinated volunteers", JAMA. 272: 431.
Burton (1997) "A vaccine for HIV type 1: the anibody perspective", Proc Natl Acad Sci U S A. 94: 10018-10023.
Carey et al., (1983) "Sequence-specific interaction of R17 coat protein with its ribonucleic acid binding site", Biochem. 22(11):2601-2610.
Chen et al. (1994) "Selection of high-affinity RNA ligands to reverse transcriptase: inhibition of cDNA synthesis and Rnase H activity", Biochem. 33:8746-8756.
Cohen et al. (1969) "Interactions of hormonal steroids with nucleic acids: a specific requirement for guanine", Proc. Natl. Acad. Sci. USA 63:458-464.
Cohen J. (1994) "U.S. panel votes to delay real-world vaccine trials", Science 264: 1839.
Conrad et al., (1996) "In vitro selection of nucleic acid aptamers that bind proteins"; Meth. Enzymol. 267: 336-367.
Cormier et al., (2000) "Specific interaction of CCR5 amino-terminal domain peptides containing sulfotyrosines with HIV-1 envelope glycoprotein gp120", PNAS 97: 5762-5767.
Cummins et al., (1995) "Characterization of fully 2'-modified oiigoribonucleotide hetero- and homoduplex hybridization and nuclease sensitivity", Nucl. Acids Res. 23: 2019-2024.
Davis et al. (1996) "Identifying consensus patterns and secondary structure in SELEX sequence sets", Meth. Enzymol. 267(18): 302-314.
Dehouck et al., (1996) "Blood-brain barrier in vitro—rapid evaluation of strategies for achieving drug targeting to the central nervous system", Biol. Physiol. Blood Brain Barrier, Couraud and Scherman eds., Chapter 23, pp. 143-146.
Doranz et al., (1999) "Use of a gp120 binding assay to dissect the requirements and kinetics of human immunodeficiency virus fusion events", J. Virol. 73: 10346-10358.
Dougan et al., (2000) "Extending the lifetime of anticoagulant oligodeoxynucleotide aptamers in blood", Nucl. Med. Biol. 27: 289-297.
Ellington & Szostak (1990) Abstracts of papers presented at the 1990 meeting on RNA Processing, Cold Spring Harbor Laboratory, Cold Spring Harbor, NY, p. 84.
Emini et al., (1992) "Prevention of HIV-1 infection in chimpanzees by gp120 V3 domain-specific monoclonal antibody", Nature 355: 728-730.
Evans et al., (2001) "QS-21 promotes an adjuvant effect allowing for reduced antigen dose during HIV-1 envelope subunit immunization in humans", Vaccine 19: 2080-2091.
Fitzwater et al., (1996) "A SELEX primer", Meth. Enzymol. 267:275-301.
Fouts et al., (2002) "Crosslinked HIV-1 envelope-CD4 receptor complexes elicit broadly cross-reactive neutralizing antibodies in rhesus macaques", PNAS 99:11842-11847.
Gaschen et al., (2002) "Diversity considerations in HIV-1 vaccine selection", Science 296:2354-2360.
Gath et al., (1996) "The blood-CSF barrier in vitro", Biol. Physiol. Blood Brain Barrier, Couraud and Scherman eds., Chapter 25, pp. 153-158.
Graham BS. (2002) "Clinical Trials of HIV vaccines", Annu. Rev. Med. 53: 207-221.
Green et al., (1995) "Nuclease-resistant nucleic acid ligands to vascular permeability factor/vascular endothelial growth factor", Chem. Biol. 2:683-695.
Jellinek et al., (1994) "Inhibition of receptor binding by high-affinity RNA ligands to vascular endothelial growth factor", Biochem. 33:10450-10456.
Jellinek et al., (1995) "Potent 2'-amino-2'deoxypyrimidine RNA inhibitors of basic fibroblast growth factor", Biochem. 34(36):11363-11372.
Joyce & Inoue (1989) "A novel technique for the rapid preparation of mutant RNAs", Nucl. Acids Res. 17:711-722.
Joyce (1989) "Amplification, mutation and seletion of catalytic RNA", Gene 82:83-87.
Kacian et al. (1972) "A replicating RNA molecule suitable for a detailed analysis of extracellular evolution and replication", Proc. Natl. Acad. Sci. USA 69:3038-3042.
Kadonaga et al. (1986) "Affinity purification of sequence-specific DNA binding proteins", Proc. Natl. Acad. Sci. USA 83:5889-5893.
Kahn et al., (1994) "Clinical and immunologic responses to human immunodeficiency virus (HIV) type $1_{sF2}$ gp120 submit vaccine combined with MF59 adjuvant with or without muramyl tripeptide dipalmitoyl phosphatidylethanolamine in non-HIV-infected human volunteers", J. Infect. Dis. 170: 1288-1291.
Kalams et al., (2000) HIV Vaccines 2000: Prospects and Challenges. In "The Human Immunodeficiency Virus", Princeton University Press, Prineton, N.J. pp. 481-509.
Kellogg et al., (1994) "Taqstart antibody™: 'hot start' PCR facilitated by a neutralizing monoclonal antibody directed against taq DNA polymerase" BioTechniques 16:1134-1137.
Kinzler & Vogelstein (1989) "Whole genome PCR: application to the identification of sequences bound by gene regulatory proteins", Nucl. Acids Res. 17:3645-3653.
Kinzler et al. (1990) "The GLI gene encodes a nuclear protein which binds specific sequences in the human genome", Mol. Cell. Biol. 10:634-642.
Kowalski et al., (1987) "Functional regions of the envelope glycoprotein of human immunodeficiency virus type 1", Science 237: 1351-1355.
Kramer et al. (1974) "Evolution in vitro: sequence and phenotype of a mutant RNA resistant to ethidium bromide", J. Mol. Biol. 89:719-736.
Kraus et al., (1998) "Cutting edge: novel RNA ligands able to bind CD4 antigen and inhibit $CD4^+$ T lymphocyte function"; J. Immunol. 160:5209-5212.
Kwong et al., (1998) "Structure of an HIV gp120 envelope glycoprotein in complex with the CD4 receptor and a neutralizing human antibody", Nature 393:648-659.
Kwong et al., (2002) "HIV-1 evades antibody-medicated neutralization through conformational masking of receptor-binding sites", Nature 420:678-682.
Langlois et al., (1998) "Neutralizing antibodies in sera from macaques immunized with attenuated simian immunodeficiency virus", J. Virol. 72:6950-6955.
Leonard et al., (1990) "Assignment of intrachain disulfide bonds and characterization of potential glycosylation sited of the type 1 recombinant human immunodeficiency virus envelope glycoprotein (gp120) expressed in chinese hamster ovary cells" J. Biol. Chem. 265: 10373-10382.
Lestienne et al. (1983) "Inhibition of human leucocyte elastase by polynucleotides" Biochimie 65:49-52.
Levisohn & Spiegelman (1968) "The cloning of a self-replicating RNA molecule", PNAS USA 60:866-872.
Levisohn & Spiegelman (1969) "Further extracellular Darwinian experiments with replicating RNA molecules: diverse variants isolated under different selective conditions", PNAS USA 63:805-811.
Lu et al., (1995) "A trimeric structural domain of the HIV-1 transmembrane glycoprotein", Nat. Struct. Biol. 2:1075-1082.
Ma and Ptashne (1987) "A new class of yeast transcriptional activators", Cell 51:113-119.
Maniatis (1982) Molecular Cloning: a Laboratory Manual, Cold Spring Harbor, NY p. 118.
Maniatis et al. (1987) "Regulation of inducible and tissue-specific gene expression", Science 236:1237-1245.
Martin et al., (2003) "Rational design of a CD4 mimic that ibhibits HIV-1 entry and expose cryptic neutralization Epitopes", Nat. Biotechnol. 21:71-76.

(56) References Cited

OTHER PUBLICATIONS

Mascola et al., (1996) "Immunization with envelope subunit vaccine products elicits neutralizing antibodies against laboratory-adapted but not primary isolates of human immunodeficiency virus type 1", J. Infect. Dis. 173:340-348.

McGaughey et al., (2003) "HIV-1 vaccine development: constrained peptide immunogens show improved binding to the anti-HIV-1 gp41 MAb", Biochemistry 42:3214-3223.

Miele et al., (1983) "Autocatalytic replication of a recombinant RNA", J. Mol. Biol. 171:281-295.

Mills et al., (1967) "An extracellular darwinian experiment with a self-duplicating nucleic acid molecule", Proc. Natl. Acad. Sci. USA 58:217-220.

Mills et al., (1973) "Complete nucleotide sequence of a replicating RNA molecule", Science 180:916-927.

Min et al., (1988) "Search for the optimal sequence of the ribosome binding site by random oligonucleotide-directed mutagenesis", Nucl. Acids Res. 16:5075-5088.

Moore et al., (1988) "Sensitive ELISA for the gp120 and gp160 surface glycoproteins of HIV-1", AIDS Res. Hum. Retroviruses 4(5):369-379.

Moulard et al., (2002) "Broadly cross-reactive HIV-1-nutralizing human monoclonal fab selected for binding to gp120-CD4-CCR5 complexes", Proc. Natl. Acad. Sci. U S A 99:6913-6918.

Muesing et al. (1985) "Nucleic acid structure and expression of the human AIDS/lymphadenopathy retrovirus", Nature 313:450-458.

Nixon et al., (1999) "Molecular tracking of an human immunodeficiency virus nef specific Cytotoxic t-cell clone shows persistence of clone-specific t-cell receptor DNA but not mRNA following early combination antiretroviral therapy", Immunol. Lett. 66(1-3):219-228.

Oliphant & Struhl (1987) "The use of random-sequence oligonucleotides for determining consensus sequences", Meth. Enzymol. 155:568-582.

Oliphant & Struhl (1988) "Defining the consensus sequences of *E. coli* promoter elements by random selection", Nucl. Acids Res. 16:7673-7683.

Oliphant et al. (1986) "Cloning of random-sequence oligodeoxynucleotides", Gene 44:177-183.

Oliphant et al. (1989) "Defining the sequence specificity of DNA-binding proteins by selecting binding sites from random-sequence oligonucleotides: analysis of yeast GCN4 protein", Mol. Cell. Biol. 9:2944-2949.

Orgel (1979) "Selection in vitro", Proc. R. Soc. Lon. B 205:435-442.

Ou et al. (1988) "DNA amplification for direct detection of HIV-1 in DNA of peripheral blood mononuclear cells", Science 239:295-297.

Pieken et al., (1991) "Kinetic characterization of ribonuclease-resistant 2 prime—modified hammerhead ribozymes", Science 253:314-317.

Poignard et al., (2001) "GP120: biologic aspects of structural features", Annu. Rev. Immunol. 19:253-274.

Prince et al., (1991) "Prevention of HIV infection by passive immunization with HIV immunoglobulin", AIDS Res. Hum. Retroviruses 7:971-973.

Profy et al., (1990) "Epitopes recovnized by the neutralizing antibodies of an HIV-1-infected individual", J. Immunol. 144:4641-4647.

Putkonen et al., (1991) "Prevention of HIV-2 and $SIV_{sm}$ infection by passive immunization in cynomolgus monkeys", Nature 352:436-438.

Richman et al., (2003) "Rapid evolution of the neutralizing anibody response to HIV type 1 infection", PNAS 100:4144-4149.

Rizzuto et al., (1998) "A conserved HIV gp120 glycoprotein structure involved in chemokine receptor binding", Science 280:1949-1953.

Robertson & Joyce (1990) "Selection in vitro of an RNA enzyme that specifically cleaves single-stranded DNA", Nature 344:467-468.

Romaniuk et al. (1987) "RNA binding site of R17 coat protein", Biochem. 26(6):1563-1568.

Ruckman et al., (1998) "2'-fluoropyrimidine RNA-based aptamers to the 165-amino acid form of vascular endothelial growth factor ($VEGF_{165}$", J. Biol. Chem. 273:20556-20567.

Saffhill et al. (1970) "In vitro selection of bacteriophage Qβ ribonucleic acid variants resistant to ethidium bromide", J. Mol. Biol. 51:531-539.

Sambrook et al. (1989) Molecular Cloning: A Laboratory Manual, Cold Spring Harbor, NY, Section 8.9-8.10.

Sattentau et al., (1991) "Conformational changes induced in the human immunodeficiency virus envelope glycoprotein by soluble CD4 binding", J. Exp. Med. 174:407-415.

Sattentau et al., (1993) "Conformational changes induced in the envelope clycoproteins of the human and simian immunodeficiency viruses by soluble receptor binding", J. Virol. 67:7383-7393.

Singleton et al., Dictionary of Microbiol. & Molec. Biol., Wiley & Sons, New York, NY, 2nd ed. p. 493.

Sood et al., (1977) "A rapid and convenient synthesis of polythymidylic acid by the modified triester approach", Nucl. Acids Res. 4(8):2757-2765.

Soukup and Breaker (1999) "Design of allosteric hammerhead ribozymes activated by ligand-induced structure stabilization", Structure 7(8):783-791.

Sproat et al., (1991) "New synthetic routes to synthons suitable for 2'-O-allyloligoribonucleaotide assembly", Nucl. Acids Res. 19(4):733-738.

Starcich et al., (1986) "Identification and characterization of conserved and variable regions in the envelope gene of HTLV-III/LAV, the retrovirus of AIDS", Cell 45:637-648.

Sullivan et al., (1998) "Determinants of human immunodeficiency virus type 1 envelope glycoprotein activation by soluble CD4 and monoclonal antibodies", J. Virol. 72:6332-6338.

Szostak, Structure and Activity of Ribozymes, Redesigning the Molecules of Life, (SA Benner ed.) Springer-Verlag Berline Heidelberg, pp. 87-113 (1988).

Tanchou et al. (1994) "Monoclonal antibody-mediated inhibition of RNA binding and annealing activities of HIV type 1 nucleocapsid protein", AIDS Research and Human Retroviruses 10:983-993.

Thali et al., (1993) "Characterization of conserved human immunodeficiency virus type 1 gp120 neutralization Epitopes exposed upon gp120-CD4 binding", J. Virol. 67:3978-3988.

Thiesen & Bach (1990) "Target detection assay (TDA): a versatile procedure to determine DNA binding sites as demonstrated on SP1 protein", Nucl. Acids Res. 18:3203-3209.

Trkola et al., (1996) "CD4-dependent, antibody-sensitive interactions between HIV-1 and its co-receptor CCR-5", Nature 384:184-187.

Trkola et al., (1996) "Human monoclonal antibody 2G12 defines a distinctive neutralization epitope on the gp120 glycoprotein of human immunodeficiency virus type 1", J. Virol. 70:1100-1108.

Tucker et al., (1999) "Detection and plasma pharmacokinetics of an anti-vascular endothelial growth factor oligonucleotide-aptamer (NX1838) in rhesus monkeys", J. Chromatography B. 732:203-212.

Tuerck and Gold (1990) "Systematic evolution of ligands by exponential enrichment: RNA ligands to bacteriophage T4 DNA polymerase", Science 249(4968):505-510.

Tyagi et al., (1996) "Molecular beacons: probes that fluoresce upon hybridization", Nat. Biotechnol. 14:303-308.

Uhlenbeck et al. (1983) "Interaction of R17 coat protein with its RNA binding site for translational repression", J. Biomol. Struct. Dynamics 1:539-552.

Watanabe M. (2003) "Skeptical scientists skewer vaxgen statistics", Nat. Med. 9: 376.

Watson et al ., (1987) Mol. Biol. Gene, Benjamin/Cummings Publishing Co., Inc. California, pp. 267,295,323,361,394,396,397 and 405.

Wei et al., (2003) "Antibody neutralization and escape by HIV-1", Nature 422:307-312.

Wu et al., (1996) "CD4-induced interaction of primary HIV-1 gp120 glycoproteins with the chemokine receptor CCR-5", Nature 384:179-183.

Wu et al., (1997) "CCR5 levels and expression pattern correlate with infectability by macrophage-topic HIV-1, in vitro", J. Exp. Med. 185:1681-1691.

(56) References Cited

OTHER PUBLICATIONS

Yamamoto and Kumar (2000) "Molecular beacon aptamer fluoresces in the presence of tat protein of HIV-1", Genes to Cells 5:389-396.

Zhang et al., (1999) "Conformational changes of gp120 in Epitopes near the CCR5 binding site are induced by CD4 and a CD4 miniprotein mimetic", Biochemistry. 38:9405-9416.

Zhang et al., (2001) "Antibody 17b binding at the coreceptor site weakens the kinetics of the interaction of envelope gloprotein gp120 with CD4", Biochemistry. 40:1662-1670.

Geiger et al., "RNA aptamers that bind L-arginine with sub-micromolar dissociation constants and high enantioselectivity", *Nucl. Acids Res.* 24(6): 1029-1036 (1996).

US 5,756,703, 05/1998, Stein et al. (withdrawn)

* cited by examiner

Figure 11

Isolate clones, assay for binding

Sequence clones
GGGAGACAAGAAUAAACGCUCAAUUAUCAACCUUCGACAGGAGGCUCACAACAGGC
(SEQ ID NO: 227)

Truncation analysis
to define 5'- and 3'-ends
AUAAACGCUCAACCGAAGCGCGACGACUAGACGUCAAUUUAU (SEQ ID NO: 228)

Define structure by synthesis of variants or *in vitro* phylogenetic methods (SEQ ID NO: 226)

Chemically synthesize diverse pool based on aptamer structure
GGACACAUACUCUACA-N20-gggauaaacgcucaaccgaagcgcgacgacuagacgucaauuuaucaaccuucga-N20-UUAACCCAGCACGCCUCGUA
(SEQ ID NO: 230)

A,C,G,U: specified nucleotide (U→T for DNA synthesis)
N: equal proportions of A,C,G,U
a,c,g,u: 85% specified nucleotide, 5% of each other nucleotide Append random sequence tags to existing aptamers by PCR or ligation

Figure 12

METHODS FOR IDENTIFYING APTAMER REGULATORS

REFERENCE TO RELATED APPLICATIONS

This application is related to and claims priority to U.S. Provisional Patent Application Ser. No. 60/411,414 filed Sep. 17, 2002, U.S. Provisional Patent Application Ser. No. 60/461,966 filed Apr. 10, 2003, and U.S. Provisional Patent Application Ser. No. 60/490,237 filed Jul. 25, 2003, each of which is herein incorporated by reference in its entirety.

FIELD OF THE INVENTION

The invention relates generally to the field of nucleic acids and more particularly to compositions and methods for treating or preventing HIV with aptamers or aptamer compositions that specifically bind to gp120.

BACKGROUND OF THE INVENTION

Aptamers are nucleic acid molecules having specific binding affinity to molecules through interactions other than classic Watson-Crick base pairing.

Aptamers, like peptides generated by phage display or monoclonal antibodies (MAbs), are capable of specifically binding to selected targets and, through binding, block their targets' ability to function. Created by an in vitro selection process from pools of random sequence oligonucleotides (FIG. 1), aptamers have been generated for over 100 proteins including growth factors, transcription factors, enzymes, immunoglobulins, and receptors. A typical aptamer is 10-15 kDa in size (30-45 nucleotides), binds its target with sub-nanomolar affinity, and discriminates against closely related targets (e.g., will typically not bind other proteins from the same gene family). A series of structural studies have shown that aptamers are capable of using the same types of binding interactions (hydrogen bonding, electrostatic complementarity, hydrophobic contacts, steric exclusion, etc.) that drive affinity and specificity in antibody-antigen complexes.

Aptamers have a number of desirable characteristics for use as therapeutics including high specificity and affinity, biological efficacy, and excellent pharmacokinetic properties. In addition, they offer specific competitive advantages over antibodies and other protein biologics, for example:

1) Speed and control. Aptamers are produced by an entirely in vitro process, allowing for the rapid generation of initial therapeutic leads. In vitro selection allows the specificity and affinity of the aptamer to be tightly controlled and allows the generation of leads against both toxic and non-immunogenic targets.

2) Toxicity and Immunogenicity. Aptamers as a class have demonstrated little or no toxicity or immunogenicity. In chronic dosing of rats or woodchucks with high levels of aptamer (10 mg/kg daily for 90 days), no toxicity is observed by any clinical, cellular, or biochemical measure. Whereas the efficacy of many monoclonal antibodies can be severely limited by immune response to antibodies themselves, it is extremely difficult to elicit antibodies to aptamers (most likely because aptamers cannot be presented by T-cells via the MHC and the immune response is generally trained not to recognize nucleic acid fragments).

3) Administration. Whereas all currently approved antibody therapeutics are administered by intravenous infusion (typically over 2-4 hours), aptamers can be administered by subcutaneous injection. This difference is primarily due to the comparatively low solubility and thus large volumes are necessary for most therapeutic MAbs. With good solubility (>150 mg/ml) and comparatively low molecular weight (aptamer: 10-50 KD; antibody: 150 KD), a weekly dose of aptamer may be delivered by injection in a volume of less than 0.5 ml. Aptamer bioavailability via subcutaneous administration is >80% in monkey studies (Tucker, 1999). In addition, the small size of aptamers allows them to penetrate into areas of conformational constrictions that do not allow for antibodies or antibody fragments to penetrate, presenting yet another advantage of aptamer-based therapeutics or prophylaxis.

4) Scalability and cost. Therapeutic aptamers are chemically synthesized and consequently can be readily scaled as needed to meet production demand. Whereas difficulties in scaling production are currently limiting the availability of some biologics and the capital cost of a large-scale protein production plant is enormous, a single large-scale synthesizer can produce upwards of 100 kg oligonucleotide per year and requires a relatively modest initial investment. The current cost of goods for aptamer synthesis at the kilogram scale is estimated at $500/g, comparable to that for highly optimized antibodies. Continuing improvements in process development are expected to lower the cost of goods to <$100/g in five years.

5) Stability. Therapeutic aptamers are chemically robust. They are intrinsically adapted to regain activity following exposure to heat, denaturants, etc. and can be stored for extended periods (>1 yr) at room temperature as lyophilized powders. In contrast, antibodies must be stored refrigerated.

The human immunodeficiency virus (HIV), the cause of acquired immunodeficiency syndrome (AIDS), remains an extremely serious threat to public health worldwide. Globally, over 40 million people are infected with HIV, with roughly 14,000 new infections arising each day (UNAIDS Report, 2002). Clearly, the best long-term solution for controlling the AIDS epidemic is development of a safe and effective HIV vaccine. The gp120 subunit is the primary viral antigen against which humoral immune responses are mounted (Profy, 1990; reviewed in Poignard et al., 2001). The mature envelope glycoprotein exists as a trimer that arises through processing of a larger precursor (gp160) to gp120 and gp41 components which non-covalently associate on the virion surface (Kowalski, et al., 1987; Lu et al., 1995; Burton, 1997). Each gp120 monomer consists of five constant regions (C1-C5) interspersed with five variable regions (V1-V5) (Starcich et al., 1986). Variable regions tend to be oriented on the outer surface of the protein where they help to shield core regions from immune surveillance. Gp120 is also heavily glycosylated (Leonard, 1990). The surface variability and glycosylation of gp120 reduce its immunogenicity. Though progress is being made in development of vaccines that stimulate cell-mediated immune responses, induction of an effective neutralizing antibody response by an HIV vaccine candidate in a clinical setting remains an urgent and unmet medical need.

Current opinion among researchers on the most efficacious route to HIV vaccine development centers on the need to induce both humoral and cell-mediated immune responses that include broadly neutralizing antibodies, and cytotoxic T-lymphocytes (CTL) and T-helper responses. The CTL cells are CD8+ and the T-helper cells are CD4+. However, vaccine-induced neutralizing antibody responses in clinical trials to date have been weak and ineffective against primary viruses.

Much recent effort has been invested in development of gp120 subunit vaccines (reviewed in Graham, 2002). However, antibodies generated against monomeric gp120 are generally not neutralizing, or at best, are capable only of neutralizing laboratory-adapted strains of HIV (Belshe et al., 1994;

Kahn, et al., 1994) and not the more medically-relevant, primary HIV type 1 (HIV-1) isolates (Cohen, 1994). However, passive antibody studies in nonhuman primate models have shown that neutralizing antibodies do in fact protect against infection (Prince et al., 1991; Putkonen, P. et al., 1991; Emini et al., 1992). Indeed, antibody is the sole immune component that can neutralize virus prior to entry, unlike CTLs which are effective only after establishment of cellular infection. Induction of an effective neutralizing antibody response by a gp120-derived immunogen remains an elusive goal.

Variability of the envelope glycoprotein plays a key role in the exceptional ability of HIV to avoid immune attack. Viral mutations accumulate readily as infection progresses, generating a diverse population of variants, even within a single infected individual, and providing opportunities for escape from CTL control (Gaschen et al., 2002). This diversity presents significant challenges to vaccine design. Together, surface variability and extensive glycosylation contribute to the relatively poor immunogenicity of monomeric gp120 immunogens (Leonard, 1990; Langlois et al., 1998; Kwong et al., 2002; Wei et al., 2003). Interestingly, recent results have shown that infected individuals can and often do generate neutralizing antibody responses. Unfortunately these responses appear to lag behind the rapid evolution of the env gene and are thus unable to resist and clear the high level viremia associated with a productive infection (Wei et al., 2003 and Richman et al., 2003). These results do suggest however that individuals vaccinated with appropriate immunogens may be able to generate an immune response capable of protecting against the relatively low viral loads associated with initial exposure to HIV.

A variety of strategies have been developed in pursuit of effective immune responses to HIV, with testing of immunogens in a number of clinical trials (reviewed in Emini, 2002; Graham, 2002). Live-attenuated HIV vaccines have shown potential to induce protection in nonhuman primates (Nixon et al., 1999). However, safety concerns have largely directed current efforts away from use of live-attenuated and whole-killed viral vaccines. Subunit vaccines, like those used in the recent Vaxgen trial, based on HIV surface proteins (primarily gp120 or gp 160) though safe and generally well-tolerated, have not succeeded in eliciting neutralizing antibody responses across populations (Wantanabe, 2003). Neutralizing antibody responses against laboratory-adapted HIV strains produced by most subunit vaccines are several-fold lower than those seen during HIV-1 infection (Graham et al., 2002). Type-specific neutralization can sometimes be achieved, usually corresponding to the origin of the vaccine antigen. However, neutralization of primary R5 HIV isolates has not been observed (Mascola et al., 1996). Alternative vaccine concepts being evaluated in clinical trials include vectored and DNA vaccines that rely on antigen production within cells and surface display on MHC class I molecules. Emerging evidence suggests that durable CD8+CTL activity can be induced using these approaches (Graham et al., 2002). However, as noted above, CTL-based mechanisms succeed only in eradicating cells that have already become infected. While potentially able to control viral load and attenuate disease, cell-mediated mechanisms alone are unlikely to prevent HIV infection.

Potent and enduring neutralizing antibodies are a critical component of any vaccine-induced immunity. Recently efforts have been made to design better gp120 based immunogens based upon the stabilization of conformations of gp120 known to expose neutralizing epitopes that are normally exposed only transiently during infection. The HIV entry process is complex, involving a sequence of protein-protein contacts choreographed by gp120. HIV binding interactions with CD4 receptor and with CCR5/CXCR4 co-receptors (FIG. 2) each appear to be accompanied by significant structural rearrangement in gp120 (Doranz et al., 1997). Initial binding of CD4 induces a conformational change in gp120 through shifting of variable loops V1 and V2 (FIG. 3), thereby exposing conserved gp120 core residues that comprise the chemokine co-receptor binding site (Wu et al., 1996; Trkola et al., 1996). CD4-inducible (CD4i) antibodies recognizing this unmasked core region (17b, 48d) are reported to have neutralizing activity (Thali et al., 1993; Sullivan et al., 1998). Subsequent binding of gp120 to either CCR5 or CXCR4 stimulates a second conformational shift in gp 120 that enables exposure of the fusion domain of gp41 responsible for fusion of viral and cellular membranes. In one study relying on the conformational changes associated with the HIV entry process, strong neutralizing antibody responses were generated in rhesus macaques using a covalently crosslinked gp120/CD4 complex as an immunogen (Fouts et al., 2002). Unfortunately a significant portion of this effect is likely mediated by anti-CD4 antibody responses. Another recent advance has been in the area of CD4 mimics. Using a scyllatoxin scaffold Martin et al. have engineered a small mini-protein that can functionally mimic that action of CD4 on gp120 (Martin et al., 2003). They propose one use of this mini-protein to be as an immunogen that in conjunction with gp120 will expose the highly conserved CD4-inducible (CD4i) epitope which is normally occluded in the absence of CD4 receptor.

Several lines of biochemical and structural evidence support CD4 binding-induced structural changes in gp120, including: increased protease sensitivity of gp120 variable region loops (Sattentau et al., 1991), as well as CD4-stimulated accessibility of the chemokine receptor binding site (Sattentau et al., 1993; Wu, et al., 1996) and of epitopes for antibodies that compete for co-receptor binding (Thali et al., 1993; Zhang et al., 1999). Recent thermodynamic analysis of gp120/CD4/MAb interactions revealed unusually high changes in entropy upon CD4 binding offering further support for the hypothesis that gp120 undergoes a major conformational change upon receptor binding (Kwong et al., 2002). Structural analysis of the ternary complex of CD4 and gp120 with CD4i neutralizing antibody 17b confirmed that stabilizing interactions with CD4 play a significant role in exposure or formation of the CCR5 binding region (Kwong et al., 1998).

Receptor and co-receptor binding sites are attractive targets for use in vaccine design or for therapeutic intervention as they show conservation among different HIV subtypes and must be exposed on the gp120 surface, at least transiently, in order for the virus to gain entry into cells. The CCR5 binding region, in particular, is one of the most highly conserved surfaces on the gp120 core (Rizzuto et al., 1998). Antibody responses to highly conserved epitopes, integral to the fundamental mechanism of HIV entry, are expected to show neutralizing activity even against diverse HIV subtypes. Thus, there is a need for a preventative, prophylactic agent that can bind specifically to gp120 and induce a conformational change that reveals suitable immunogenic epitopes and results in a humoral immune response to prevent or treat infection of cells by HIV.

BRIEF DESCRIPTION OF THE DRAWINGS

FIG. 11 shows a schematic of routes to gp120 agonists, gp120:gp120 or variant (e.g. ΔC1ΔC5, loop truncations, etc.); CKRA: chemokine receptor or functional analog (e.g. neutralizing antibody 17b, detergent solubilized CCR5, CXCR4, CD4 soluble fragment of CD4 or functional analog (e.g. neutralizing antibody b12)); (−):negative selection step; (+): positive selection step;( ):indicated component is optional for selection.

FIG. 12 shows a schematic of selection pool diversification.

SUMMARY OF THE INVENTION

Figure 1:
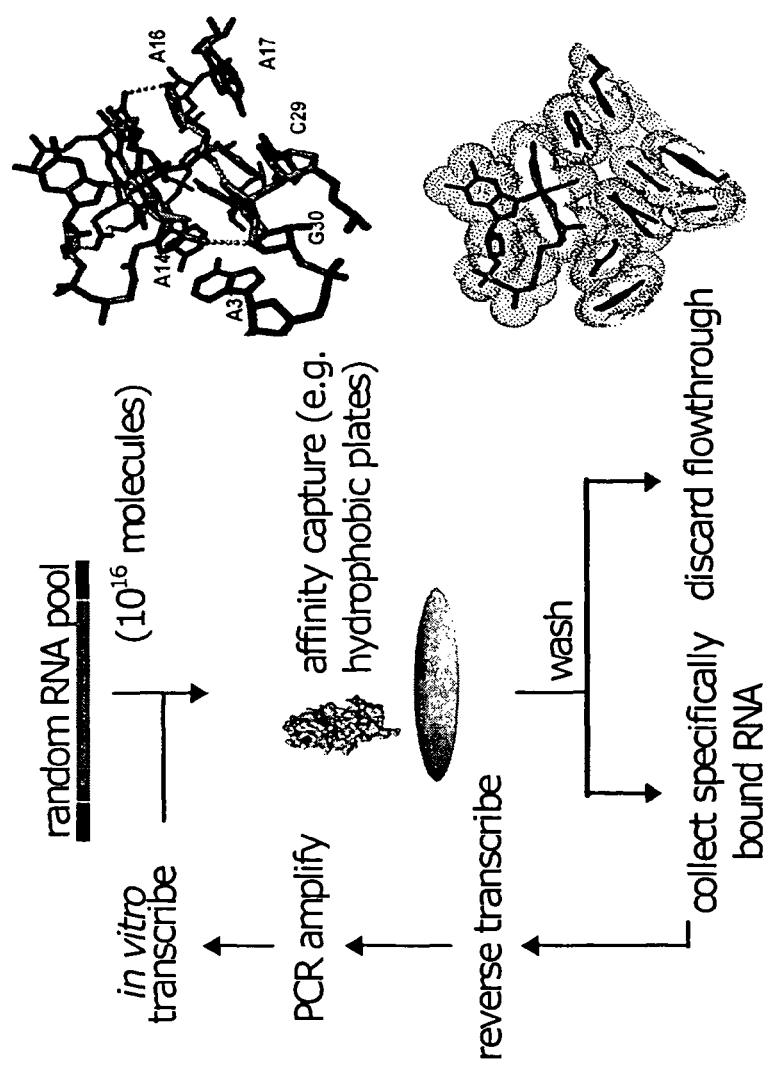
FIG. 1 shows the in vitro aptamer selection (SELEX™, an aptamer selection process) process from pools of random sequence oligonucleotides.
Figure 2:
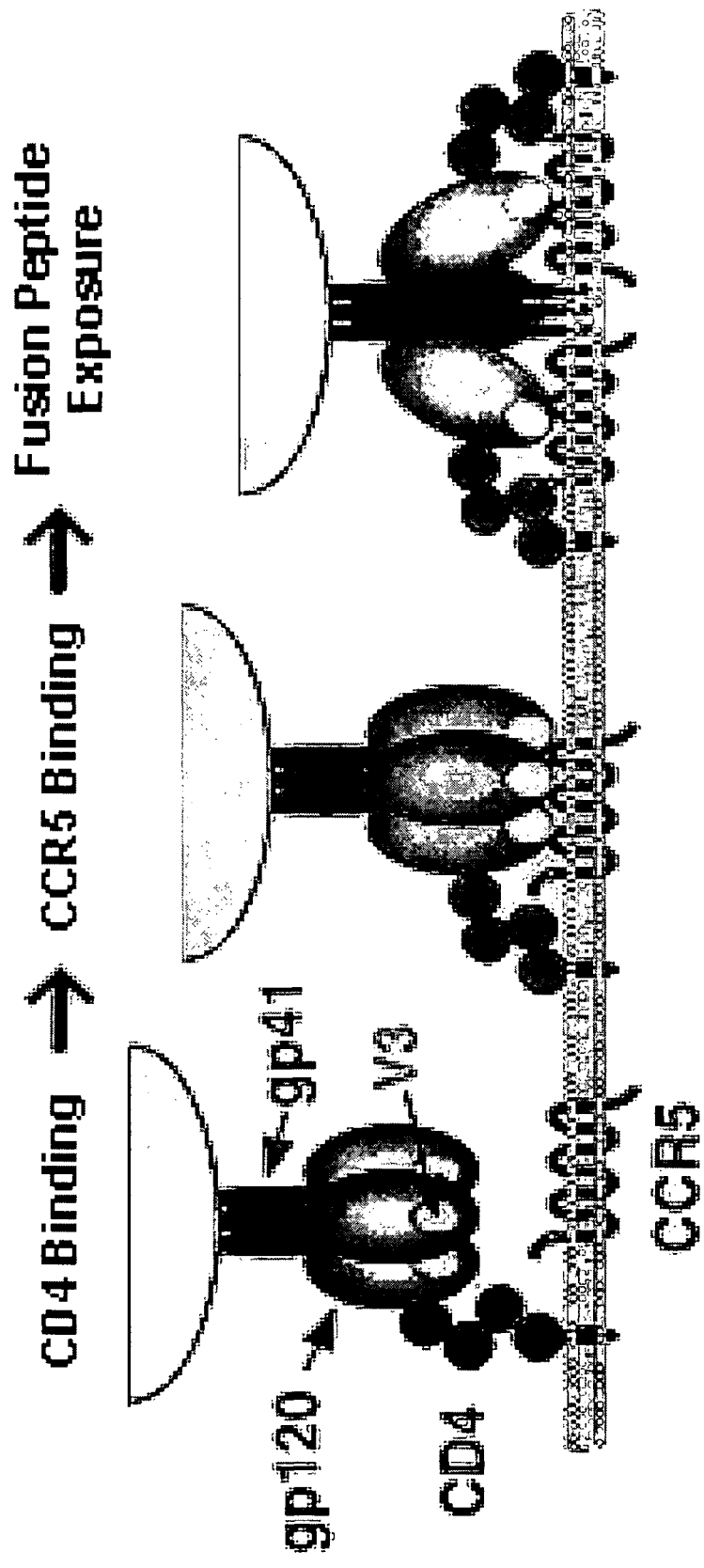
FIG. 2 shows a schematic of HIV infection of cells upon CD4-induced binding of gp120 to CCR5 membrane protein.
Figure 3:
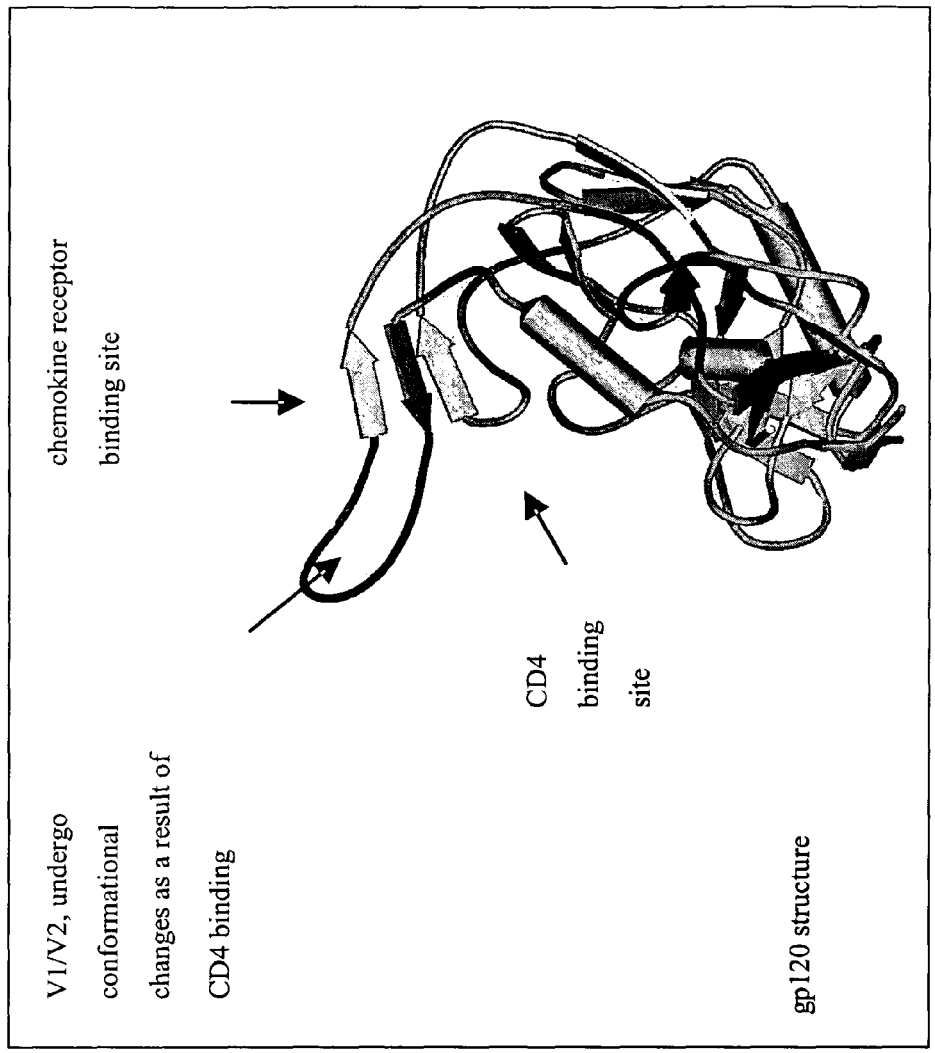
FIG. 3 shows a schematic of HIV binding interactions with CD4 receptor and with CCR5/CXCR4 co-receptors, each of which appear to be accompanied by significant structural rearrangement in gp120.

A novel aspect of the current invention is the use of SELEX™ (an aptamer selection process) to isolate nucleic acids that promote specific desired conformational changes in a target of interest ("agonist SELEX™",(an aptamer selection process) In a preferred embodiment, the target of interest is gp120 and the desired conformational change is that which elicits an effective neutralizing antibody response by, e.g., inducing gp120 to assume and "lock" into intermediate structures present during infection. The target of interest may also be a cell surface receptor and the desired conformational change one that triggers an intracellular signaling pathway or a subunit of a viral surface molecule and the desired conformational change one that fixes the subunit in its natural structure as part of the virus.

In one embodiment, the present invention provides aptamers which bind to gp120 to cause a conformational shift in gp120 that exposes conserved epitopes on gp120 to co-receptors on cell membranes.

In one embodiment, the present invention provides aptamers which bind to gp120 to cause a conformational shift in gp120 that exposes epitopes on gp120 to CCR5 receptors.

In one embodiment, the present invention provides aptamers which bind to gp120 to cause a conformational shift in gp120 that exposes epitopes on gp120 to CXCR4 receptors.

In one embodiment, the present invention provides aptamers which bind to gp120 to cause a conformational shift in gp120 that exposes epitopes on gp120 to CCR5 and CXCR4 receptors, said CCR5 and CXCR4 binding epitopes normally blocked in the absence of binding by CD4.

In one embodiment, the present invention provides aptamers that simulate the effect of CD4 binding to gp120.

In one embodiment, the present invention provides a gp120 aptamer-gp120 conjugate that is "locked" in a conformation that presents epitopes that are able to elicit a neutralizing humoral immune response in an animal or in vitro.

In one embodiment, the present invention provides materials and methods of inducing a humoral immune response to gp120 by administering to subjects a gp120 aptamer-gp120 conjugate that is "locked" in a conformation that presents epitopes that are able to elicit a humoral immune response in an animal or in vitro.

In one embodiment, the present invention provides materials and methods of immunizing subjects against HIV infection by administering an effective amount of an aptamer which binds to gp120 to cause a conformational shift in gp120 that exposes epitopes on gp120 to CCR5 receptors.

In one embodiment, the present invention provides a method of producing neutralizing antibodies specific to gp120 by administering to a subject an aptamer-gp120 conjugate that is "locked" in a conformation that presents epitopes that are able to elicit a humoral immune response in an animal or in vitro.

The present invention also provides aptamer regulators that can be used, e.g., to alter biological activity of a therapeutic target in response to changes in the concentration of another regulator molecule. More specifically, the present invention provides aptamers wherein binding of the aptamer to an effector ligand regulates, i.e., activates or suppresses, binding of the effector ligand to a third molecule by, e.g., altering the conformation of the aptamer-bound (effector) ligand.

In one embodiment, the present invention provides therapeutic aptamers whose binding activity is controlled by a first ligand which suppresses the binding activity of the therapeutic aptamer.

In one embodiment, the present invention provides therapeutic aptamers whose binding activity is controlled by a first ligand which enhances the binding activity of the therapeutic aptamer.

In one embodiment, the present invention provides therapeutic aptamers that bind to the CCR5 receptor (thus altering gp120 binding).

DETAILED DESCRIPTION OF THE INVENTION

Definitions

As defined herein, aptamers are nucleic acid molecules having specific binding affinity to molecules through interactions other than classic Watson-Crick base pairing.

The SELEX™ (an aptamer selection process) Method

A suitable method for generating an aptamer to gp120 is with the process entitled "Systematic Evolution of Ligands by EXponential Enrichment" ("SELEX™", (an aptamer selection process) generally depicted in FIG. 1. The SELEX™ (an aptamer selection process) process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX™ (an aptamer selection process)-identified nucleic acid ligand is a specific ligand of a given target compound or molecule. The SELEX™ (an aptamer selection process) process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

SELEX™ (an aptamer selection process) relies as a starting point upon a large library of single stranded oligonucleotide templates comprising randomized sequences derived from chemical synthesis on a standard DNA synthesizer. In some examples, a population of 100% random oligonucleotides is screened. In others, each oligonucleotide in the population comprises a random sequence and at least one fixed sequence at its 5' and/or 3' end which comprises a sequence shared by all the molecules of the oligonucleotide population. Fixed sequences include sequences such as hybridization sites for PCR primers, promoter sequences for RNA polymerases (e.g., T3, T4, T7, SP6, and the like), restriction sites, or homopolymeric sequences, such as poly A or poly T tracts, catalytic cores (described further below), sites for selective binding to affinity columns, and other sequences to facilitate cloning and/or sequencing of an oligonucleotide of interest.

The random sequence portion of the oligonucleotide can be of any length and can comprise ribonucleotides and/or deoxyribonucleotides and can include modified or non-natural nucleotides or nucleotide analogs. See, e.g., U.S. Pat. Nos. 5,958,691; 5,660,985; 5,958,691; 5,698,687; 5,817,635; and 5,672,695, PCT publication WO 92/07065. Random oligonucleotides can be synthesized from phosphodiester-linked nucleotides using solid phase oligonucleotide synthesis techniques well known in the art (Froehler et al., Nucl. Acid Res. 14:5399-5467 (1986); Froehler et al., Tet. Lett. 27:5575-5578 (1986)). Oligonucleotides can also be synthesized using solution phase methods such as triester synthesis methods (Sood et al., Nucl. Acid Res. 4:2557 (1977); Hirose et al., Tet. Lett., 28:2449 (1978)). Typical syntheses carried out on automated DNA synthesis equipment yield $10^{15}$-$10^{17}$ molecules. Sufficiently large regions of random sequence in the sequence design increases the likelihood that each synthesized molecule is likely to represent a unique sequence.

To synthesize randomized sequences, mixtures of all four nucleotides are added at each nucleotide addition step during the synthesis process, allowing for random incorporation of nucleotides. In one embodiment, random oligonucleotides comprise entirely random sequences; however, in other embodiments, random oligonucleotides can comprise stretches of nonrandom or partially random sequences. Partially random sequences can be created by adding the four nucleotides in different molar ratios at each addition step.

Template molecules typically contain fixed 5' and 3' terminal sequences which flank an internal region of 30-50 random nucleotides. A standard (1 μmole) scale synthesis will yield $10^{15}$-$10^{16}$ individual template molecules, sufficient for most SELEX™ (an aptamer selection process) experiments. The RNA library is generated from this starting library by in vitro transcription using recombinant T7 RNA polymerase. This library is then mixed with the target under conditions favorable for binding and subjected to step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX™ (an aptamer selection process) method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

Within a nucleic acid mixture containing a large number of possible sequences and structures, there is a wide range of binding affinities for a given target. A nucleic acid mixture comprising, for example a 20 nucleotide randomized segment can have $4^{20}$ candidate possibilities. Those which have the higher affinity constants for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

In one embodiment of SELEX™ (an aptamer selection process), the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX™ (an aptamer selection process) until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX™ (an aptamer selection process) process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX™ (an aptamer selection process) procedures with contiguous randomized segments be initiated with nucleic acid sequences containing a randomized segment of between about 20-50 nucleotides.

The core SELEX™ (an aptamer selection process) method has been modified to achieve a number of specific objectives. For example, U.S. Pat. No. 5,707,796 describes the use of SELEX™ (an aptamer selection process) in conjunction with gel electrophoresis to select nucleic acid molecules with specific structural characteristics, such as bent DNA. U.S. Pat. No. 5,763,177 describes SELEX™ (an aptamer selection process) based methods for selecting nucleic acid ligands containing photoreactive groups capable of binding and/or photocrosslinking to and/or photoinactivating a target molecule. U.S. Pat. No. 5,567,588 and U.S. application Ser. No. 08/792,075, filed Jan. 31, 1997, entitled "Flow Cell SELEX™ (an aptamer selection process)", describe SELEX™ (an aptamer selection process) based methods which achieve highly efficient partitioning between oligonucleotides having high and low affinity for a target molecule. U.S. Pat. No. 5,496,938 describes methods for obtaining improved nucleic acid ligands after the SELEX™ (an aptamer selection process) process has been performed. U.S. Pat. No. 5,705,337 describes methods for covalently linking a ligand to its target.

SELEX™ (an aptamer selection process) can also be used to obtain nucleic acid ligands that bind to more than one site on the target molecule, and to obtain nucleic acid ligands that include non-nucleic acid species that bind to specific sites on the target. SELEX™ (an aptamer selection process) provides means for isolating and identifying nucleic acid ligands which bind to any envisionable target, including large and small biomolecules including proteins (including both nucleic acid-binding proteins and proteins not known to bind nucleic acids as part of their biological function) cofactors and other small molecules. For example, see U.S. Pat. No. 5,580,737 which discloses nucleic acid sequences identified through SELEX™ (an aptamer selection process) which are capable of binding with high affinity to caffeine and the closely related analog, theophylline.

Counter-SELEX™ (an aptamer selection process) is a method for improving the specificity of nucleic acid ligands to a target molecule by eliminating nucleic acid ligand sequences with cross-reactivity to one or more non-target molecules. Counter-SELEX™ (an aptamer selection process) is comprised of the steps of a) preparing a candidate mixture of nucleic acids; b) contacting the candidate mixture with the target, wherein nucleic acids having an increased affinity to the target relative to the candidate mixture may be partitioned from the remainder of the candidate mixture; c) partitioning the increased affinity nucleic acids from the remainder of the candidate mixture; d) contacting the increased affinity nucleic acids with one or more non-target molecules such that nucleic acid ligands with specific affinity for the non-target molecule(s) are removed; and e) amplifying the nucleic acids with specific affinity to the target molecule to yield a mixture of nucleic acids enriched for nucleic acid sequences with a relatively higher affinity and specificity for binding to the target molecule.

One potential problem encountered in the use of nucleic acids as therapeutics and vaccines is that oligonucleotides in their phosphodiester form may be quickly degraded in body fluids by intracellular and extracellular enzymes such as endonucleases and exonucleases before the desired effect is manifest. The SELEX™ (an aptamer selection process) method thus encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX™ (an aptamer selection process)-identified nucleic acid ligands containing modified nucleotides are described in U.S. Pat. No. 5,660,985, which describes oligonucleotides containing nucleotide derivatives chemically modified at the 5' and 2' positions of pyrimidines. U.S. Pat. No. 5,756,703 describes oligonucleotides containing various 2'-modified pyrimidines. U.S. Pat. No. 5,580,737 describes highly specific nucleic acid ligands containing one or more nucleotides modified with 2'-amino (2'-$NH_2$), 2'-fluoro (2'-F), and/or 2'-O-methyl (2'-OMe) substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping. In preferred embodiments of the instant invention, the nucleic acid ligands are RNA molecules that are 2'-fluoro (2'-F) modified on the sugar moiety of pyrimidine residues.

The modifications can be pre- or post-SELEX™ (an aptamer selection process) process modifications. Pre-SELEX™ (an aptamer selection process) process modifications yield nucleic acid ligands with both specificity for their SELEX™ (an aptamer selection process) target and improved in vivo stability. Post-SELEX™ (an aptamer selection process) process modifications made to 2'-OH nucleic acid ligands can result in improved in vivo stability without adversely affecting the binding capacity of the nucleic acid ligand.

Other modifications are known to one of ordinary skill in the art. Such modifications may be made post-SELEX™ (an aptamer selection process) process (modification of previously identified unmodified ligands) or by incorporation into the SELEX™ (an aptamer selection process) process.

The SELEX™ (an aptamer selection process) method encompasses combining selected oligonucleotides with other selected oligonucleotides and non-oligonucleotide functional units as described in U.S. Pat. Nos. 5,637,459 and 5,683,867. The SELEX™ (an aptamer selection process) method further encompasses combining selected nucleic acid ligands with lipophilic or non-immunogenic high molecular weight compounds in a diagnostic or therapeutic complex, as described in U.S. Pat. No. 6,011,020. VEGF nucleic acid ligands that are associated with a lipophilic compound, such as diacyl glycerol or dialkyl glycerol, in a diagnostic or therapeutic complex are described in U.S. Pat. No. 5,859,228.

VEGF nucleic acid ligands that are associated with a lipophilic compound, such as a glycerol lipid, or a non-immunogenic high molecular weight compound, such as polyalkylene glycol are further described in U.S. Pat. No. 6,051,698. VEGF nucleic acid ligands that are associated with a non-immunogenic, high molecular weight compound or a lipophilic compound are further described in PCT Publication No. WO 98/18480. These patents and applications allow the combination of a broad array of shapes and other properties, and the efficient amplification and replication properties, of oligonucleotides with the desirable properties of other molecules.

The identification of nucleic acid ligands to small, flexible peptides via the SELEX™ (an aptamer selection process) method has also been explored. Small peptides have flexible structures and usually exist in solution in an equilibrium of multiple conformers, and thus it was initially thought that binding affinities may be limited by the conformational entropy lost upon binding a flexible peptide. However, the feasibility of identifying nucleic acid ligands to small peptides in solution was demonstrated in U.S. Pat. No. 5,648,214. In this patent, high affinity RNA nucleic acid ligands to substance P, an 11 amino acid peptide, were identified.

To generate oligonucleotide populations which are resistant to nucleases and hydrolysis, modified oligonucleotides can be used and can include one or more substitute internucleotide linkages, altered sugars, altered bases, or combinations thereof. In one embodiment, oligonucleotides are provided in which the P(O)O group is replaced by P(O)S ("thioate"), P(S)S ("dithioate"), P(O)NR$_2$ ("amidate"), P(O)R, P(O)OR', CO or CH$_2$ ("formacetal") or 3'-amine (—NH—CH$_2$—CH$_2$—), wherein each R or R' is independently H or substituted or unsubstituted alkyl. Linkage groups can be attached to adjacent nucleotide through an —O—, —N—, or —S— linkage. Not all linkages in the oligonucleotide are required to be identical.

In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described in Sproat, et al., Nucl. Acid Res. 19:733-738 (1991); Cotten, et al., Nucl. Acid Res. 19:2629-2635 (1991); and Hobbs, et al., Biochemistry 12:5138-5145 (1973). The use of 2-fluoro-ribonucleotide oligomer molecules can increase the sensitivity of a nucleic acid sensor molecule for a target molecule by ten-to-one hundred-fold over those generated using unsubstituted ribo- or deoxyribooligonucleotides (Pagratis, et al., Nat. Biotechnol. 15:68-73 (1997)), providing additional binding interactions with a target molecule and increasing the stability of the secondary structure(s) of the nucleic acid sensor molecule (Kraus, et al., Journal of Immunology 160:5209-5212 (1998); Pieken, et al., Science 253:314-317 (1991); Lin, et al., Nucl. Acids Res. 22:5529-5234 (1994); Jellinek, et al. Biochemistry 34:11363-11372 (1995); Pagratis, et al., Nat. Biotechnol 15:68-73 (1997)).

Nucleic acid aptamer molecules are generally selected in a 5 to 20 cycle procedure. In one embodiment, heterogeneity is introduced only in the initial selection stages and does not occur throughout the replicating process.

Methods For Generating gp120 Aptamers

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference.

Figure 8:
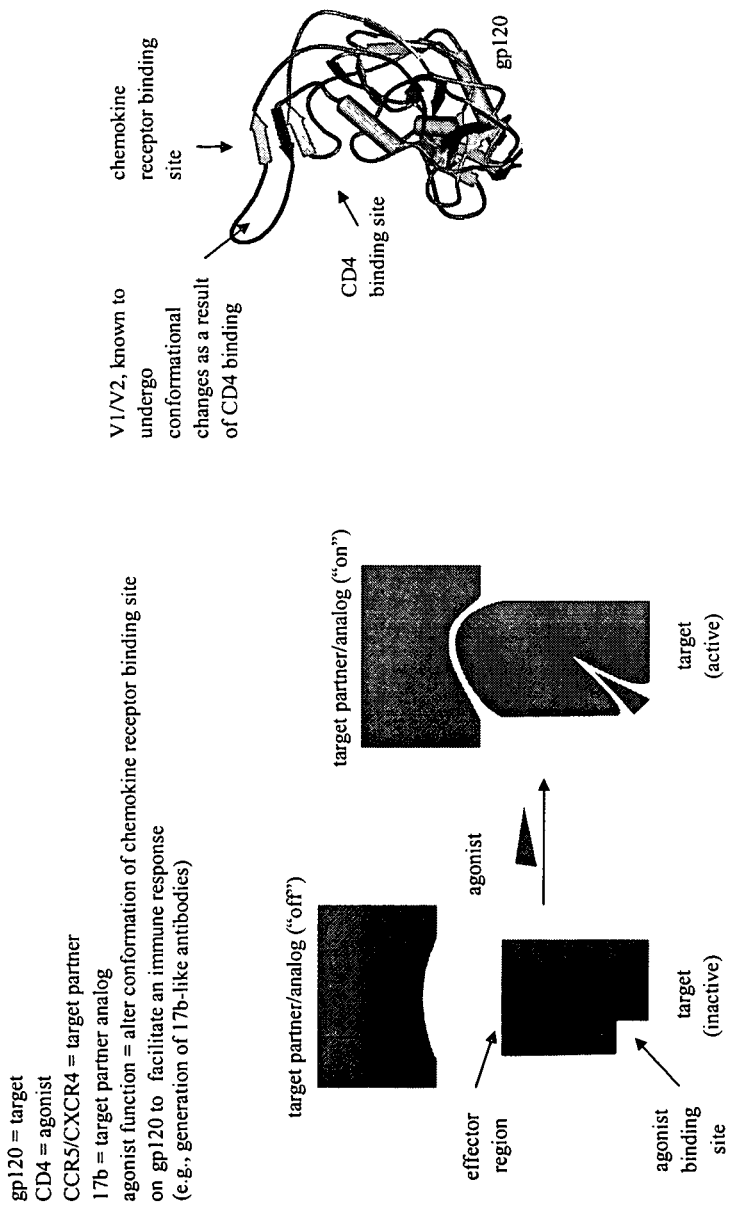
FIG. 8 shows a schematic of an agonist (e.g., a gp120 specific aptamer) inducing conformational changes in a target (e.g., gp120) to facilitate a specific interaction (e.g., binding) with a target partner (e.g., CCR5 or CXCR4) or a target partner analog (e.g., an antibody that recognizes the CCR5 or CXCR4 binding site on gp120).
Figure 9:
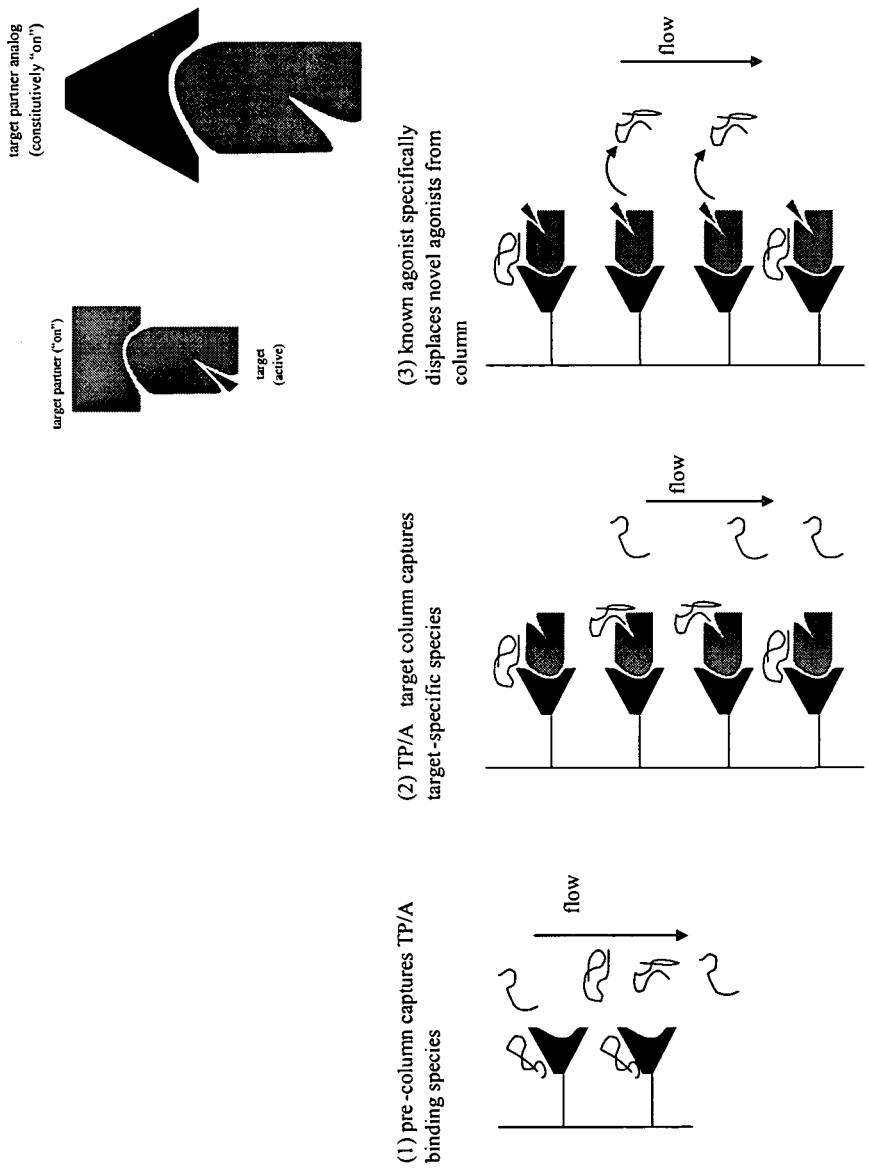
FIG. 9 shows a schematic of an agonist SELEX™ (an aptamer selection process) strategy. In this strategy, a target partner (or "TP") or a target partner analog (or "TPA") with agonist-independent affinity for the target is used to screen a diverse molecule library for species which can specifically interact with the TP (or TPA)-target complex. Agonist species may be specifically enriched by (1) selecting against binding to the TP/A, (2) selecting for molecules specifically retained on an immobilized TP/A-target complex, and (3) specifically released from the TP/A-target complex by known high affinity agonists.
Figure 10:
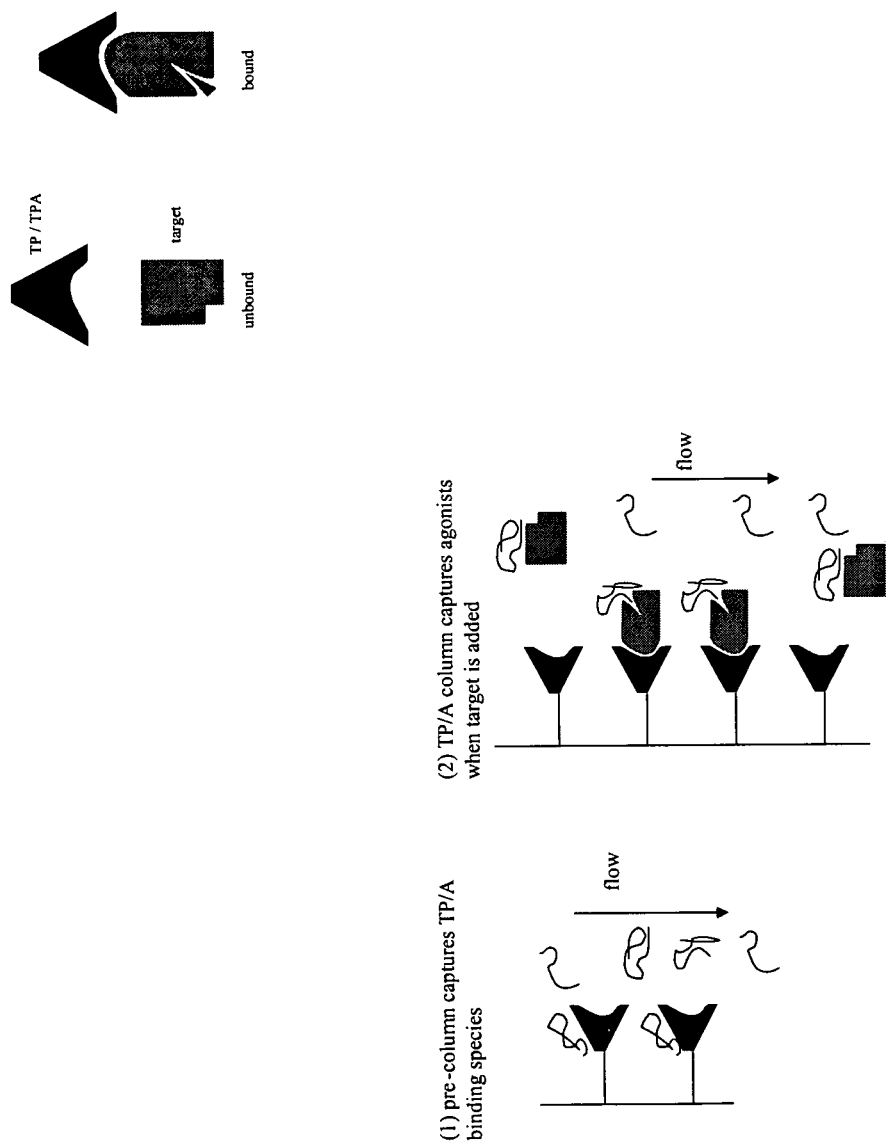
FIG. 10 shows a schematic of a second agonist SELEX™ (an aptamer selection process) strategy. In this strategy, a target partner or target partner analog is used to screen a diverse molecule library for species which can specifically facilitate formation of the TP (or TPA)-target complex under experimental conditions (e.g., temperature, denaturant, salt concentration, target concentration, or TP/A concentration) such that agonist binding is a prerequisite for target-TP/A complex formation. Agonist species may be specifically enriched by (1) selecting against binding to TP/A and (2) selecting for molecules specifically retained only when the target is added to the immobilized TP (or TPA).
Figure 11:
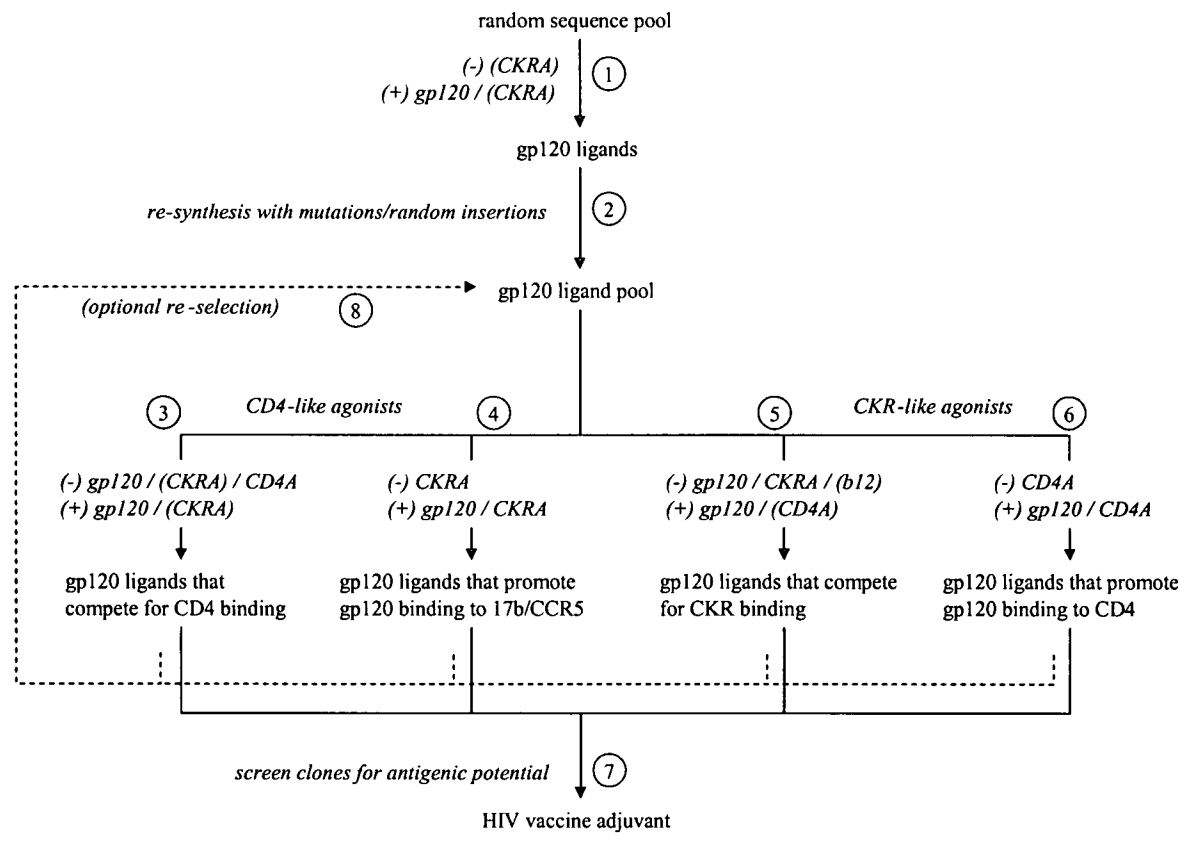

Without wishing to be bound by theory, the current invention describes novel methods for producing aptamers with the ability to induce conformational changes in their targets ("agonist SELEX™", an aptamer selection process) and specifically their application, preferably as an adjuvant to be used in conjunction with gp120, as a prophylactic vaccine. Steps central to the agonist SELEX™ (an aptamer selection process) method are illustrated in FIGS. 8-10. Specific methods used to generate the HIV vaccine adjuvants are illustrated in FIG. 11.

Aptamers with potential utility as HIV vaccine adjuvants can be isolated on the basis of their ability to drive conformational changes in gp420 similar to those induced by the natural gp120 receptors/co-receptors (namely CD4 and CCR5/CXCR4). Previously isolated and characterized neutralizing antibodies are known to map to the CD4 and chemokine receptor binding sites. These antibodies can be used both as proxy receptors to partially drive appropriate conformational changes for aptamer selection (FIG. 9) and as probes for detecting appropriate conformational changes induced by aptamers (FIG. 10). As shown schematically in FIG. 8, binding of an agonist to a target promotes conformational changes in the target which change the nature of the target's interaction (e.g., binding) with a target partner. Typically, the interaction between the target and the target partner promoted by the agonist initiates a signaling pathway within a cell. In a common example, the target is a membrane receptor, the agonist is a peptide or protein ligand or as disclosed herein, an aptamer, and the target partner is an intracellular signaling molecule. In the case of HIV infection, CD4 can be described as an agonist, acting upon the target gp120 to promote its interaction with the target partner CCR5 or CXCR4. An aptamer adjuvant for use as an HIV vaccine would function as an agonist to cause a conformational change in the target (gp120) to expose conserved epitopes and thereby drive association between the target (gp120) and a B-cell receptor.

As used herein, "agonist" means any molecule (preferably, an aptamer) that upon binding to the target induces an appropriate conformational change in the target. As used herein, "target partner" (or "TP") means a molecule that specifically interacts (e.g., binds) to the target. As used herein, "target partner analog" (or "TPA") means a molecule (such as an antibody) that interacts with a target in a manner similar to that of the target partner (e.g., binding at the same or an overlapping site on the target). As used herein, "target partner/ analog (or "TP/A") means either or both a target partner or target partner analog. In the process of "agonist SELEX™" (an aptamer selection process), aptamers are isolated on the basis of their ability to (1) specifically interact with a target which has been driven into an agonist-bound conformation through association with a target partner or an analog thereof, and/or (2) specifically drive association of a target with a target partner or an analog thereof. For in vitro selection of gp120 agonists, the target partner receptor (corresponding to a membrane-associated form of a neutralizing antibody expressed on the surface of a B-cell) can be functionally substituted by target partner analogs such as CCR5, CD4, 17b, or b12 (or fragments thereof)—species that are all known to bind to epitopes that drive the binding of neutralizing antibodies. As described below, some agonist SELEX™ (an aptamer selection process) strategies rely upon an agonist competitor. An agonist competitor is a molecule that interacts with the target at the same site as the agonist and which can be used to competitively elute target-bound agonists.

Aptamers with desired agonist properties can be generated by the broad strategies outlined in FIG. 9 and FIG. 10 and by a number of specific routes, as illustrated in FIG. 11. Initially, all routes start with selection from a random sequence pool for gp120-specific aptamers or ligands (Step 1). The gp120-specific aptamer(s) are then used as the starting point for the generation of a biased pool of molecules, predisposed to gp120 binding (Step 2). A variety of negative and positive selection pressures can be used to specifically enrich aptamers which trigger conformational changes similar to those generated by receptor/co-receptor-binding (Steps 3-6). Steps 3-6 will individually enrich aptamers within the pool generated in Step 2 for molecules with agonist properties. Subsequent high-throughput screening of individual clones within the enriched pools can be used to identify optimal aptamers for use as adjuvants (Step 7). Alternatively, pools enriched by one step can be used as the starting point for subsequent enrichment via another step (Step 8). In addition, Step 1 and/or Step 2 may be dispensed with altogether such that the ability to bind to gp120 and the ability to cause the appropriate conformational shift in gp120 are selected for simultaneously. By combining multiple selection strategies, aptamers with agonist activity may be most efficiently enriched and ultimately isolated. Detailed methods by which each of the steps in FIG. 4 can be carried out are described in the following sections.

Step 1: gp120-specific aptamer selection. In the initial step, aptamers are selected from random sequence pools for specific binding to target (e.g., gp120). In the preferred embodiment, aptamers are derived from the SELEX™ (an aptamer selection process) methodologies previously described. For example, the gp120 specific aptamers can be derived as described below:

(A) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (i) to assist in the amplification steps described below, (ii) to mimic a sequence known to bind to the target, or (iii) to enhance the concentration of a given structural arrangement of the nucleic acids in the candidate mixture. The randomized sequences can be totally randomized (i. e., the probability of finding a base at any position being one in four) or only partially randomized (e.g., the probability of finding a base at any location can be selected at any level between 0 and 100 percent).

(B) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

(C) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5-50%) are retained during partitioning.

(D) Those nucleic acids selected during partitioning as having the relatively higher affinity for the target are then amplified to create a new candidate mixture that is enriched in nucleic acids having a relatively higher affinity for the target. This new candidate mixture is contacted with the selected target under conditions favorable for binding between the target and members of the new candidate mixture to form additional nucleic acid-target pairs.

(E) Steps (C) and (D), partitioning and amplification, respectively, are then repeated until the desired number and types of sequences are obtained.

By repeating the partitioning and amplifying steps above, the newly formed candidate mixture contains fewer and fewer unique sequences, and the average degree of affinity of the nucleic acids to the target will generally increase. Taken to its extreme, the SELEX™ (an aptamer selection process) process yields a candidate mixture containing one or a small number of unique nucleic acids representing those nucleic acids from the original candidate mixture having the highest affinity to the target molecule.

The aptamers of the invention can also be prepared through the basic SELEX™ (an aptamer selection process) methodology modified in any manner described herein. The SELEX™ (an aptamer selection process) process can be performed using purified gp120, or discrete domains or fragments (collectively, "fragments") thereof. Alternatively, full-length gp120, or gp120 fragments, can be produced in a suitable expression system. Alternatively, the SELEX™ (an aptamer selection process) process can be performed using as a target a synthetic peptide that includes sequences found in gp120. Determination of the precise number of amino acids needed for the optimal nucleic acid ligand is routine experimentation for skilled artisans. The gp120 fragments can be used in the SELEX™ (an aptamer selection process) process for both negative selections and as the target in lieu of full length gp120 in positive selections. Fragments useful in negative selections are described below. Fragments most likely to be useful in positive selections would be those including the V1 and V2 regions and/or lacking the C1 and/or C5 regions. The identification of other fragments useful in positive selections can be determined by routine experimentation for skilled artisans. Briefly, one would immunize mice or rhesus macaques with various gp120 constructs and screen sera for ability to neutralize HIV infection in vitro. gp120 constructs identified which generate the strongest neutralizing response would be chosen. Alternatively, once a gp120-aptamer conjugate has been identified as a useful HIV vaccine, both or either of the aptamer or gp120 could be minimized by deleting portions (e.g., the C1 and/or C5 regions of gp120 or the termini or other nonessential regions of the aptamer), mixing the minimized gp120 and/or aptamer to form conjugates, testing the new conjugate for activity and comparing it to the activity of the full length gp120-aptamer construct.

In a preferred embodiment, the SELEX™ (an aptamer selection process) process is carried out using fragments of gp120 that are bound to magnetic beads through hydrophobic interactions. A candidate mixture of single stranded RNA molecules is then contacted with the magnetic beads in the wells of a microtiter plate. After incubation for a predetermined time at a selected temperature, the beads are held to the sides of the wells of the plate by a magnetic field, and the wells of the plate are washed to remove unbound candidate nucleic acid ligands. The nucleic acid ligands that bind to gp120 are then released into solution in the wells, then reverse transcribed by reverse transcriptase and amplified using the Polymerase Chain Reaction (PCR). The amplified candidate mixture is then used to begin the next round of the SELEX™ (an aptamer selection process) process.

In a preferred embodiment, 5-10 cycles of the SELEX™ (an aptamer selection process) process are carried out to isolate a pool of molecules with high affinity and specificity for the target (gp120).

Step 2: Generation of a diverse gp120 aptamer-based pool. To increase the likelihood of isolating not only high affinity ligands but also ligands that induce the appropriate conformational changes in the target, the pool of gp120 aptamers in Step 1 is "diversified"—i.e., sequence variation is introduced into the selected clones to increase functional diversification. This can be achieved by a combination of several methods including the following:

(A) Individual clones present in the original selection are isolated and characterized. Characterization can include (i) assay for binding affinity, (ii) sequencing, (iii) truncation to define a minimal contiguous domain responsible for binding, (iv) generation of an artificial phylogeny of functional molecules (e.g., via random mutagenesis of the aptamer clone, re-selection of the mutagenized pool for binding species (employing the same SELEX™, an aptamer selection process, process used with the original random pool), sequencing of the re-selected clones, and analysis of the sequenced clones for conserved sequences and structures required for binding). Information obtained by these experiments can be used to direct the chemical synthesis of a new pool of sequences related to the original aptamer clone (some examples are shown in FIG. 12).

(B) One or more of the aptamers isolated in the original selection (Step 1) can be used as templates for PCR amplification under mutagenic conditions. Repeated rounds of polymerase-mediated replication lead to incorporation of mutations throughout the aptamer sequence(s).

(C) Random sequence tags can be added to the 5'- and/or 3'-ends of an aptamer or pool of aptamers by either PCR with a random sequence primer or ligation of a random sequence tag (FIG. 12).

Multiple pool designs can be used in parallel with identical selection protocols to increase the diversity of functional species. In fact, under identical selection conditions, random pools built into a structured ribozyme framework have yielded aptamers in cases where traditional unstructured pools have not. These results suggest that providing some initial stem structure in pools might shift the pools in the nucleic acid thermodynamic/structural landscape into a region more broadly accessible to bind complex or difficult epitopes.

Steps 3-6: Selection schemes to isolate gp120 agonists. As diagrammed in FIG. 11, the pool of gp120 aptamer-based sequences obtained in Step 2 is subjected to variations on the SELEX™ (an aptamer selection process) process in steps 3-6 to enrich species with or likely to have agonist activity. The output from each Step may be assayed for agonist activity or, alternatively, be provided as input for another step of selection. For example, Steps 3-4 are designed to isolate gp120 aptamer agonists with CD4-like activity (i.e., prone to induce the conformational changes in gp120 similar to those induced by binding of CD4). Similarly, Steps 5-6 are designed to isolate gp120 aptamer agonists with chemokine receptor-like activity (i.e., prone to induce conformational changes in gp120 similar to those induced by binding of CCR5/CXCR4). As such, Steps 3 and 4 can be combined successively to yield one class of agonists while Steps 5 and 6 can be combined successively to yield another.

Step 3: Selection for aptamers that compete for the CD4 binding site of gp120. Selection for CD4-like agonists by this method follows the general strategy outlined in FIG. 9. The pool of sequences generated in Step 2 is subjected to repeated rounds of selection as follows:

(1) The pool of gp120 aptamer based sequences is contacted with the immobilized target partner/analog and allowed to bind under conditions that favor specific binding. In the most preferred embodiment, the target partner/analog is the neutralizing antibody 17b, bound to immobilized protein A. Non-binding species are collected and passed forward for subsequent steps.

(2) Target (gp120) or a fragment thereof is immobilized by attachment to a solid support using the immobilized TP/A which, under the experimental conditions is capable of binding the target with high affinity. In the most preferred embodiment, the target is recombinantly expressed gp120/ΔC1ΔC5. The pool of selected sequences is contacted with the immobilized target (gp120) and allowed to bind under conditions that favor specific binding and the species with low affinity for target are removed by stringent washing and discarded.

(3) Excess agonist competitor (e.g., CD4) is combined with the retained pool fraction. CD4 has high affinity for gp120 and will competitively displace aptamers that bind to gp120 via sites that overlap with the CD4 binding site. Species specifically eluted by the known agonist are enzymatically amplified as described earlier.

The above process is repeated until a significant fraction of the input pool is captured and specifically eluted. In the preferred embodiment, this process is repeated 5-10 times.

As an alternative to the above process, an immobilized complex between target (gp 120), agonist competitor (e.g., CD4), and optionally the target partner/analog (e.g., 17b) can be used first in a negative selection step (i.e., the random sequence pool is contacted with said complex and only non-binding species are collected and passed forward for subsequent steps). Molecules surviving negative selection are subsequently contacted with an immobilized complex containing the target (gp120) and optionally the target partner/analog (17b) but lacking the agonist competitor. Molecules with affinity for the complex are isolated by stringent washing, followed by denaturation.

The methods described above will preferentially enrich species whose binding site overlaps with that for CD4. While agonists with CD4-like activity would be expected to bind in an overlapping site, several types of parasitic, non-agonist aptamers will additionally be enriched, including, for example, aptamers which only partially overlap with the CD4 binding site and which do not induce the appropriate conformational changes. Previous mutagenesis and crystallographic studies have defined key determinants which direct specific binding between CD4 and gp120 (e.g., Kwong, 1998). These include the V1-V2 extended loop (Thr123-Thr198), Gly366-Asp370, and Met426-Val430. Mutations in these regions are known to disrupt binding and there is evidence that the conformation of these regions is altered as a result of CD4 binding. Aptamer agonists might be expected to rely upon similar interactions to drive target activation and, correspondingly, aptamers that fail to use these interactions may be considered unlikely to drive the appropriate conformational changes. As such, modified targets lacking these sequences/regions and thus agonist binding can be used in negative selection to remove aptamers that bind to the modified targets from the pool.

In an embodiment of this negative selection strategy, gp120 ΔC1/ΔC5/ΔV1-V2 (ΔThr123-Thr198 replaced with the tripeptide Gly-Ala-Gly) is immobilized and contacted with the pool of gp120 aptamer-based sequences under conditions that favor specific binding. Following an incubation period during which specific aptamer-modified target complexes can form, non-bound species are collected and the bound species discarded. Collected species are subsequently passed into a positive selection step for wild-type target (gp120) binding followed by agonist competitive elution. The V1-V2 loop provides approximately half of the contact surface from gp120 in the gp 120-CD4 complex and it directly contacts the 17b neutralizing antibody. Aptamers capable of specific gp120 binding in the absence of V1-V2 are unlikely to interact in a way that would alter the conformation of the V1-V2 loop and thus fail to exhibit agonist activity.

In the same vein, negative selection may be carried out using a gp120 ΔC1/ΔC5/Gly366-Asp370->Ala/ΔMet426-Val430 mutant. These residues are required for the other half of the gp120-CD4 interaction. Since, however, these residues do not directly define the binding site for the target partner, it is possible that active agonists will be removed from the selected pool during this step.

Step 4: Selection for aptamers that promote target binding to a target partner/analog. Agonists isolated by this method follow the general strategy outlined in FIG. 10. Pre-binding of CD4 has been shown to increase the affinity of gp120 for antibody 17b by approximately 10-fold (Zhang, 2001) and for the chemokine receptor CCR5 by 100- to 1000-fold. By adjusting target, agonist, and target partner/analog concentrations and other experimental conditions, this property can be exploited to select target binders that increase the affinity of the target for the target partner/analog.

The target partner/analog (TP/A) is immobilized on a solid support. In the preferred embodiment, the TP/A a sulfotyrosine-rich peptide from CCR5 previously shown to bind specifically to gp 120, immobilized via biotinylation to a streptavidin-coated plate (Cormier et al., 2000). Target (gp120) aptamer-based sequences are optionally contacted with the immobilized TP/A and allowed to bind under conditions that favor specific complex formation. Unbound oligonucleotides (also referred to as "species") are collected and the bound species are discarded.

The negatively selected sequences from (1) are combined with target and immobilized TP/A under conditions that disfavor efficient binding between target alone and TP/A. Species which are capable of specifically interacting with the target in a manner that increases target affinity for the TP/A will be preferentially retained on the solid support while those that do not will remain in solution. In the preferred embodiment, the concentration of target and TP/A are maintained sufficiently low such that less than 1% of either forms a complex in the absence of an agonist species that would increase their propensity for binding. After an equilibration period in which novel agonist species-target-TP/A complexes are allowed to form, unbound species are removed by stringent washing.

Optionally, to promote release of target-binding aptamers which form low affinity ternary complexes (aptamer-target-TP/A), excess free target can be provided to competitively displace weakly bound target.

Specifically retained aptamers can be removed from the immobilized TP/A by denaturation (e.g., by heating) or specifically eluted using, for example, soluble CD4 or 17b Fab (which does not bind protein A).

Step 5: Selection for aptamers that compete for gp120 chemokine receptor binding site. Paralleling efforts directed at the generation of CD4-like agonists, selection can be used to generate aptamers which bind near the chemokine receptor binding site to induce appropriate presentation of the CD4BS epitopes. Aptamers with this specificity can be generated using the methods described in Step 3 with replacement of the agonist competitor CD4 by soluble forms of CCR5 or CXCR4 and replacement of the target partner analog 17b with either soluble CD4 or with the neutralizing antibody b 12. As an example:

(1) The pool of gp120 aptamer based sequences is contacted with the immobilized target partner/analog and allowed to bind under conditions that favor specific binding. Non-binding species are collected and passed forward for subsequent steps.

(2) Target (gp120) or a fragment thereof is immobilized by attachment to a solid support using the immobilized target partner/analog which, under the experimental conditions is capable of binding the target with high affinity. In the most preferred embodiment, the target is recombinantly expressed gp120/ΔC1ΔC5 and the TP/A is monoclonal antibody b12. The pool of selected sequences is contacted with the immobilized target (gp120) and allowed to bind under conditions that favor specific binding. Species with low affinity for target are removed by stringent washing and discarded.

(3) Excess chemokine receptor binding site competitor (e.g., 17b or detergent solubilized CCR5) is combined with the retained pool fraction. CCR5 and 17b have high affinity for gp120 and will competitively displace aptamers that bind to gp120 via sites that overlap with the chemokine receptor binding site. Species specifically eluted by the known agonist are enzymatically amplified as described earlier.

As with the selection for aptamers that interact via the CD4-binding site, selection for chemokine-receptor binding site aptamers will generate non-agonists which interact with a portion of the receptor binding site but do not drive the appropriate conformational changes in the target. These aptamers may be preferentially removed from the selected pool by appropriate negative selection steps involving modified forms of the target in which binding site residues have been deleted or substituted. In the preferred embodiment, a modified form of gp120 lacking the extended V1-V2 variable loop (Thr123-Thr198→Gly-Ala-Gly) is provided during a negative selection step as described previously for CD4-like agonist selection.

Step 6: Selection for aptamers that promote gp120 binding to CD4 or its functional analogs. Paralleling efforts directed at the generation of agonists which increase binding affinity of gp120 for chemokine receptors and their functional analogs, selection can be used to generate aptamers with chemokine receptor-like agonist activity by isolating molecules which promote high affinity binding to CD4 or its functional analogs. Aptamers with this specificity can be generated using the methods described in Step 4 (FIG. 10) with replacement of the agonist CD4 by soluble forms of CCR5 or CXCR4 and replacement of the target partner analog 17b with either soluble CD4 or with the neutralizing antibody b12. As an example:

(1) The target partner/analog is immobilized on a solid support. In the preferred embodiment, the TP/A is b 12 and it is immobilized by non-covalent binding to pre-immobilized protein A using methods for protein A immobilization well-known in the art). Target (gp120) aptamer-based sequences are optionally contacted with the immobilized TP/A and allowed to bind under conditions that favor specific complex formation. Unbound species are collected and the bound species are discarded.

(2) The negatively selected sequences from (1) are combined with target and immobilized TP/A under conditions that disfavor efficient binding between target alone and TP/A. Species which are capable of specifically interacting with the target in a manner that increases target affinity for the TP/A will be preferentially retained on the solid support while those that do not will remain in solution. In the preferred embodiment, the concentration of target and TP/A are maintained sufficiently low such that less than 1% of either forms a complex in the absence of an agonist species that would increase their propensity for binding. After an equilibration period in which novel agonist species-target-TP/A complexes are allowed to form, unbound species are removed by stringent washing.

Optionally, to promote release of target-binding aptamers which form low affinity ternary complexes (aptamer-target-TP/A), excess free target can be provided to competitively displace weakly bound target.

Specifically retained aptamers can be removed from the immobilized TP/A by denaturation (e.g., by heating) or specifically eluted using, for example, non-biotinylated CCR5-derived sulfopeptides with gp120 binding specificity.

Step 7: Post-SELEX engineering/optimization of gp120 agonists for use as vaccine adjuvants. Iterative application of the selection methods described in Steps 3-6 will yield pools enriched for aptamers with the ability to induce conformational changes in gp120 which will increase its ability to elicit an effective immune response as an antigen. To generate a useful aptamer-based vaccine adjuvant, the following additional steps are carried out to identify the best starting candidates within the aptamer pool and to improve their production characteristics for use as an adjuvant.

(1) Clone screening. Individual aptamers isolated in the course of in vitro selection are cloned and characterized for functional activity. In the initial screen, aptamers may be evaluated on the basis of their ability to promote target partner/analog binding to the target. For example, fluorescently labeled gp 120 is combined with a defined amount of CD4-like agonist aptamer clone in an assay plate containing immobilized 17b. Following a binding incubation and stringent washing, retained gp120 can be quantified using a fluorescent plate reader. Aptamers with the strongest agonist activity are expected to most effectively promote gp120 retention in the assay. By testing a range of aptamer concentrations, the highest affinity aptamer agonists may be identified. An advantage of this primary screen is its ability to rapidly evaluate a large number of candidates with minimal effort.

In a secondary screen, aptamers can be tested in moderate throughput for their ability to induce a neutralizing antibody response. Aptamers can be conjugated to recombinantly expressed gp120 by one of several methods described below and formulated together with a conventional adjuvant, such as Ribi (R-700) or cell wall material (R-730) using methods well known in the art). Aptamer complexes are then injected into mice to provoke an immune response. Specifically, mice are injected with 0.05 ml of vaccine in four subcutaneous sites. Booster immunizations are done at 3-week intervals, and mice bled from the tail 10-28 days after immunizations. Ultimately, larger quantities of serum can be obtained by exsanguinations and serum antibodies against gp120 quantitated by gp120 enzyme-linked immunosorbent assay (ELISA) (Moore et al., 1989). Neutralizing activity of sera is then tested in neutralization assays using human peripheral blood mononuclear (PBMC) target cells (Barnett, S.W. et al., 2001).

(2) Clone characterization. Having identified a handful of clones for activity, these clones may be further characterized to improve their production characteristics. Characterization would include the following: (a) Sequencing. Plasmid vectors carrying individual cloned aptamers can be sequenced using conventional, well-established, DNA sequencing methods. (b) Truncation. End-labeled aptamer is subjected to limited hydrolysis, separated on the basis of target (gp120) binding, and analyzed to determine whether hydrolysis fragments partition as bound or unbound species. Through this process, discrete 5'- and 3'-boundaries can be identified which define a minimal contiguous domain responsible for binding. (c) Phylogenetic analysis. An aptamer clone is subjected to random mutagenesis by either mutagenic PCR or doped re-synthesis of an oligonucleotide template for transcription. The mutagenized pool of sequences is subjected to re-selection using one or more steps described previously (Steps 3-6). Functional clones within the re-selected pool are for binding species (employing the same SELEX™ (an aptamer selection process) process used with the original random pool), sequencing of the re-selected clones, and analysis of the sequenced clones for conserved sequences and structures required for binding). (d) Synthesis. Minimal aptamers are synthesized using nucleic acid synthesis techniques which are known in the art.

(3) Optimization of the aptamers. Pharmacokinetic properties of aptamers can be optimized by approaches which increase resistance to endonuclease and exonuclease digestion while preserving high affinity gp120 binding. Use of 2'-fluoro-substituted aptamers in starting pools will confer a high degree of nuclease resistance which can be enhanced still further by introduction of 2'-O-methylpurine residues. 2'-O-methyl substitutions may not be tolerated at all purine sites, since the gp120:aptamer complexes may contain contacts between key 2'-OH groups and gp120. Tolerance for 2'-O-methyl substitutions at purine residues of anti-gp120 aptamers will therefore be tested in 2'-O-methyl purine nucleotide interference assays (Greene et al., 1995). Cap structures at the 5'- and 3'-ends of an aptamers are also known to effectively block exonuclease activity (Floege, 1999; Tucker, 1999; Ruckman, 1998; Dougan, 2000). Candidate 2'-fluoro-pyrimidine and 2'-O-methylpurine-containing aptamers containing 3'-3' thymidine and 3'-biotin cap modifications can be chemically synthesized and tested for gp120 binding and associated binding-induced conformational changes in gp120.

(4) Coupling to gp120. Activity of the aptamer as an effective vaccine adjuvant may require that the aptamer be covalently coupled to gp120. Linkage of aptamers via surface carbohydrate moieties of gp120 offers one means to engineer covalently linked aptamer/gp120 complexes. Anti-gp120 aptamers incorporating a variable-length PEG spacer region will be modified by hydrazine treatment and reacted with periodate-oxidized gp120. The resulting covalent aptamer/gp120 complexes will then be characterized with respect to CD4, CCR5 and antibody interaction, and the capacity to generate neutralizing antibodies. Alternatively, the aptamer and gp120 can be photo-crosslinked as previously described.

Administration, Dose and Treatment Regimes The method for preventing HIV infection or reducing the levels of HIV in infected individuals involves exposing a human to an aptamer-gp120 vaccine, actively inducing antibodies that react with gp120, and preventing/impairing the ability of HIV to infect cells in vivo. This method is appropriate for an uninfected subject or an HIV infected subject with a competent immune system. The method induces antibodies, which react with GP120 and neutralize the ability of virus to infect cells. In acutely exposed, previously uninfected individuals, the method will prevent virus multiplication upon exposure to HIV. For already infected individuals, the method will decrease the levels of circulating virus ("viral load"), ameliorating the effects of the disease. The present invention also encompasses treating HIV infection by the administration of gp120 aptamers unconjugated to gp120.

The terms "treating," "treatment," and the like are used herein to mean obtaining a desired pharmacologic or physiologic effect. The effect can be prophylactic in terms of completely or partially preventing a disorder or sign or symptom thereof, or can be therapeutic in terms of a partial or complete cure for a disorder and/or adverse effect attributable to the disorder. "Treating" as used herein covers any treatment and includes: (a) preventing a disorder from occurring in a subject that can be predisposed to a disorder, but has not yet been diagnosed as having it; (b) inhibiting the disorder, i.e., arresting its development; or (c) relieving or ameliorating the disorder. An "effective amount" or "therapeutically effective amount" is the amount sufficient to obtain the desired physiological effect. Appropriate dosing regimens for the vaccine is generally determined on the basis of controlled clinical trials across patient populations; the effective amount for the vaccine is selected by the physician in each case on the basis of factors normally considered by one skilled in the art to determine appropriate dosages, including the age, sex, and weight of the subject to be treated, the condition being treated, and the severity of the medical condition being treated.

Administration of Aptamer-gp120 Vaccine

The aptamer-gp120 vaccine may be formulated and administered through a variety of means, including systemic, localized or topical administration. Preferably, the aptamer-gp120 vaccine is formulated and administered systemically. Techniques for formulation and administration may be found in "Remington: The Science and Practice of Pharmacy, Twentieth Edition," Lippincott Williams & Wilkins, Philadelphia, Pa. Suitable routes may include but are not limited to oral, rectal, transmucosal or intestinal administration; parenteral delivery, including intramuscular or subcutaneous injections; or intranasal injections.

For systemic administration, injection is preferred, including intramuscular (preferred) and subcutaneous. For injection, the vaccines are formulated in aqueous solutions, preferably in physiologically compatible buffers such as Hanks's solution, Ringer's solution, or physiological saline buffer and may include adjuvants (e.g., alums, polymers, copolymers). In addition, the vaccines may be formulated in solid or lyophilized form, then redissolved or suspended immediately prior to use.

Effective concentrations and frequencies of dosages of the vaccine may be determined through procedures well known to those in the art, which address such parameters as biological half-life, immunologic response, dosing interval, and toxicity. A preferred dosage concentration may range from about 0.1 μg/kg body weight to about 4 μg/kg body weight, with about 0.5 μg/kg body weight being most preferred. Depending on immunogenicity, administration of 2-3 doses at monthly intervals, followed by a booster injection at 6 months and subsequently at yearly intervals, may be sufficient to maintain the required circulating concentration of neutralizing antibody. Dose, dosing interval and number of doses will depend upon the patient population (varying by age, weight, underlying diseases, immunologic status etc.).

The vaccines may be administered to patients alone or in combination with other therapies. Such therapies include the sequential or concurrent administration of small molecule anti HIV inhibitors or antagonists and/or other anti-HIV vaccines that work through different mechanisms (e.g., by generating T-cell-mediated immunity).

Pharmaceutical Compositions

Pharmaceutical compositions suitable for administration will typically comprise the vaccine and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in "Remington: The Science and Practice of Pharmacy, Twentieth Edition," Lippincott Williams & Wilkins, Philadelphia, Pa. Preferred examples of such carriers or diluents include, but are not limited to, water, saline, Ringer's solutions, dextrose solution and phosphate buffered solutions. Adjuvants such as aluminum phosphate, liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intramuscular and subcutaneous, administration. Solutions or suspensions used for parenteral application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. Immunogenicity may be enhanced by the inclusion of adjuvants such as alum or other agents commonly known in the field. The parenteral preparation can be enclosed in ampoules, disposable syringes or multiple dose vials made of glass or plastic. In all cases, the composition must be sterile and should be fluid to the extent that easy syringeability exists. It must be stable under the conditions of manufacture and storage and if formulated in multi-dose vials must be preserved against the contaminating action of microorganisms such as bacteria and fungi.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying, lyophilization and freeze-drying that yields a powder of the active ingredient plus any additional desired ingredient from a previously sterile-filtered solution thereof.

It is especially advantageous to formulate parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Methods for Generating Regulated Aptamers

A regulated aptamer is an aptamer wherein binding of the aptamer to a second ligand (e.g., the CCR5 receptor) is regulated (i.e., activated or suppressed) by binding of the aptamer to a first ligand or effector (e.g., gp120). An aptamer with these properties can be generated using any of the following selection strategies.

Method (1): Selection from naïve sequence pools

Selection for ligand-regulated aptamers is performed with nucleic acid pools containing 2'-fluoropyrimidines for additional serum stability. For the first pool, a DNA template with the sequence: 5'-GCCTGTTGTGAGCCTCCTGTCGAA-3' (SEQ ID NO:1), linked by 40 randomized nucleotides-($N_{40}$)—to 5'-TTGAGCGTTTATTCTTGTCTCCCTAT-AGTGAGTCGTATTA-3' (SEQ ID NO:2), is synthesized using an ABI EXPEDITE™ DNA synthesizer, and purified by standard methods ($N_{40}$ denotes a random sequence of 40 nucleotides built uniquely into each aptamer). Approximately $10^{15}$ DNA molecules with unique sequences from the template pool can be PCR amplified using the primers YW.42.30.A 5'-TAATACGACTCACTATAGGGAGACAA-GAATAAACGCTCAA-3' (SEQ ID NO:3) and YW.42.30B 5'-GCCTGTTGTGAGCCTCCTGTCGAA-3' (SEQ ID NO:4).

A second pool, "a semi-structured" pool, uses a DNA template with the following sequence: 5'-GGAGCCTTCCTC-CGGA-3' (SEQ ID NO:5)-($N_{40}$)-5'-TCCGGTTTC-CCGAGCTT-3' (SEQ ID NO:6), is synthesized in the same manner. Approximately $10^{15}$ DNA molecules with unique sequences from the template pool can be PCR amplified using the primers jd6093a 5'-TAATACGACTCACTATAGGAGC-CTTCCTCCGGA-3' (SEQ ID NO:7) and jd6093b 5'-AAGCTCGGGAAACCGGA-3' (SEQ ID NO:8). Amplified pool PCR product is precipitated with ethanol, re-suspended in water and desalted on a Nap-5 column (Pharmacia). Approximately $4 \times 10^{15}$ DNA molecules from each of the pool PCR amplifications are transcribed in vitro using a mutant Y639F T7 RNA polymerase which accepts 2'-fluoropyrimidines (Sousa, 1999), 2'-fluoropyrimidine and 2'-OH purine NTPs, to yield ~$3 \times 10^{16}$ RNA molecules with corresponding sequences. Stabilized 2'-fluoro-pyrimidine pools made up of $10^{14}$-$10^{15}$ random sequences in a total volume of approximately 100 μl are contacted with either biotinylated target immobilized in neutravidin coated plates (Pierce) or adherent target-expressing cells immobilized in plates. A typical binding buffer used for the positive and negative selection steps contains 20 mM HEPES, pH 7.4, 150 mM NaCl, 10 mM $MgCl_2$, 1 mM EDTA, 1 mM DTT, and 0.1 mg/ml tRNA (4 mM). Following a 10 min. negative incubation step at room temperature, RNAs which bind to the target alone are removed in this negative selection step. The solution containing unbound RNA is then transferred to another identical well containing immobilized target and effector is added to the solution. The concentration of effector added can be adjusted to ultimately enrich molecules which respond to effector at the most appropriate concentration. Initially the effector is provided at saturating concentrations (typically millimolar for small molecule effectors such as glucose and high micromolar concentration for protein effectors) to ensure that molecules with any measure of effector dependence are isolated. In successive rounds of selection, the effector concentration can be reduced to preferentially isolate the most effector-dependent molecules. Following an equilibration period of 1 hour, wells are rinsed with excess binding buffer (typically washing four times with 120 μl of 1×ASB on a robotic plate washer with 30 sec. shakes). 50 μl of RT mix (RT primer, 4 μM; 5× "Thermo buffer", 1×; DTT, 100 mM; mixed dNTPs, 0.2 mM each; vanadate nucleotide inhibitor 200 μM; tRNA 10 μg/ml; 0.5 μl Invitrogen Thermoscript Reverse Transcriptase; brought to 50 μl with water) is added to the selection well and incubated at 65° C. for 30 min with tape over wells to reduce evaporation.

The RT reaction is diluted 10-fold into a 100 μl PCR reaction (containing 5'-primer, 1 μM; 3'-primer, 1 μM; 10× Invitrogen supplied PCR buffer (no Mg), 1×; dNTPs, 0.2 mM each; $MgCl_2$, 3 mM; 1 μl Invitrogen Taq; 10 μl incubated RT reaction and brought to 100 μl with water) and thermocycled with the following schedule: 94° C., 1 min; 62° C., 1 min; 72° C. 3 min. The PCR reactions are assayed at 10 cycles by agarose gel, and then each successive 5 cycles until defined amplification bands are visible via ethidium bromide staining. Completed PCR reactions are purified using a Centri-sep column and diluted 10-fold into a 50 μl transcription reaction (4×TK Transcription buffer, 1×; $MgCl_2$, 25 mM; NTPs 5 mM each; NEB T7 RNA polymerase 2 μl; water to 50 μl). The transcription reaction is incubated overnight at 37° C. and the resulting transcription products are purified by denaturing polyacrylamide gel electrophoresis (10% gel).

The entire selection process is repeated until the fraction of molecules surviving both positive and negative selection increases significantly above the original naïve pool fraction, typically >10% of the input. Typically >10 cycles of selection are required for enrichment. Individual molecules within the enriched pool are isolated and characterized by subcloning the pooled template DNA using the TOPO TA cloning system (Invitrogen). Individual clones are sequenced and unique clones screened for effector dependent binding.

Method (2): Pre-Selection for Target Binding Followed by Effector-Dependent Selection.

Selection method (1) can be modified as follows if the probability that molecules with both target and effector binding properties exist in the starting pool is low. Instead of selecting initially for both target binding and effector dependence, in vitro selection can be used to isolate molecules with high affinity for the target. Following an optional diversification step (wherein the selected pool of target-binding sequences is partially randomized), effector-dependent selection can be applied. To isolate target specific aptamers, the previously described selection method is applied with the following modifications: (1) target is omitted from the negative selection step, and (2) effector is omitted from the positive selection step. 5-15 rounds of selection will typically yield a pool of target binding species containing 1-1000 unique sequences. Individual clones are screened for the ability to specifically bind to the target.

A diversified pool of sequences with increased likelihood of effector-dependent target binding activity can be generated by a number of means including the following:

1) mutagenic PCR amplification of the enriched target-binding pool of sequences.
2) doped resynthesis of individual clone sequence(s) isolated from the target-binding pool, selecting clones that have high affinity and specificity binding. In this case, mutations are introduced at random across the sequence with 10-30% probability at each position or within specified regions of the sequence.
3) resynthesis of a functionally important subdomain of individual clone sequence(s) isolated from the target-binding pool, flanked by random-sequence domains. Once individual aptamers are identified from the original pool, the minimal sequence element required for the biochemical activity can be identified through two parallel approaches: (1) truncation analysis by limited alkaline hydrolysis, and (2) doped reselection (methods are reviewed in Fitzwater & Polisky, 1996). In addition to helping to determine the minimal functional aptamer element, sequence variation introduced via doped reselection can provide mutants of the original clone with improved affinity or biochemical activity. The diversified pool is subjected to selection for effector-dependent target binding as described previously.

Method (3): Pre-Selection for Effector Binding Followed by Effector-Dependent Target Binding Selection.

Selection method (1) can be modified as follows if the probability that molecules with both target and effector binding properties exist in the starting pool is low. Instead of selecting initially for both target binding and effector dependence, in vitro selection can be used to isolate molecules with high affinity for the effector. Following an optional diversification step (wherein the selected pool of effector-binding sequences is partially randomized), effector-dependent, target-binding selection can be applied as described previously. To isolate effector-specific aptamers, the first selection method is applied with the following modifications: (1) target is omitted from the negative selection step, and (2) target is omitted from the positive selection step and instead effector is immobilized to the capture solid support. In the case of small molecule effectors such as glucose, conventional affinity chromatography using 200 µl agarose bead columns with 1-5 mM immobilized effector is the preferred immobilization format. 5-15 rounds of selection will typically yield a pool of effector binding species containing 1-1000 unique sequences. Individual clones are screened for the ability to specifically bind to the effector.

A sequence-diversified pool of effector-binding molecules can be generated by one of the following methods:
1) mutagenic PCR amplification of the enriched effector-binding pool of sequences,
2) doped resynthesis of individual clone sequence(s) isolated from the effector-binding pool, selecting clones that have high affinity and specificity binding. In this case, mutations are introduced at random across the sequence with 10-30% probability at each position or within specified regions of the sequence.
3) resynthesis of a functionally important subdomain of individual clone sequence(s) isolated from the effector-binding pool, flanked by random-sequence domains. The functionally important subdomain of the effector-binding sequences can be defined by truncation of the original clones, following by assays for effector binding.

The diversified pool is subjected to selection for effector-dependent target binding as described in selection method (1).

Method (4): Pre-Selection for Effector Binding and Target Binding Motifs, Followed by Effector-Dependent Target Binding Selection.

Selection method (1) can be modified as follows if the probability that molecules with both target and effector binding properties exist in the starting pool is low. Instead of selecting initially for both target binding and effector dependence, in vitro selection can be used to isolate two separate pools of molecules, one with high affinity for the effector and the other with high affinity for the target. Subdomains within the two pools can be engineered to create a chimeric pool of molecules in which each molecule contains one copy of an effector-binding motif and one copy of a target binding motif. This chimeric pool is then subjected to effector-dependent, target-binding selection as described previously.

To isolate target specific aptamers, selection method (1) is applied with the following modifications: (1) target is omitted from the negative selection step, and (2) effector is omitted from the positive selection step. To isolate effector-specific aptamers, the selection method (1) is applied with the following modifications: (1) target is omitted from the negative selection step, and (2) target is omitted from the positive selection step and instead effector is immobilized to the capture solid support. In the case of small molecule effectors such as glucose, conventional affinity chromatography using 200 µl agarose bead columns with 1-5 mM immobilized effector is the preferred immobilization format.

In the preferred embodiment, functional subdomains of high affinity clones from each of the target- and effector-specific pools are used to create the chimeric pool for effector-dependent selection. The functional subdomains can be identified as described previously (selection method (2)). The chimeric pool can be generated by linearly concatenating the functional motifs together with an intervening random sequence domain. Alternatively, the motifs can be combined at the secondary structure level by coupling via linking helices as described previously for effector-dependent ribozymes (Soukup, G., and Breaker, R. (1999) "Design of allosteric hammerhead ribozymes activated by ligand-induced structure stabilization." Structure Fold Des 7 (7): 783-91).

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described above. In the case of conflict, the present Specification, including definitions, will control. In addition, the materials, methods, and examples are illustrative only and not intended to be limiting.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Identifying Aptamers with Binding Specificity to gp120

Figure 4:
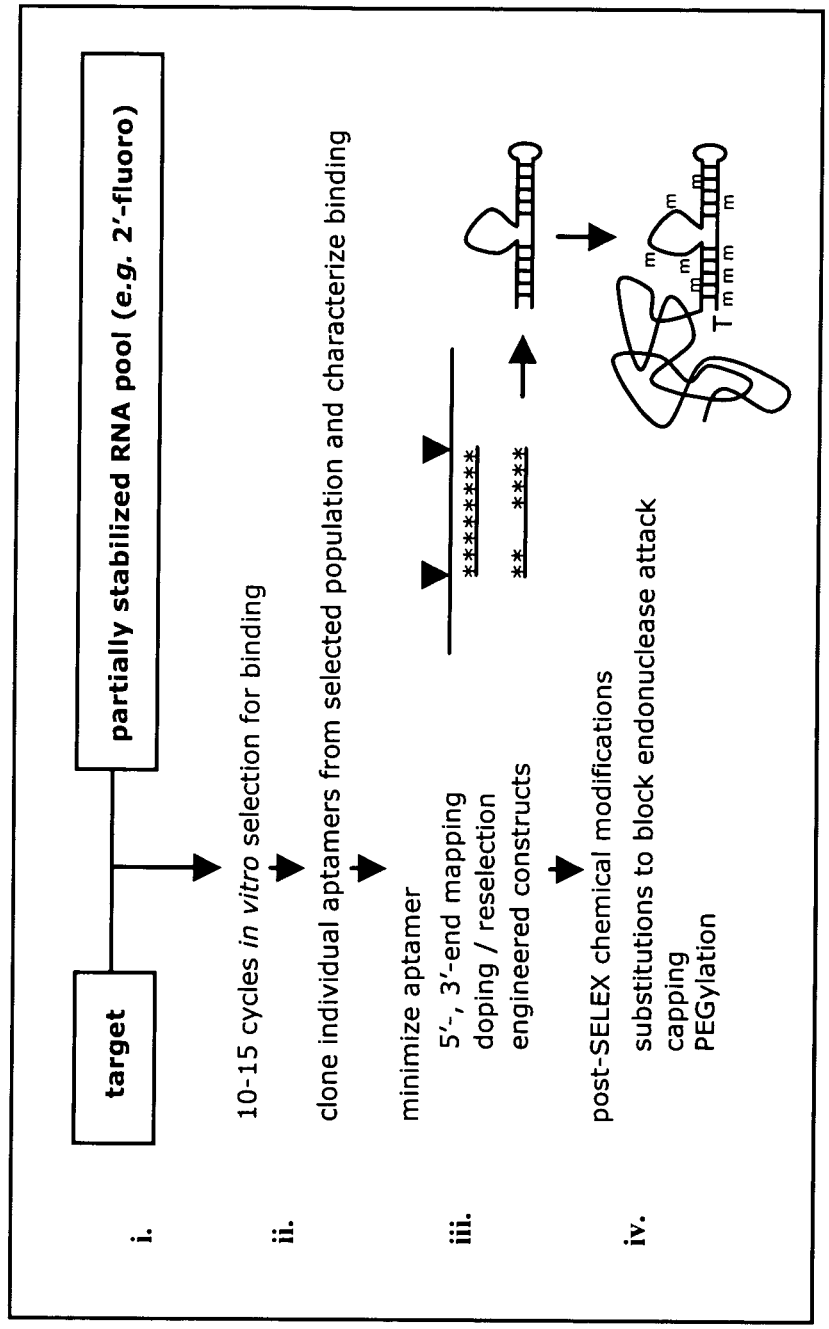
FIG. 4 shows a schematic of the steps typically required to generate an aptamer.

FIG. 4 shows the steps typically required to generate an aptamer for therapeutic purposes. The process can be approximately considered in four phases: (i) and (ii) aptamer identification, (iii) aptamer minimization, and (iv) aptamer optimization for stability.

Stabilized 2'-fluoro-pyrimidine pools made up of $10^{14}$-$10^{15}$ random sequences were contacted with a biotinylated sulfotyrosine-CCR5 peptide (Cormier et al., 2000) immobilized in neutravidin coated 96-well plates (Pierce). Alternatively, adherent CCR5 expressing cells immobilized in 96-well plates can be used. RNAs which bind to the peptide or cells alone were removed in this negative selection step. The RNA solution was then transferred to another identical CCR5 peptide. Alternatively, a cell containing well can be used. At this point gp120 was added to the reactions and they were allowed to equilibrate. Wells were then rinsed with selection buffer and immobilized RNA amplified by reverse transcription, PCR and transcription for another round of activity-based selection. Aptamers selected in this manner both bind to gp120 and induce gp120 binding to CCR5, thus exposing the CCR5 or CD4i epitope. The aptamers generated by activity-based selection may bind to the CD4 binding site, but this is not absolutely required, as the aptamer may use an alternative mechanism to stabilize gp120 in the CCR5 binding conformation. Since an initial negative selection step was used, aptamers which bind to CCR5 and gp120 simultaneously in a non-allosteric manner should not have been selected. During the post-selection process, pools and clones were screened appropriately to insure that they do not have any CCR5 binding activity in the absence of gp120. A more detailed description of the selection process is provided below.

Pool preparation. Selection for gp120 aptamers was performed with two different nucleic acid pools containing 2'-fluoropyrimidines for additional serum stability. For the first pool, a DNA template with the sequence: 5'-GCCTGT-TGTGAGCCTCCTGTCGAA-3' (SEQ ID NO:1), linked by 40 randomized nucleotides-($N_{40}$)—to 5'-TTGAGCGTTTAT-TCTTGTCTCCCTATAGTGAGTCGTATTA-3'(SEQ ID NO:2), was synthesized using an ABI EXPEDITE™ DNA synthesizer, and purified by standard methods ($N_{40}$ denotes a random sequence of 40 nucleotides built uniquely into each aptamer). Approximately $10^{15}$ DNA molecules with unique sequences from the template pool were PCR amplified the primers YW.42.30.A, 5'-TAATACGACTCACTATAGG-GAGACAAGAATAAACGCTCAA-3' [SEQ ID No.3] and YW.42.30B, 5'-GCCTGTTGTGAGCCTCCTGTCGAA-3' [SEQ ID No.4]. For the second pool, a "semi-structured" pool, the DNA template sequence 5'-GGAGCCTTCCTC-CGGA-3' (SEQ ID NO:5)—($N_{40}$)-5'-TCCGGTTTC-CCGAGCTT-3' [SEQ ID No.6] was synthesized in the same manner. Approximately $10^{15}$ DNA molecules with unique sequences from the second template pool were PCR amplified using the primers jd6093a 5'-TAATACGACTCACTAT-AGGAGCCTTCCTCCGGA-3' [SEQ ID No.7] and jd6093b 5'-AAGCTCGGGAAACCGGA-3'[SEQ ID No. 8]. Amplified pool PCR product was precipitated with ethanol, re-suspended in water and desalted on a Nap-5 column (Pharmacia). Approximately $4 \times 10^{15}$ DNA molecules from the pool PCR amplification were transcribed in vitro using a mutant Y639F T7 RNA polymerase which accepts 2'-fluoropyrimidines, 2'-fluoropyrimidine and 2'-OH purine NTPs, to yield $\sim 3 \times 10^{16}$ RNA molecules with corresponding sequences.

Initial selection experiments. HIV-1 gp120 BaL was the target for use in selections. This strain of gp120 uses CCR5 as its co-receptor and thus is more likely to represent a clinically relevant strain of gp120 for prophylactic vaccine development than a lab-adapted, CXCR4 co-receptor using strain such as HXB2. Purified recombinant gp120 BaL expressed in CHO cells was obtained from Advanced Bioscience Laboratories (Gaithersburg, Md.).

Figure 5:
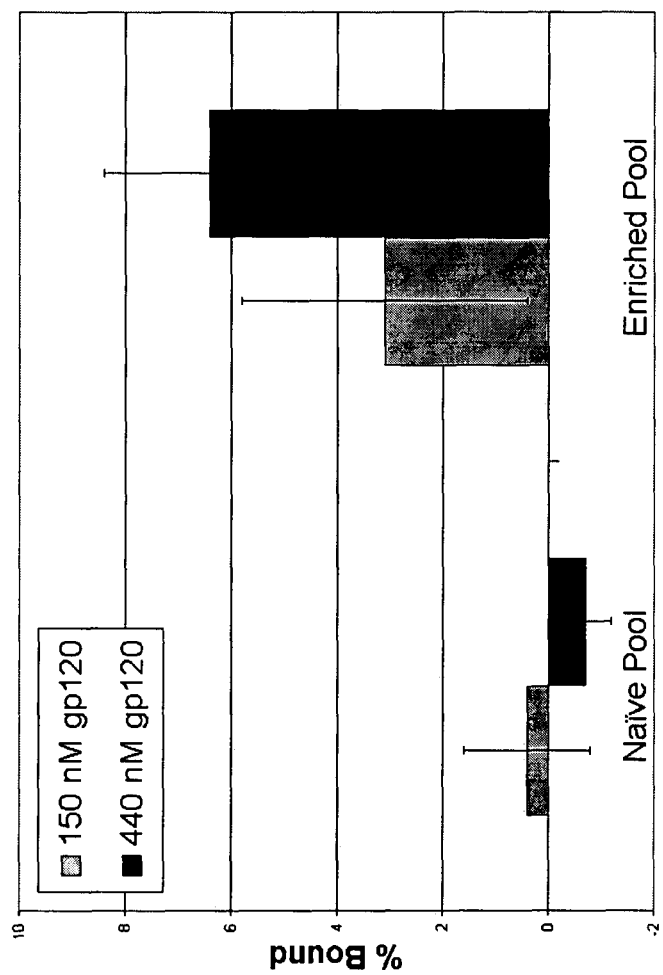
FIG. 5 shows gp120 BaL specific binding was detectible when compared with control in a nitrocellulose binding assay.

An initial experiment was done using the nitrocellulose filter partitioning method (Tuerk and Gold, 1990; Conrad et al., 1996) to enrich for aptamers that bind to gp120 BaL. Initially, $2 \times 10^{14}$ unique sequences were equilibrated with 50-100 nM gp120 BaL in selection buffer (20 mM K-Hepes pH 7.4, 120 mM NaCl, 1 mM $MgCl_2$, 1 mM $CaCl_2$, 5 mM KCl) at room temperature for 1 hour. Complexed and free RNA molecules were separated using 0.2 micron nitrocellulose filter disks (Tuerk and Gold, 1990; Conrad et al., 1996). RNA/gp120 BaL complexes were expected to be retained on the nitrocellulose membrane, while unbound RNA would pass through. RNA was eluted from the nitrocellulose membrane by submerging the membrane in 7 M urea, 100 mM sodium acetate, 3 mM EDTA and heating to 90° C. for 5 minutes. The elution process was repeated twice, followed by extraction of the eluate with phenol and ethanol precipitation of the eluted RNA. After annealing to the 3' primer YW.42.30B, the RNA was amplified by reverse transcription at 50° C. for 30 minutes (Thermoscript™ RT, Invitrogen) followed by PCR under standard conditions (Taq polymerase, Invitrogen) using the primers YW.42.30B and YW.42.30A, yielding the corresponding DNA templates for the second round of selection. Subsequent rounds of selection were conducted using a similar procedure, except that the pooled RNA was passed through a nitrocellulose filter prior to incubation with gp120 to remove molecules that bound to nitrocellulose. After 8 rounds of selection, gp120 BaL specific binding was detectable when compared with naïve pool in a standard nitrocellulose filter binding assay (FIG. 5) using 5'-$^{32}$P labeled RNA pool. While the extent of binding was low, the goal of this initial step was not to drive selection to generate the highest affinity aptamers, but merely to demonstrate that a naïve pool could be enriched for gp120 BaL binding.

Activity-based selection for anti-gp120 aptamers that promote gp120 binding to CCR5. Once a naïve pool for gp120 BaL binding was successfully enriched, an agonist (or activity) based selection strategy (agonist SELEX™, an aptamer selection process) was performed. Selection was initiated by equilibration of $4 \times 10^{14}$-$4 \times 10^{15}$ naïve RNA pool molecules with a biotinylated sulfotyrosine-CCR5 peptide of the sequence: $NH_2$-DYQVSSPI($SO_3$)YDIN($SO_3$)YYTSEG-AGK-biotin-$NH_2$ (SEQ ID NO:226) (Cormier et al., 2000) (synthesized and purified by SynPep (Dublin, Calif.)) immobilized in a Neutravidin coated 96 well plate (Pierce) in a 100 µl binding reaction in selection buffer, to remove RNA molecules capable of binding to the CCR5 peptide only. After equilibration with peptide alone, the RNA solution was transferred to a fresh well containing immobilized CCR5 peptide. To this second well, gp120 BaL was added to a final concentration of from 50-100 nM and the RNA/gp 120 solution was allowed to equilibrate with immobilized peptide for 1 hour at room temp. The solution was then removed from the well and discarded. The well was then washed 4-8 times with 200 µl of selection buffer and the washes were also discarded. Peptide bound gp120/RNA complexes were simultaneously eluted and reverse transcribed directly from the well at 65° C. for 30 minutes (Thermoscript™ RT, Invitrogen) followed by PCR under standard conditions (Taq polymerase, Invitrogen) using the primers YW.42.30B and YW.42.30A, and transcription of amplified DNA for the subsequent round of selection.

Figure 6:
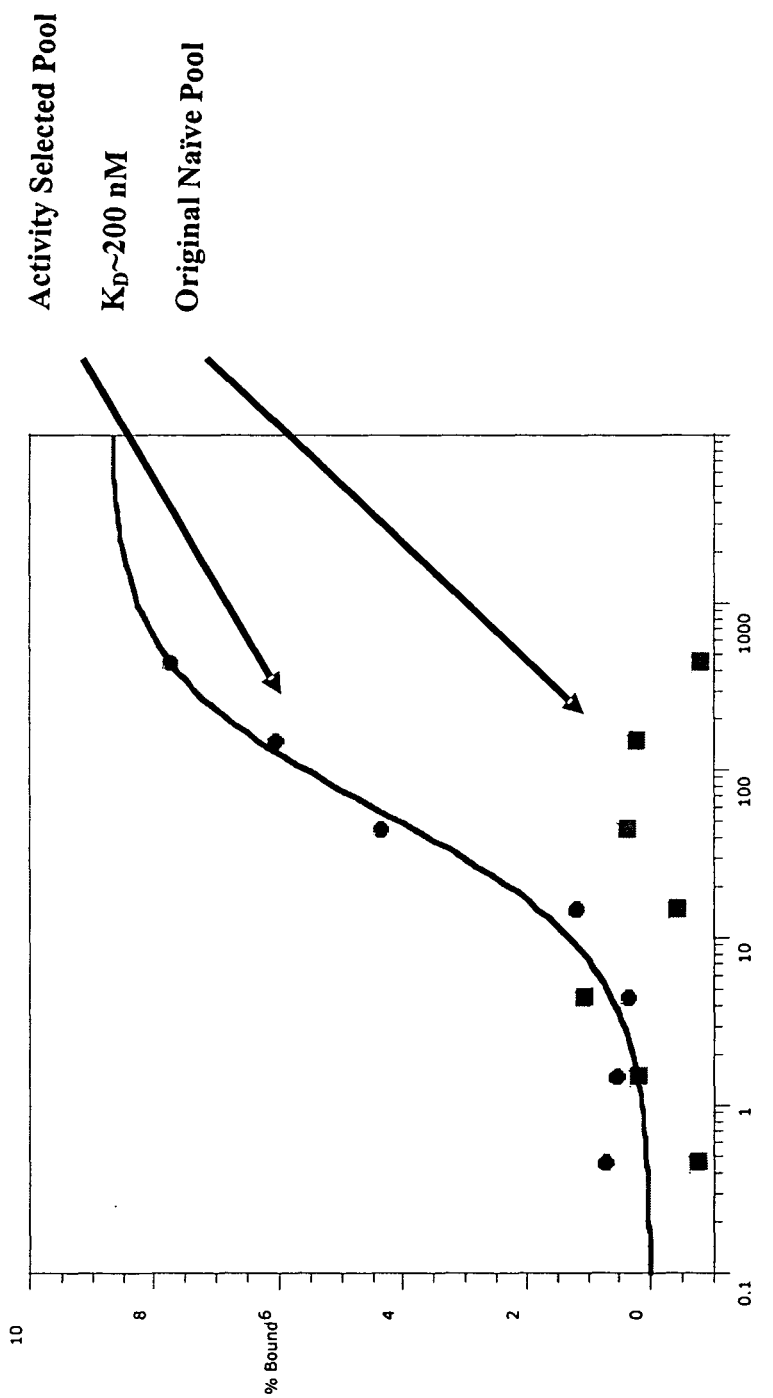
FIG. 6 shows results from a nitrocellulose filter binding assay showing binding affinity of aptamers to gp120 BaL.
Figure 7:
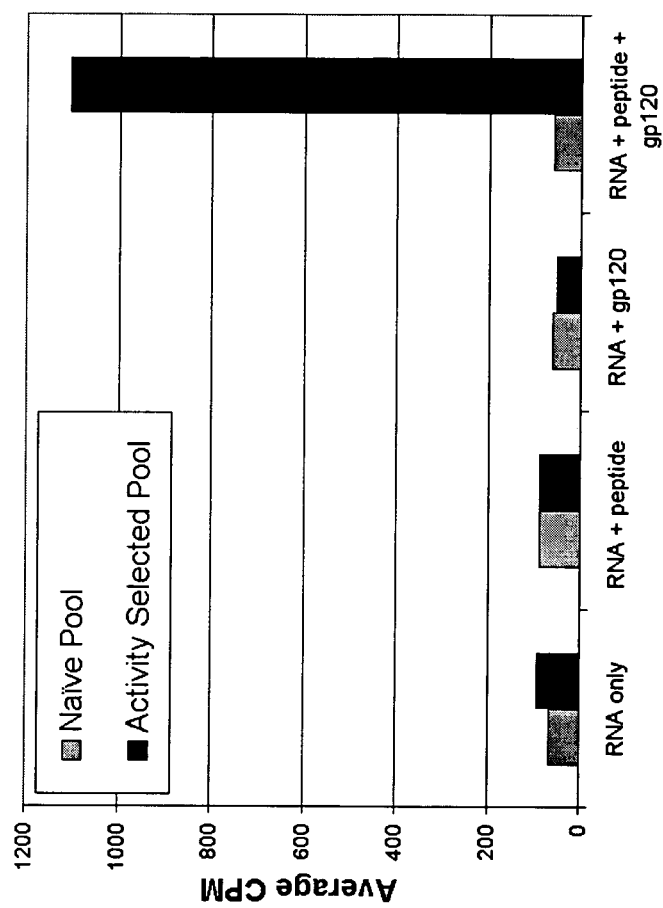
FIG. 7 shows results from a plate binding assay experiment using 5'-$^{32}$P labeled activity selected pool (or naïve pool as a negative control) under standard selection conditions. The plot shows the counts remaining in neutravidin coated plates as a function of the presence of CCR5 peptide, gp120 BaL, both or neither component.

After 13 rounds of activity-based selection, the pool was tested for the ability to bind to gp120 BaL. Successfully selected RNA molecules must have the ability to bind to gp120. As shown (FIG. 6), the 5'-$^{32}$P labeled RNA pool that only went through activity-based selection now binds to gp120 BaL with moderate affinity, $K_D$~200 nM in a nitrocellulose filter binding assay, while the original unselected naïve pool does not bind at all. As additional controls, ELISA assays have shown that gp120 BaL alone did not bind to neutravidin coated plates in either the presence or absence of the CCR5-peptide, and that the activity selected pool did not bind to neutravidin or to CCR5-peptide/neutravidin complexes in the filter binding assay. These results suggest that components of the activity selected pool do in fact have the ability to mimic the action of CD4 on gp120.

In order to further test the ability of the activity selected pool to mimic the action of CD4 on gp120, a plate binding experiment was performed using 5'-$^{32}$P labeled activity selected pool (or naïve pool as a negative control) under standard selection conditions (described above). This experiment measured the counts remaining in neutravidin coated plates as a function of the presence of CCR5 peptide, gp120 BaL, both or neither component. These results (FIG. 7) further suggest that the ability of labeled RNA to bind in a well is dependent on activity selection, CCR5 peptide and gp120 BaL, and thus that aptamers able to mimic the action of CD4 upon gp120 BaL have been enriched in the pool of molecules. In other tests using this same assay, inconsistent results were obtained likely because of the low sensitivity of the assay. To clarify the results, additional assays such as those described in Examples 4 to 7 are performed.

Clones from the activity-based selections were screened. Two dominant clones from the N40 pool activity-only based selections have gp120 BaL specific binding. They are:

```
>SEQ ID No: 9: PLATE#713.E09.M13F
GGGAGACAAGAATAAACGCTCAATTGGGTGACCGACAATTATGGGAGTCA
GCTTGTTGAGAGTTGGACAGGGGGCTGACAACAGGC

>SEQ ID No: 10: PLATE#713.D09.M13F
GGGAGACAAGAATAAACGCTCAATAGGGTGACCGACAATAATGGGAGTCA
AACTGTTGTGTGTTCGACAGGAGGCTCACAACAGGC
```

The sequences of SEQ ID No.11 through SEQ ID No.28 were generated from R8 of the anti-gp120 BaL filter binding selection with N40 pool (no activity based selection yet).

```
>SEQ ID No. 11: gp1208DA_82-D4
GGGAGACAAGAATAAACGCTCAACTGTCGTATTATTTTTAGCGGTCTCAA
CTAATTGTGGCTTTTTCGACAGGAGGCTCACAACAGGC

>SEQ ID NO. 12: gp1208DA_82-C5
GGGAGACAAGAATAAACGCTCAACTGTCGTATTATTTTTTAGCGGTCTCAA
CTAGNTGTGGCTTTTTCGACAGGAGGCTCACAACAGGC

>SEQ ID NO. 13: gp1208DA_82-E2
GGGAGACAAGAATAAACCCTCAACCTTCGCGTTTTGTCAAAGTATTTTTG
AAGGAATTGTGACTTCGACAGGAGGCTCACAACAGGC

>SEQ ID NO. 14: gp1208DA_82-A3
GGGAGACAAGAATNANCNCTCAACCTTCGCGTTTTGTCAAAGTATTTTTG
AAGGAATTGTGACTTCGACAGGAGGCTCACAACAGGC

>SEQ ID NO. 15: gp1208DA_82-F4
GGGAGACAAGAATAAACGCTCAACTGTCGTATTATTTTTAGCGGTCTCAA
CTAANNGTNGCTTTTTCGACAGGAGGCTCACAACAGGC

>SEQ ID NO. 16: gp1208DA_82-C4
GGGAGACAAGAATNAACGCTCAACCTTCGCGTTTTGTCAAAGTATTTTTG
AAGGAATTGTGACTTCNACAGGAGGCTCACAACAGGN

>SEQ ID NO. 17: gp1208DA_82-C1
GGGAGACAAGAATNNACCCTCAACTGTCGNATTATTTTCAGCGGNCTCAA
CTAATTGTGGCTTTTTCGACAGGAGGCTCACAACAGGN
```

-continued

```
>SEQ ID NO. 18: gp1208DA_82-C3
GGGAGACAAGAATAAACGCTCAACCTTCGCGTTTTGTCAAAGTATTTTTG
AAGGNANNNTGACTTGGACAGGAGGCTCACAACAGGC

>SEQ ID NO. 19: gp1208DA_82-B5
GGGAGACAAGAATAAACGCTCAACTGTCGTATTATTTTTAGCGGTCTCAA
CTAANNNGTNAGTTTTTCGAGAGGAGGCTCAGAACAGGC

>SEQ ID NO. 20: gp1208DA_82-A1
GGGAGACAAGAATAAACGCTCAACCTTCGCGNTTNGTCAAAGTATTTNNG
ANGGAAAAGNGANTTNGACAGGAGGCTGNCAACAGGC

>SEQ ID NO.21: gp1208DA_82-E1
GGGAGACAAGAATAAACGCTCAACGTACTGGTTATTCCTGGTTAGCGTAA
AGTAGTAAGTGAGTTCGAGAGGAGGCTCACAAGAGGC

>SEQ ID NO. 22: gp1208DA_82-C2
GGGAGACAAGAATAAACGCTCAAGTAAGATAGCAGGTTATAGAGGCAGAA
CANAATGTGAGTTTTCGACAGGAGGCTCACAACAGGC

>SEQ ID NO. 23: gp1208DA_82-G4
GGGAGACAAGAATAAACGCTCAACTGAGTGAGGAAATGNGGGAGCATCTT
ACGGGGANAATTGTTGGACAGGAGGCTCACAACAGGC

>SEQ ID NO. 24: gp1208DA_82-H5
GGGAGACAAGAATAAACGCTCAATAAGAGGTTAAAGTGAGACAGNCTAAT
TAGATGGGAANTAGTTGGACAGGAGGCTCAGAACAGGC

>SEQ ID NO. 25: gp1208DA_82-A5
GGGAGACAAGAATAAAGGCTCAATGGGAGGTGAGCGTAGATGGGGATATT
ATGCGTTGCGTGATTCGACAGGAGGCTCACAACAGGC

>SEQ ID NO. 26: gp1208DA_82-D1
GGGAGACAAGAATNNACCCTCAACTTATCTGAGGAAATACGGATCTTATT
GCATTTAGCGACGTTCGACAGGAGGCTCACAACAGGC

>SEQ ID NO. 27: gp1208DA_82-E3
GGGAGACAAGAATNANCGCTCAAGATTTGACACACAGTAAAAAATAGTAC
AGTAAGTGAGTGCCTTCGACAGGAGGCTCACAACAGGC

>SEQ ID NO.28: gp1208DA_82-A4
GGGAGACAAGAATAANCGCTCAAAGTTTCNANTNACCTGNNNTTANTCNT
NCATGTGCNATCTTTCGAGAGGAGGCTCACAACAGGC
```

The sequences of SEQ ID No.29 through SEQ ID No.36 were generated from R8 of the anti-gp120 BaL filter binding selection with SS pool (no activity based selection yet).

```
>SEQ ID NO. 29: gp1208DE_82-A8
GGANCCTTCCTCCGGAGGTNTTNATATTNCATTACAAGGGGNAAANNTCT
TTTGGNTCCGGTTTCCCGANCTT

>SEQ ID NO. 30: gp1208DE_82-E8
GGAGCCTTCCTCCGGACTTACAGCACAANTTAAATTTACGGGNAANCTCG
TCCCCGTCCGGTTTCCCGAGCTT

>SEQ ID NO. 31: gp1208DE_82-A7
GGAGCCTTCCTCNGGCNCTTGTGTGTTAAAATTTTATTGCGCTTTTTTG
TTTCTCGTCCGGTTTCCCGAGCTA

>SEQ ID NO. 32: gp1208DE_82-D7
GGAGCCTTCCTCCGGATCGTGATCATTTTCTCCAATGATTATACGTTTAT
TTACTGTCCGGTTTCCCGAGCTT

>SEQ ID NO. 33: gp1208DE_82-F7
AGCCTTCCTCCGGAAATTATTANCGNTTCTATTAGACGGNNAANGCGTTT
TAGGTCCGGTTTCCCGAGCTT

>SEQ ID NO. 34: gp1208DE_82-C8
GGAGCCTTCCTCCGGACGGGATAAATAAAATACATAGTANGNNAACAGGG
TGTTGGTCCGGTTTCCCGAGCTT

>SEQ ID NO. 35: gp1208DE_82-F8
GGAGCCTTCCTCCGGAAATCGGCATANTNNACAGTCATANGGNANNTGTT
CTCCCATCCGGTTTCCCGAGCTT
```

>SEQ ID NO. 36: gp1208DE_82-C7
GGAGCCTTCCTCCGGACCACTATTTCGTATCGGCTTTATATATATCCGAT
TGCGCGTCCGGTTTCCCGAGCTT The sequences of SEQ ID No. 37 through SEQ ID No. 67 were generated from R8 of the anti-gp120 BaL filter binding selection with N40 pool and then through 10 rounds of the activity based selection with the CCR5 peptide included.

>SEQ ID NO. 37: PLATE#910.C10.M13F
GGGAGACAAGAATAAACGCTCAATCCTGTAGAGTTTTT-ATTCGGTTGAT
GGGCACTGTTTTTT-ATTCGACAGGAGGCTCACAACAGGC-

>SEQ ID NO. 38: PLATE#910.B11.M13F
GGGAGACAAGAATAAACGCTCAATCCTGTAGAGTTTTT-ATTCGGTTGAT
GGGCACTGTTTTTT-ATTCGAGAGGAGGCTCAGAACAGGC-

>SEQ ID NO. 39: PLATE#910.C12.M13F
GGGAGACAAGAATAAACGCTCAATCCTGTAGAGTTCTT-ATTCGGTTGAT
GGGCACTGTTTTTTT-ATTCGAGAGGAGGCTCACAACAGGC-

>SEQ ID NO. 40: PLATE#910.H12.MI3F
GGGAGACAAGAATAAACGCTCAATGCTGTAGAGTTTTT-ATTCGGTTGAT
GGGGACTGTTTTTT-ATTCGACAGGAGGCTCACAACAGGC-

>SEQ ID NO. 41: PLATE#910.H11.M13F
GGGAGACAAGAATAAACGCTCAATCCTGTAGAGTTTTT-ATTTCGGTTGAT
GGGCAGTGTTTTTTTATTGGACAGGAGGCTCACAACAGGC

>SEQ ID NO. 42: PLATE#910.F12.M13F
GGGAGACAAGAATAAACGCTCAAGCCTGTGGAGTTTTT-ATTCGGTTGAT
GGGCACTGTTTTTT-ATTCGACAGGAGGCTCACAACAGGC-

>SEQ ID NO. 43: PLATE#910.F11.M13F
GGGAGACAAGAATAAACGGTCAAGCCTGTAGAGTTTTT-ATTCGGTTGAT
GGGCACTGTTTTTT-ATTGGACAGGAGGCTCACAAGAGGC-

>SEQ ID NO. 44: PLATE#910.A10.M13F
GGGAGACAAGAATAAACGCTCAATCCTGTAGAGCTTTT-ATTCGGTTGAT
GAGCACTGTTTTTT-ATTCGACAGGAGGCTCACAACAGGC-

>SEQ ID NO. 45: PLATE#910.D10.M13F
GGGAGACAAGAATAAACGCTCAATCGTGTAGAGCTTTT-ATTCGGTTGAT
GAGCACTGTTTTTT-ATTCGACAGGAGGCTCACAACAGGC-

>SEQ ID NO. 46: PLATE#910.G09.M13F
GGGAGACAAGAATAAACGGTCAAGCCTGTAGAGCTTTT-ATTCGGTTGAT
GGGCACTGTTTTTT-ATTCGACAGGAGGCTCACAACAGGC-

>SEQ ID NO. 47: PLATE#910.D09.M13F
GGGAGACAAGAATAAACGCTCAATCGTGTAGAGTTTTTTATTCGGTTGAT
GGGCACTGTTTTTT-ATTCGACAGGAGGCTCACAACAGGC-

>SEQ ID NO. 48: PLATE#910.F10.M13F
GGGAGACAAGAATAAACGCTCAATCCTGTAGAGTTTTTTATTCGGTTGAT
GGGCACTGTTTTTT-ATTCGACAGGAGGGTCACAACAGGC-

>SEQ ID NO. 49: PLATE#910.C11.M13F
GGGAGACAAGAATAAACGCTCAAGCCTGTAGAGTTTTT-ATTCGGTTGAT
GGGCGGTGTTTTTT-ATTCGACAGGAGGCTCACAACAGGC-

>SEQ ID NO. 50: PLATE#910.D11.M13F
GGGAGACAAGAATAAACGCTCAATAGGGTGACCGAG---AATAATGGGAG
TCAAACTGTTG-TGTGTTCGAGAGGAGGCTCAGAACAGGC-

>SEQ ID NO. 51: PLATE#910.E11.M13F
GGGAGACAAGAATAAACGCTCAATAGGGTGACCGAC---AATAATGGGAG
TCAAACTGTTG-TGTGTTCGACAGGAGGCTCACAACAGGC-

>SEQ ID NO. 52: PLATE#910.E12.M13F
GGGAGACAAGAATAAACGCTCAANAGGGTGACGGAC---AATAATGGGAG
TCAAACTGTTG-TGTGTTCGACAGGAGGCTCACAACAGGC-

>SEQ ID NO. 53: PLATE#910.B12.M13F
GGGAGACAAGAATAAACGCTCAATTGGGTGACCGAC---AATTATGGGAG
TGAGGTTGTTG-AGAGTTCGACAGGAGGCTCACAACAGGC-

>SEQ ID NO. 54: PLATE#910.B10.M13F
GGGAGACAAGAATAAACGCTCAATTGGGTGACCGAC---AATTATGGGAG
TGAGGTTGTTG-AGAGTTCGACAGGAGGCTCACAACAGGC-

>SEQ ID NO. 55: PLATE#910.G10.M13F
GGGAGACAAGAATAAACGCTCAATTGGGTGACCGAC---AATTATGGGAG
TCAGCTTGTTG-AGAGTTCGACAGGAGGCTCACAACAGGC-

>SEQ ID NO. 56: PLATE#910.A11.M13F
GGGAGACAAGAATAAACGCTCAATTGGGTGACCGAC---AATTATGGGAG
TCAGCTTGTTG-AGAGTTCGACAGGAGGCTCACAACAGGC-

>SEQ ID NO. 57: PLATE#910.G11.M13F
GGGAGACAAGAATAAACGCTCAATTGGGTGACCGAC---AATTATGGGAG
TCAGCTTGTTG-AGAGTTCGACAGGAGGCTCACAACAGGC-

>SEQ ID NO. 58: PLATE#910.C09.M13F
GGGAGACAAGAATAAACGCTCAATAGGGTGACCGAC---AATNATGGGAG
TCANNCNGTTGATGTGTTCGACAGGAGGCTCACAACAGGC-

>SEQ ID NO. 59: PLATE#910.E10.M13F
GGGAGACAAGAATAAACGCTCAATGTTGAAGTGTTT---AGTAAGTGAAG
CCGCTGTTTTAGTTTGTTCGACAGGAGGCTCACAACAGGC-

>SEQ ID NO. 60: PLATE#910.E09.M13F
GGGAGACAAGAATAAACGCTCAATAGGGTGACCGAC---AAGATGGGAGT
CCAATTGTTG--TGAGTTCGACAGGAGGCTCACAACAGGC-

>SEQ ID NO.61: PLATE#910.D12.M13F
GGGAGAGAAGAATAAACGCTCAAACA-GTGTAGCTCGTCGATTG-CTAGG
GTGTCCGAGAGAAC-ATTCGACAGGAGGGTCACA-CAGGCA

>SEQ ID NO. 62: PLATE#910.G12.M13F
GGGAGACAAGAATAAACGCTCAAGT--GAGTCTTCCATCGATTTTCTTGG
GTGTCCGACAGAGC-ATTCGACAGGAGGCTCACAACAGGC-

>SEQ ID NO. 63: PLATE#910.H09.M13F
GGGAGACAAGAATAAACGCTCAAAGAGCCGTGATCG---TTATCGAATGG
GTGTGCGACGATTCGTTTCGACAGGAGGCTCACAACAGGC-

>SEQ ID NO. 64: PLATE#910.A09.M13F
GGGAGACAAGAATAAACGCTCAACATAATGTGAA----------------
-------GCTTCGAGAGGAGGCTCAGAACAGGC-

>SEQ ID NO. 65: PLATE#910.B09.M13F
GGGAGACAAGAATAAACGCTCAACATAATGTGAA----------------
-------GCTTGGACAGGAGGCTCAGAAGAGGC-

>SEQ ID NO. 66: PLATE#910.A12.M13F
GGGAGACAAGAATAAACGCTGAAGATAATGTGAA----------------
-------GCTTCGACAGGAGGCTGACAACAGGC-

>SEQ ID NO. 67: PLATE#910.F09.M13F
GGGAGACAAGAATAAACGCTCAACATAATGTGAA----------------
-------GCTTCGACAGGAGGGTCACAACAGGC-

The sequences of SEQ ID No. 68 through SEQ ID No. 115 were generated from R10 of activity selection only with the N40 pool (no pre-enrichment for BaL binders).

>SEQ ID NO. 68: PLATE#710.C05.M13F
-GGGAGACAAGAATAAACGCTCAA-TGGGGTGACCGACACA-ATTATGG-
GAG
TGAG-CTTGTTGAGAGTTCGACAGGAGGGTCACAACAGGC-

>SEQ ID NO. 69: PLATE#710.C06.M13F
-GGGAGACAAGAATAAACGCTCAA-TTGGGTGACCGACAATTATGGGAG
TCAG-CTTGTTGAGAGTTCGACAGGAGGCTCACAACAGGC-

>SEQ ID NO. 70: PLATE#710.E04.M13F
-GGGAGACAAGAATAAACGCTCAA-TTGGGTGACCGAGA-ATTATGGGAG
TCAG-CTTGTTGAGAGTTCGACAGGAGGCTCACAACAGGC-

>SEQ ID NO. 71: PLATE#710.E05.M13F
-AGGAGACAAGAATAAACGCTCAA-TTGGGTGACCGACA-ATTATGGGAG
TCAG-CTTGTTGAGAGTTCGACAGGAGGCTCACAACAGGC-

>SEQ ID NO. 72: PLATE#710.F05.M13F
-GGGAGACAAGAATAAACGCTCAA-TTGGGTGACCGACA-ATTATGGGAG
TCAG-CTTGTTGAGAGTTCGACAGGAGGCTCACAACAGGC-

>SEQ ID NO. 73: PLATE#710.A06.M13F
-GGGAGACAAGAATAAACGCTCAA-TTGGGTGACCGACA-ATTATGGGAG
TCAG-CTTGTTGAGAGTTCGACAGGAGGCTCACAACAGGC-

>SEQ ID NO. 74: PLATE#710.B01.M13F
-GGGAGACAAGAATAAACGCTCAA-TTGGGTGACCGACA-ATTATGGGAG
TCAG-CTTGTTGAGAGTTCGACAGGAGGCTCACAACAGGC-

>SEQ ID NO. 75: PLATE#710.H05.M13F
-GGGAGACAAGAATAAACGCTCAA-TTGGGTGACCGACA-ATTATGGGAG
TCAG-CTTGTTGAGAGTTCGACAGGAGGCTCACAACAGGC-

>SEQ ID NO. 76: PLATE#710.H01.M13F
-GGGAGACAAGAATAAAGGCTCAA-TTGGGTGACCGACA-ATTATGGGAG
TCAG-CTTGTTGAGAGTTCGACAGGAGGGTCACAACAGGC-

>SEQ ID NO. 77: PLATE#710.B04.M13F
-GGGAGACAAGAATAAACGCTCAA-TTGGGTGACCGACA-ATTATGGGAG
TCAG-CTTGTTGAGAGTTCGACAGGAGGCTCACAAGAGGC-

>SEQ ID NO. 78: PLATE#710.B05.M13F
-GGGAGACAAGAATAAAGGCTCAA-TTGGGTGACCGACA-ATTATGGGAG
TCAG-CTTGTTGAGAGTTCGAGAGGAGGCTCACAACAGGC-

>SEQ ID NO. 79: PLATE#710.F03.M13F
-GGGAGACAAGAATAAACGCTCAA-TTGGGTGACCGACA-ATTATGGGAG
TCAG-CTTGTTGAGAGTTCGACAGGAGGCTCACAACAGGC-

>SEQ ID NO. 80: PLATE#710.H06.M13F
-GGGAGAGAAGAATAAAGGCTCAA-TTGGGTGACCGACA-ATTATGGGAG
TCAG-CTTGTTGAGAGTTGGACAGGAGGCTCACAACAGGC-

>SEQ ID NO. 81: PLATE#710.F06.M13F
-GGGAGACAAGAATAAACGCTCAA-TTGGGTGACCGACA-ATTATGGGAG
TCAG-CTTGTTGAGAGTTCGACAGGAGGCTCACAACAGGC-

>SEQ ID NO. 82: PLATE#710.G01.ML3F
-GGGAGACAAGAATAAACGCTCAA-TTGGGTGACCGACA-ATTATGGGAG
TCAG-CTTGTTGAGAGTTCGACAGGAGGCTGACAACAGGC-

>SEQ ID NO. 83: PLATE#710.F04.M13F
-GGGAGACAAGAATAAACGCTGAATAGGG-TGACCGACA-ATAATGGGAG
TCAG-ACTGTTGTGTGTTCGACAGGAGGCTCACAACAGGC-

>SEQ ID NO. 84: PLATE#710.H03.M13F
-GGGAGACAAGAATAAACGGTCAATAGGG-TGACCGACA-ATAATGGGAG
TGAG-ACTGTTGTGTGTTCGACAGGAGGCTCACAACAGGC-

>SEQ ID NO. 85: PLATE#710.G06.M13F
-GGGAGACAAGAATAAACGCTCAATAGGG-TGACCGACA-ATAATGGGAG
TCAA-ACTGTTGTGTGTTCGACAGGAGGCTCACAACAGGC-

>SEQ ID NO. 86: PLATE#710.D05.M13F
-GGGAGACAAGAATAAACGCTCAATAGGG-TGACCGACA-ATAATGGGAG
TCAA-ACTGTTGTGTGTTCGACAGGAGGCTCACAACAGGC-

>SEQ ID NO. 87: PLATE#710.A03.M13F
-GGGAGAGAAGAATAAACGCTCAAATTGGGTGACCGACA-ATTATGGGAG
TCAG-CTTGTTGAGAGTTCGACAGGAGGCTCACAACAGGC-

>SEQ ID NO. 88: PLATE#710.B03.M13F
-GGGAGACAAGAATAAACGGTCAATAGGGGTGACCGACA-ATAATGGGAG
TCAA-ACTGTTGTGTGTTCGACAGGAGGCTCACAACAGGC-

>SEQ ID NO. 89: PLATE#710.A05.M13F
-GGGAGACAAGAATAAACGCTCAATAGGG-TGACCGACA-ATAATGGGAG
TCAA-ACTGTTGTGTGTTGGACAGGAGGCTCACAACAGGC-

>SEQ ID NO. 90: PLATE#710.E01.M13F
-GGGAGACAAGAATAAACGCTCAATAGGG-TGAGCGACA-ATAATGGGAG
TCAA-ACTGTTGTGTGTTCGACAGGAGGCTCAGAACAGGC-

>SEQ ID NO. 91: PLATE#710.D01.M13F
-GGGAGACAAGAATAAACGCTCAATAGGG-GACCGACA-ATAATGGGAG
TGAA-ACTGTTGTGTGTTCGACAGGAGGCTCACAACAGGC-

>SEQ ID NO. 92: PLATE#710.C02.M13F
-GGGAGACAAGAATAAACGCTCAATGGG-TGACCGACA-ATAATGGGAG
TCAA-ACTGTTGTGTGTTCGACAGGAGGCTCACAACAGGC-

>SEQ ID NO. 93: PLATE#710.B06.M13F
-GGGAGACAAGAATAAACGCTCAATGGG-TGACCGACA-ATAATGGGAG
TCAA-AGTGTTGTGTGTTCGACAGGAGGCTCACAACAGGC-

>SEQ ID NO. 94: PLATE#710.D02.M13F
-GGGAGACAAGAATAAACGCTCAATGGG-TGACCGACA-ATAATGGGAG
TCAA-ACTGTTGTGTGTTCGACAGGAGGCTCACAACAGGC-

>SEQ ID NO.95: PLATE#710.F01.M13F
-GGGAGACAAGAATAAACGCTCAA-TTGGGTGACTGACA-ATTATGGGAG
TCAG-CTTGTTGAGAGTTCGACAGGAGGCTCACAACAGGC-

>SEQ ID NO. 96: PLATE#710.E06.M13F
-GGGAGACAAGAATAAACGCTCAATAGGG-TGACCGACA-ATAATGGGAG
TCAA-GCTGTTGTGTGTTCGACAGGAGGCTCACAACAGGC-

>SEQ ID NO. 97: PLATE#710.B02.M13F
-GGGAGACAAGAATAAACGCTCAATAGGG-GACCGACA-ATAATGGGAG
TCAA-GCTGTTGTGTGTTGGACAGGAGGCTCACAACAGGC-

>SEQ ID NO. 98: PLATE#710.G02.M13F
-GGGAGACAAGAATAAACGCTCAA-TTGGGTGACCGACA-ATTATGGGAG
TCAG-CTCGTTGAGAGTTCGACAGGAGGCTCACAACAGGC-

>SEQ ID NO. 99: PLATE#710.H04.M13F
-GGGAGACAAGA ATAAACGGTCAANAGGG-TGACCGACA-ATAATGGGAG
TCAA-AGTGTTGTGTGTTCGACAGGAGGCTCACAACAGGC-

>SEQ ID NO. 100: PLATE#710.H02.M13F
-GGGAGAGAAGAATAAAGGCTCAA-TTGGGTGACCGACA-TTTATGGGAG
TCAG-CTTGTTGAGAGTTCGACAGGAGGCTCACAACAGGC-

>SEQ ID NO. 101: PLATE#710.D03.M13F
-GGGAGACAAGAATAAACGCTCAA-TTGGGTGACCGACA-ATTATGGGAG
TCAG-CTTGT-GAGAGTTCGACAGGAGGCTCACAACAGGC-

>SEQ ID NO. 102: PLATE#710.E03.M13F
-GGGAGACAAGAATAAACGCTCAA-TTGGGTGGCCGACA-ATTATGGGAG
TCAG-CTTGTTGAGAGTTCGACAGGAGGGTCACAACAGGC-

>SEQ ID NO. 103: PLATE#710.F02.M13F
-GGGAGACAAGAATAAAGGCTGAATGGG-TGACCGACA-ATAATGGGAG
TCAA-ACTGTTGTGNGTTCGACAGGAGGCTCACAACAGGC-

>SEQ ID NO. 104: PLATE#710.E02.M13F
-GGGAGACAAGAATAAAGGGTCAA-TTTGGGTGACCGACA-ATTATGGGAG
TCAAACTTGTTGAGAGTTCGACAGGAGGCTCACAACAGGC-

>SEQ ID NO. 105: PLATE#710.G05.M13F
-GGGAGACAAGAATAAACGCTCAATGGG-TGACCGACA-ATAATGGGAG
TCCA-ATTGTTGTGTGTTCGACAGGAGGCTCACAACAGGC-

>SEQ ID NO. 106: PLATE#710.G04.M13F
-GGGAGACAAGAATAAACGCTCAATGGG-TGACCGACA-ATAATGGGAG
TCCA-ATTGTTGTGTGTTCGACAGGAGGCTCACAACAGGC-

>SEQ ID NO. 107: PLATE#710.A04.M13F
-GGGAGACAAGAATAAACGCTCAATGGG-TGACCGACA-ATAATGGGAG
TCCA-ATTGTTGTGTGTTCGACAGGAGGCTGACAACAGGC-

>SEQ ID NO. 108: PLATE#710.C01.M13F
-GGGAGACAAGAATAAACGCTCAATAGGG-TGACGGATA-ATAATGGGAG
TCAA-ACTGTTGTGTGTTCGACAGGAGGCTCACAACAGGC-

>SEQ ID NO. 109: PLATE#710.D06.M13F
AGGGAGACAAGA-TAAACGGTCAATAGGG-TGACCGACA-ATAGTGGGAG
TGAA-ACTGTTGTGTGTTCGACAGGAGGCTGACAACAGGC-

>SEQ ID NO. 110: PLATE#710.A02.M13F
-GGGAGACAAGAATAAACGCTCAACGGGG-TGACCGACA-ATAATGGGAG
TCCA-ATTGTTGTGTGTTCGAGAGGAGGCTCACAAGAGGC-

>SEQ ID NO. 111: PLATE#710.C03.M13F
-GGGAGACAAGAATAAACGCTCAATGGGG-TGACCGACA-ATTATGGGAG
TGTA-AATGTTGTGATTTCGACAGGAGGCTCAGAACAGGC-

>SEQ ID NO. 112: PLATE#710.A01.M13F
-GGGAGACAAGAATAAACGCTCAATTGGG-TGACCGACA-TTTATGGGAG
TCCA-ATCGTTGTGAATTCGAGAGGAGGCTCACAACAGGC-

>SEQ ID NO. 113: PLATE#710.C04.M13F
-GGGAGACAAGAATAAACGCTCAATCCTGTAGAGTTTTT-ATTCGGTTGA
TGGGCACTGTTTTTTATTCGACAGGAGGCTCACAAGAGGC-

>SEQ ID NO. 114: PLATE#710.D04.M13F
-GGGAGACAAGAATAAACGCTCAATCCTGTAGAGTTTTT-ATTCGGTTGA
TGGGCACTGTTTTTTATTCGACAGGAGGCTCACAACAGGC-

>SEQ ID NO. 115: PLATE#710.G03.M13F
-GGGAGACAAGAATAAACGCTCAATCCTGTAGAGTTTTTTATTCGGTTGA
TGGGCACTGTTTTTTATTCGACAGGAGGCTCACA-CAGGCA

The sequences of SEQ ID No. 116 through SEQ ID No. 161 were generated from R13 of activity selection only with the N40 pool (no pre-enrichment for BaL binders).

>SEQ ID NO. 116: PLATE#713.E09.M13F
GGGAGACAAGAATAAACGCTGAATTGGGTGACCGACAATTATGGGAGTCA
GCTTGTTGAGAGTTCGACAGGGGGCTCACAACAGGGC

>SEQ ID NO. 117: PLATE#713.H07.M13F
GGGAGACAAGAATAAACGCTCAATTGGGTGACCGACAATTATGGGAGTCA
GCTTGTTGAGAGTTCGACAGGAGGCTCACAACAGGC

>SEQ ID NO. 118: PLATE#713.A09.M13F
GGGAGACAAGAATAAACGCTCAATTGGGTGACCGACAATTATGGGAGTCA
GCTTGTTGAGAGTTCGACAGGAGGCTCACAACAGGC

>SEQ ID NO. 119: PLATE#713.A10.M13F
GGGAGACAAGAATAAACGCTCAATTGGGTGACCGACAATTATGGGAGTCA
GCTTGTTGAGAGTTCGACAGGAGGCTCACAACAGGC

>SEQ ID NO. 120: PLATE#713.H10.M13F
GGGAGACAAGAATAAACGCTGAATTGGGTGACCGACAATTATGGGAGTCA
GCTTGTTGAGAGTTCGACAGGAGGCTCACAACAGGC

>SEQ ID NO. 121: PLATE#713.B10.M13F
GGGAGACAAGAATAAACGCTGATTGGGTGACCGACAATTATGGGAGTCA
GCTTGTTGAGAGTTCGACAGGAGGCTCACAAGAGGC

>SEQ ID NO. 122: PLATE#713.D12.M13F
GGGAGACAAGAATAAACGCTCAATTGGGTGACCGACAATTATGGGAGTCA
GCTTGTTGAGAGTTCGACAGGAGGGTCACAACAGGC

>SEQ ID NO. 123: PLATE#713.B12.M13F
GGGAGACAAGAATAAACGCTCAATTGGGTGACCGACAATTATGGGAGTGA
GCTTGTTGAGAGTTCGACAGGAGGCTGACAACAGGC

>SEQ ID NO. 124: PLATE#713.B09.M13F
GGGAGACAAGAATAACGCTCAATTGGGTGACCGACAATTATGGGAGTCA
GCTTGTTGAGAGTTCGACAGGAGGCTCACAACAGGC

>SEQ ID NO. 125: PLATE#713.G12.M13F
GGGAGACAAGAATAAACGCTCAATTGGGTGAGCGACAATTATGGGAGTCA
GGTTGTTGAGAGTTCGAGAGGAGGGTGACAACAGGC

>SEQ ID NO. 126: PLATE#713.F12.M13F
GGGAGAGAAGAATAAACGCTCAATTGGGTGACCGACAATTATGGGAGTCA
GCTTGTTGAGAGTTCGACAGGAGGCTCACAACAGGC

>SEQ ID NO. 127: PLATE#713.G09.M13F
GGGAGACAAGAATAAACGCTCAATTGGGTGACCGAGAATTATGGGAGTCA
GCTTGTTGAGAGTTCGACAGGAGGCTCACAACAGGC

>SEQ ID NO. 128: PLATE#713.E08.M13F
GGGAGACAAGAATAAACGCTCAATTGGGTGACCGACAATTATGGGAGTCA
GCTTGTTGAGAGTTCGACAGGAGGCTCACAACAGGC

>SEQ ID NO. 129: PLATE#713.D10.M13F
GGGAGACAAGAATAAACGCTCAATTGGGTGACCGACAATTATGGGAGTCA
GCTTGTTGAGAGTTCGACAGGAGGCTCAGAACAGGC

>SEQ ID NO. 130: PLATE#713.G10.M13F
GGGAGACAAGAATAAACGCTCAATTTGGGTGACCGACAATTATGGGAGTCA
GCTTGTTGAGAGTTCGACAGGAGGCTCACAACAGGC

>SEQ ID NO. 131: PLATE#713.F10.M13F
GGGAGACAAGAATAAACGCTCAATTGGGTGACCGACAATTATGGGAGTCA
GNTTGTTGAGAGTTCGACAGGAGGCTCACAAGAGGC

>SEQ ID NO. 132: PLATE#713.F08.M13F
GGGAGACAAGAATAAACGCTCAATTGGGTGGCCGACAATTATGGGAGTCA
GCTTGTTGAGAGTTCGACAGGAGGCTCACAACAGGC

>SEQ ID NO. 133: PLATE#713.C10.M13F
GGGAGACAAGAATAAACGCTCAATAGGGTGACCGACAATAATGGGAGTCA
GACTGTTGTGTGTTCGACAGGAGGCTCACAACAGGC

>SEQ ID NO. 134: PLATE#713.B07.M13F
GGGAGACAAGAATAAACGCTCAATTGGGTGACGGACCATTATGGGAGTCA
GCTTGTTGAGAGTTCGACAGGAGGCTCACAACAGGC

>SEQ ID NO. 135: PLATE#713.G11.M13F
GGGAGACAAGAATAAACGCTCAATAGGGTGACCGACAATAATGGGAGTCA
GACTGTTGTGTGTTCGACAGGAGGCTCACAACAGGC

>SEQ ID NO. 136: PLATE#713.G11.M13F
GGGAGACAAGAATAAACGCTCAATAGGGTGACCGACAATAATGGGAGTCA
GACTGTTGTGTGTTCGACAGGAGGCTCACAACAGGC

>SEQ ID NO. 137: PLATE#713.F11.M13F
GGGAGACAAGAATAAAGGCTCAAATGGGTGACCGACAATTATGGGAGTCA
GCTTGTTGAGAGTTCGACAGGAGGCTCACAACAGGC

>SEQ ID NO. 138: PLATE#713.A08.M13F
GGGAGAGAAGAATAAACGCTCAATCGGGTGACCGACAGTTATGGGAGTCA
GCTTGTTGAGAGTTCGACAGGAGGCTCAGAACAGGC

>SEQ ID NO. 139: PLATE#713.D11.M13F
GGGAGACAAGAATAAACGCTCAATCGGGTGACCGACAGTTATGGGAGTCA
GCTTGTTGAGAGTTCGACAGGAGGCTCACAACAGGC

>SEQ ID NO. 140: PLATE#713.D09.M13F
GGGAGACAAGAATAAACGCTCAATAGGGTGACCGACAATAATGGGAGTCA
AACTGTTGTGTGTTCGACAGGAGGCTCACAACAGGC

>SEQ ID NO. 141: PLATE#713.H08.M13F
GGGAGACAAGAATAAACGCTCAATAGGGTGACCGACAATAATGGGAGTCA
AACTGTTGTGTGTTCGACAGGAGGCTGACAACAGGC

>SEQ ID NO. 142: PLATE#713.A12.M13F
GGGAGACAAGAATAAACGCTCAATAGGGTGACCGACAATAATGGGAGTCA
AGCTGTTGTGTGTTCGACAGGAGGCTCACAACAGGC

>SEQ ID NO. 143: PLATE#713.H11.M13F
GGGAGACAAGAATAAACGCTCAATAGGGTGACCGACAATAATGGGAGTCA
AGCTGTTGTGTGTTCGACAGGAGGCTCACAACAGGC

>SEQ ID NO. 144: PLATE#713.E10.M13F
GGGAGACAAGAATAAACGCTCATAGGGTGACCGAGAATAATGGGAGTCA
AGCTGTTGTGTGTTCGAGAGGAGGCTCACAACAGGC

>SEQ ID NO. 145: PLATE#713.B08.M13F
GGGAGACAAGAATAAACGCTCAATAGGGTGACCGAGAATAATGGGAGTCA
AGCTGTTGTGTGTTCGACAGGAGGCTCACAACAGGC

>SEQ ID NO. 146: PLATE#713.H12.M13F
GGGAGACAAGAATAAACGCTCAATAGGGTGACCGACAATAATGGGAGTCA
AGCTGTTGTGTGTTCGACAGGAGGGTCACAACAGGC

>SEQ ID NO. 147: PLATE#713.E12.M13F
GGGAGACAAGAATAAACGCTCAATTGNGTGACCGAGAATAATGGGAGTCA
GACTGTTGTGTGTTCGACAGGAGGCTCACAACAGGC

>SEQ ID NO. 148: PLATE#713.C12.M13F
GGGAGACAAGAATAAACGCTCAATGGGGTGACCGACAATAATGGGAGTCC
AATTGTTGTGTGTTCGACAGGAGGCTCACAACAGGC

>SEQ ID NO. 149: PLATE#713.E07.M13F
GGGAGACAAGAATAAACGCTCAATGGGGTGACCGACAATAATGGGAGTCC
AATTGTTGTGTGTTCGACAGGAGGCTCACAAGAGGC

>SEQ ID NO. 150: PLATE#713.C08.M13F
GGGAGACAAGAATAAACGCTCAATAGGGTGACCGACAATAGTGGGAGTCA
AACTGTTGTGTGTTGGACAGGAGGCTCACAACAGGC

>SEQ ID NO. 151: PLATE#713.H09.M13F
GGGAGACAAGAATAAACGCTCAATTGGGTGACCGACNATAATGGGAGTCC
NATTGTTGTGTGTTCGAGAGGAGGCTCACAACAGGC

>SEQ ID NO. 152: PLATE#713.A07.M13F
GGGAGACAAGAATAAACGGTCAATGGGGTGACCGACAATTATGGGAGTCT
AAATGTTGTGATTTCGACAGGGGGCTCACAACAGGC

>SEQ ID NO. 153: PLATE#713.E11.M13F
GGGAGACAAGAATAAACGCTCAATAGGGTGACCGACAACAATGGGAGTTA
AGGTGTTGTGTGTTCGACAGGAGGCTCACAACAGGC

>SEQ ID NO. 154: PLATE#713.G08.M13F
GGGAGACAAGAATAAACGCTCAATGGGGTGAGCGACAATTATGGGAGTGT
AAACGTTGTGATTTCGACAGGAGGCTGACAAGAGGC

>SEQ ID NO. 155: PLATE#713.A11.M13F
GGGAGACAAGAATAAACGCTCAATGGGGTGACCGACAATTATGGGAGTCT
AAATGTTGTGATTCGACAGGAGGCTCACAACAGGC

>SEQ ID NO. 156: PLATE#713.D07.M13F
GGGAGACAAGAATAAACGGTCAAACCTGTGGTTGATATGTTAGTTCTT
AGTTGTGTGTGGCTTCGACAGGAGGCTCACAACAGGC

>SEQ ID NO. 157: PLATE#713.C09.M13F
GGGAGACAAGAATAAAGGCTCAATCCTGTAGAGTTTTTATTCGGTTGAT
GGGCAGTGTTTTTTATTCGACAGGAGGCTCACAACAGGC

>SEQ ID NO. 158: PLATE#713.F09.M13F
GGGAGACAAGAATAAACGCTCAATCCTGTAGAGTTTTTATTGGGTTGAT
GGGCACTGTTTTTTATTCGACAGGAGGCTCACAACAGGC

>SEQ ID NO. 159: PLATE#713.D08.M13F
GGGAGAGAAGAATAAACGCTCAATCCTGTAGAGTTTTTTCGGTTGAT
GGGCAGTGTTTTTTATTCGACAGGAGGCTCACAACAGGC

>SEQ ID NO. 160: PLATE#713.C07.M13F
GGGAGACAAGAATAAAGGCTCAATCGTGTAGAGTCTTTTATTCGGTTGAT
GGGCACTGTTTTTATTCGACAGGAGGCTCACAACAGGC

>SEQ ID NO. 161: PLATE#713.B11.M13F
GGGAGACAAGAATAAACGCTCAACCTGTCATGGGAGGTTTAACTAGT
GCTGGGGTACCTGTAATTCGACAGGAGGCTCACAAGAGGC

The sequences of SEQ ID NO. 162 through SEQ ID No. 225 were generated from either R10 or R13 of activity selection only with the SS pool (no pre-enrichment for BaL binders) (plate 810 sequences went through 10 rounds and plate 813 sequences went through 13 rounds).

>SEQ ID NO. 162: PLATE#813.D08.M13F
GGAGCCTTCCTCCGGAAGTGAAGAGTAA--CACAGGGAATGCGTACTCTT
CTT-ATTTGTCCGGTTTCCCGAGCTT

>SEQ ID NO. 163: PLATE#813.D05.M13F
GGAGCCTTCCTGCGGAAGTCAAGAGTAA--CACAGGGAATGCGTACTCTT
CTT-ATTTGTCCGGTTTCGGGAGCTT

>SEQ ID NO. 164: PLATE#813.C06.M13F
GGAGCCTTCCTCCGGAAGTCAAGAGTAA--CACAGGGAATGCGTACTCTT
CTT-ATTTGTCCGGTTTCCCGAGCTT

>SEQ ID NO. 165: PLATE#813.C07.M13F
GGAGCCTTCCTCCGGAAGTCAAGAGTAA--CACAGGGAATGCGTACTCTT
CTT-ATTTGTCCGGTTTCCCGAGCTT

>SEQ ID NO. 166: PLATE#813.D07.M13F
GGAGCCTTCCTCCGGAAGTCAAGAGTAA--CACAGGGAATGCGTACTCTT
CTT-ATTTGTCCGGTTTCCCGAGCTT

>SEQ ID NO. 167: PLATE#810.C02.M13F
GGAGCCTTCCTCCGGAAGTCAAGAGTAA--CACAGGGAATGCGTACTCTT
CTT-ATTTGTGCGGTTTCCCGAGCTT

>SEQ ID NO. 168: PLATE#813.A05.M13F
GGAGCCTTCCTCCGGAAGTCAAGAGTAA--CACAGGGAATGCGTACTCTT
CTT-ATTTGTCCGGTTTCGGGAGCTT

>SEQ ID NO. 169: PLATE#813.A06.M13F
GGAGCCTTCCTCCGGAAGTCAAGAGTAA--CACAGGGAATGCGTACTCTT
CTT-ATTTGTGCGGTTTCCCGAGCTT

>SEQ ID NO. 170: PLATE#813.B05.M13F
GGAGCCTTCCTCCGGAAGTCAAGAGTAA--CACAGGGAATGCGTACTCTT
CTT-ATTTGTGGGGTTTCCCGAGCTT

>SEQ ID NO. 171: PLATE#810.G0L.M13F
GGAGCCTTCCTCCGGAAGTGAAGAGTAA--CACAGGGAATGCGTACTCTT
CTT-ATTTGTCCGGTTTCCCGAGCTT

>SEQ ID NO. 172: PLATE#813.G06.M13F
GGAGCCTTCCTCCGGAAGTCAAGAGTAA--CACAGGGAATGCGTACTCTT
CTT-ATTTGTCCGGTTTGCCGAGGTT

>SEQ ID NO. 173: PLATE#813.G07.M13F
GGAGCCTTCCTCCGGAAGTGAAGAGTAA--CACAGGGAATGCGTACTCTT
GTT-ATTTGTCGGGTTTGCCGAGCTT

>SEQ ID NO. 174: PLATE#813.H06.M13F
GGAGCCTTCCTCCGGAAGTCAAGAGTAA--CACAGGGAATGCGTACTCTT
CTT-ATTTGTCCGGTTTGCGGAGCTT

>SEQ ID NO. 175: PLATE#810.H03.M13F
GGAGGCTTCCTCCGGAAGTCAAGAGTAA--CACAGGGAATGCGTACTCTT
CTT-ATTTGTCCGGTTTCCCGAGCTT

>SEQ ID NO. 176: PLATE#810.A02.M13F
GGAGCCTTCCTCCGGAAGTCAAGAGTAG--CACAGGGAATGCGTACTCTT
CTT-ATTTGTCCGGTTTCGCGAGCTT

>SEQ ID NO. 177: PLATE#810.E01.M13F
GGAGCCTTCCTCCGGAAGTCAAGAGTAA--CACAGGGAATGCGTACTCTT
CTT-ATTTGTCGGGTTTCCCGAGCTT

>SEQ ID NO. 178: PLATE#813.F08.M13F
GGAGCCTTCCTCCGGAAGTCAAGAGTAG--CACAGGGAATGCGTACTCTT
CTT-ATTTGTCCGGTTTCCCGAGCTT

>SEQ ID NO. 179: PLATE#810.C04.M13F
GGAGCCTTCCTCCGGAAGTCAAGAGTAG--CACAGGGAATGCGTACTCTT
CTT-ATTTGTCCGGTTTCCCGAGCTT

>SEQ ID NO. 180: PLATE#810.A03.M13F
GGAGCCTTCCTCCGGAAGTCAAGAGTAG--CACAGGGAATGCGTACTCTT
CTT-ATTTGTCCGGTTTCCCGAGCTT

>SEQ ID NO. 181: PLATE#810.D04.M13F
GGAGCCTTCCTCCGGAAGTCAAGAGTAG--CACAGGGAATGCGTACTCTT
CTT-ATTTGTCCGGTTTCCCGAGCTT

>SEQ ID NO. 182: PLATE#810.D03.M13F
GGAGCCTTCCTCCGGAAGTCAAGAGTAG--CACAGGGAATGCGTAGTCTT
CTT-ATTTGTCCGGTTTCCCGAGCTT

>SEQ ID NO. 183: PLATE#810.G04.M13F
GGAGCCTTCCTCCGGAAGTCAAGAGTAG--CACAGGGAATGCGTACTCTT
CTT-ATTTGTCCGGTTTCCCGAGCTT

>SEQ ID NO. 184: PLATE#810.E04.M13F
GGAGCCTTGCTCCGGAAGTCAAGAGTAG--CACAGGGAATGCGTACTCTT
CTT-ATTTGTCGGGTTTGGCGAGCTT

>SEQ ID NO. 185: PLATE#813.B08.M13F
GGAGCCTTCGTCCGGAAGCCAAGAGTAA--CACAGGGAATGCGTACTCTT
CTT-ATTTGTCCGGTTTCGCGAGCTT

>SEQ ID NO. 186: PLATE#810.G03.M13F
GGAGCGTTCCTCCGGAGGTCAAGAGTAA--CACAGGGAATGGGTACTCTT
CTT-ATTTGTCCGGTTTCCCGAGGTT

>SEQ ID NO. 187: PLATE#813.H05.M13F
GGAGCCTTGCTCCGGAAGTCAAGAGTAA--CACAGGGAACGCGTACTCTT
CTT-ATTTGTCCGGTTTCCCGAGCTT

>SEQ ID NO. 188: PLATE#813.D06.M13F
GGAGCCTTCCTCCGGAAGTCAAGAGTAA--CACAGGGAACGCGTACTCTT
CTT-ATTTGTCCGGTTTCCCGAGCTT

>SEQ ID NO. 189: PLATE#810.C01.M13F
GGAGCCTTCCTCCGGAAGTCAAGAGTAG--GACAGGGAATGCGCTCTCTT
CTT-ATTTGTCCGGTTTCCCGAGCTT

>SEQ ID NO. 190: PLATE#813.H07.M13F
GGAGCCTTCCTCCGGATTCCGGACCTG---TTTACGCAATATGA-ATTAT
TTGCGTGGCCTCCGGTTTCGCGAGCTT

>SEQ ID NO. 191: PLATE#810.B01.M13F
GGAGCCTTCCTCCGGATTCCGGACCTG---TTTACGCAATATGA-ATTAT
TTGCGTCGCCTCCGGTTTCCCGAGCTT

>SEQ ID NO. 192: PLATE#810.D02.M13F
GGAGCCTTCCTCCGGATTCCGGACCTG---TTTACGCAATATGA-ATTAT
TTGCGTGGCCTCCGGTTTCCCGAGCTT

>SEQ ID NO. 193: PLATE#810.B02.M13F
GGAGCCTTCCTCCGGATTCCGGACCTG---TTTACGCAATATGA-ATTAT
TTGGGTCGCCTCCGGTTTCCCGAGCTT

>SEQ ID NO. 194: PLATE#813.E08.M13F
GGAGGCTTCCTCCGGATTCGGGACCTG---TTTACGCAATATGA-ATTAT
TTGCGTCGCCTCCGGTTTCCCGAGCTT

>SEQ ID NO. 195: PLATE#813.G08.M13F
GGAGCCTTCGTCCGGATTCCGGACCTG---TTTACGCAATATGA-ATTAT
TTGCGTCGGCTCCGGTTTCCCGAGCTT

>SEQ ID NO. 196: PLATE#810.E02.M13F
GGAGCCTTCCTCCGGATTCCGGACCTG---TTTACGCAATATGA-ATTAT
TTGCGTCGCGTCCGGTTTCCCGAGCTT

>SEQ ID NO. 197: PLATE#813.F05.M13F
GGAGCCTTCCTCCGGATTCCGGACCTG---TTTACGCAATATGA-ATTAT
TTGCGTCGCCTCCGGTTTCCCGAGCTT

>SEQ ID NO. 198: PLATE#813.B06.M13F
GGAGCCTTCCTCCGGATTCCGGACCTG---TTTACGCAATATGA-ATTAT
TTGGGTCGCCTCCGGTTTGGCGAGGTT

>SEQ ID NO. 199: PLATE#810.H01.M13F
GGAGCCTTCCTCCGGATTCGGGACGTG---TTTAGGGAATATGA-ATTAT
TTGCGTCGCCTGCGGTTTCGCGAGCTT

>SEQ ID NO. 200: PLATE#813.E05.M13F
GGAGCCTTCCTCCGGACTCCGGACCTG---TTTACGCAATATGA-ATTAT
TTGCGTCGCCTCGGGTTTCCCGAGCTT

>SEQ ID NO. 201: PLATE#810.B04.M13F
GGAGCCTTCCTCCGGATTCCGGACCTG---TTTACGCGATATGA-ATTAT
TTGCGTCGCCTCCGGTTTCCCGAGCTT

>SEQ ID NO. 202: PLATE#810.F02.M13F
GGAGCGTTCCTCCGGATTCCGGACCTG---TTTACGCGATATGA-ATTAT
TTGCGTCGCCTCCGGTTTCCCGAGCTT

>SEQ ID NO. 203: PLATE#813.C05.M13F
GGAGCCTTCCTCCGGAGTAGTCTACGAA--TGATTGGAAAC-GCATTCGT
ACT-TTTGTGTCCGGTTTCCCGAGCTT

>SEQ ID NO. 204: PLATE#813.G05.M13F
GGAGCCTTCCTCCGGAGTAGTCTACGAC-TGATTGGAAAC-GCATTCGT
ACT-TATGTGTCCGGTTTCCCGAGCTT

>SEQ ID NO. 205: PLATE#813.E06.M13F
GGAGCCTTCCTCCGGAGTAGTCTACGAC-TGATTGGAAAC-GCATTCGT
ACT-TTTGTGTCCGGTTTCCCGAGCTT

>SEQ ID NO. 206: PLATE#810.A04.M13F
GGAGCCTTCCTCCGGAGTAGTCTACGAC--TGATTGGAAAC-GCATTCGT
ACT-TTTGTGTCCGGTTTCCCGAGCTT

>SEQ ID NO. 207: PLATE#810.F03.M13F
GGAGCCTTCCTCCGGAGTAGTCTACGAC--TGATTGGAAAC-GCATTCGT
ACT-TTTGTGTCCGGTTTGCCGAGCTT

>SEQ ID NO. 208: PLATE#813.A08.M13F
GGAGCCTTCCTCCGGAGTAGTCTACGAC--TGATTGGAAAC-GCATTCGT
ACT-TTTGTGTCCGGTTTCGGGAGCTT

>SEQ ID NO. 209: PLATE#813.A07.M13F
GGAGCCTTCCTCCGGAGTAGTCTACGAC--TGATTGGAAAC-GCATTCGT
AGT-TTTGTGCCGGTTTCGGGAGCTT

>SEQ ID NO. 210: PLATE#810.G02.M13F
NGAGCCTTCCTCCGGATTCCGGACCTG---TTTACNCAATATGA-ATTAT
TTNCGTCNCGTCCGGTTTCCCGAGCTT

>SEQ ID NO. 211: PLATE#810.A01.M13F
GGAGCCTTCCTCCGGAGTAAA-TACGGA--TACGCGCAAATTGAAATCGT
AGTGTGCATATCCGGTTTCCCGAGCTT

>SEQ ID NO. 212: PLATE#810.E03.M13F
GGAGCCTTCCTCCGGATACAATACTTG---GG-GCACAACAAGTTATTAT
CTTTCCGGGGTCGGGTTTCGCGAGCTT

>SEQ ID NO. 213: PLATE#810.D01.M13F
GGAGCCTTCCTCCGGATGCGA-AAGTA---TGATGGTCTTTACTTTTGAA
GATCCTGTGGTCCGGTTTCCCGAGCTA

>SEQ ID NO. 214: PLATE#810.B03.M13F
GGAGCCTTCCTCCGGAAACCGTTATCAAAAAAAACACGATCTGCTCTATC
GCT-TGTTCGTCGGGTTTCCCGAGCTT

>SEQ ID NO. 215: PLATE#810.F01.M13F
GGAGCCTTCCTCCGGAAA-CCCATGTT---GGCAATTACATTTCACAGTA
CTTGTTGGCGTCCGGTTTCCCGAGCTT

>SEQ ID NO. 216: PLATE#813.E07.M13F
GGAGCCTTCCTCCGGAAACGGCAAGTG---TATATGTCCGGTCTTTT-AG
TACACT-TGGTCGGGTTTCCCGAGCTT

>SEQ ID NO. 217: PLATE#810.G03.M13F
GGAGCCTTCCTCCGGATCAGCCACAGT---TAAAAATAGCTTGTT-TGTG
CTTATCTGGGTCCGGTTTGCCGAGCTT

>SEQ ID NO. 218: PLATE#813.H08.M13F
GGAGCCTTCCTCCGGAAATA-CGGTTTGCTAAAAGC--ATCTTCCATCCA
TTG-AGTTGGTCGGGTTTCCCGAGCTT

>SEQ ID NO. 219: PLATE#813.B07.M13F
GGAGCCTTCCTCCGGAAATA-CGGTTTGCTAAAAGC--ATCTTCCATCCA
TTG-AGATGGTCCGGTTTCCCGAGCTT

>SEQ ID NO. 220: PLATE#810.H04.M13F
GGAGCCTTCCTCCGGATT-GCCGTCTAGCAAATAGTTTTTCCGAAACTAG
TCCGGAG-TGTCCGGTTTCGCGAGCTT

>SEQ ID NO. 221: PLATE#813.C08.M13F
GGAGCCTTCCTCCGGAAACGCTTATGCAATTAAGCAT-CCGACTCATTTG
TCT-TTTGGGTCCGGTTTCCCGAGCTT

>SEQ ID NO. 222: PLATE#813.F06.M13F
GGAGCCTTCCTGCGGAAATC-CGGTAAAGATGACCA--ATGTTTCTAGTG
TGT-TCGTGGTCCGGTTTCCCGAGCTT

>SEQ ID NO. 223: PLATE#810.F04.M13F
GGAGCCTTCCTCCGGAAACTTGACACGA-CTGC-AATTTGTGTTACGCAG
TCTGTTGG---TCCGGTTTCCCGAGCTT

>SEQ ID NO. 224: PLATE#810.H02.M13F
GGAGCCTTCCTCCGGAAA-TCGACATAGTCCGCTAATTTTTGCTCGTTAG
TCAGGTG---TCGGGTTTCGCGAGCTT

>SEQ ID NO. 225: PLATE#813.F07.M13F
GGAGCCTTCCTCCGGAAA-CCCGCATCATAGGCGATTGGATAGCA---A
TCCACCTACATCCGGTTTCCCGAGCTT

Example 2

Aptamer Minimization

SELEX typically yields RNA molecules 70 to 90 nucleotides long. Minimizing aptamer length facilitates chemical synthesis of aptamer candidates and can increase the affinity of the aptamer-ligand complex by eliminating alternative, non-binding structures. Once individual aptamers are identified from the original pool, the minimal sequence element required for high affinity binding can be identified through two parallel approaches: (1) truncation analysis by limited alkaline hydrolysis, and (2) doped reselection (methods are reviewed in Fitzwater & Polisky, 1996).

Example 3

Aptamer Optimization for Nuclease Resistance

Nucleic acids are degraded in serum by a combination of endonucleases and 5'→3' and 3'→5' exonucleases. Appropriate chemical modifications, as otherwise disclosed herein, block each activity (Pieken et al., 1991; Cummins et al., 1995; Jellinek et al., 1995; Dougan et al., 2000). Briefly, incorporation of 2'-fluoropyrimidines during selection in transcription reactions, and post selection addition of 2'-O-methyl purines protect aptamers from endonuclease degradation, while modification of termini with a 3'-3' thymidine cap can provide significant resistance to exonucleases.

Example 4

Clonal Analysis and Aptamer Activity Assays

When selection has reached the point where further rounds do not increase the fraction of pooled RNA bound to gp120, or to other complexes detailed above, the pooled template DNA are cloned using the TOPO TA cloning system (Invitrogen). Individual clones are sequenced. Unique clones are screened for the desired properties using the techniques outlined below.

Selected aptamer clones are evaluated on the basis of their ability to bind to gp120. Simple binding is required for aptamers to be CD4 mimics and thus can be used to rapidly triage the library of selected aptamer clones. Individual clones which demonstrate gp120 binding are carried forward for further screening on the basis of the ability to mimic the biological action of CD4 on gp120. Sensitive three-component optical biosensor binding assays are configured to detect CD4 or aptamer inducible changes in binding affinities of gp120 for biotinylated CCR5 peptide (Cormier et al., 2000), on a Biacore 3000 surface plasmon detection system. In addition, gp120 dependent binding of $^{32}$P-labeled aptamer clones on CCR5 expressing cells are screened in filter binding experiments functionally analogous to those used to quantitate the effects of sCD4 upon gp120 binding to co-receptors (Doranz et al., 1999) as well as for the ability of binding to be specifically blocked by the CCR5 specific monoclonal antibody 3A9 (Wu et al, 1997) and the gp120 CD4i epitope specific antibody 17b (Kwong et al., 1998). Cells expressing CCR5 can be obtained, e.g., from Merck Research Laboratories (West Point, Pa.), soluble CD4 has been purchased from US Biologics (Swampscott, Mass.) and antibodies 3A9 and 17b are freely available from the NIH AIDS Research and Reference Reagent Program.

Example 5

Covalent Coupling of Aptamers to gp120

Activity of the aptamers in an effective vaccine are enhanced when the aptamers are covalently coupled to gp120. Anti-gp120 aptamers are synthesized with polyethylene glycol (PEG) spacers at their 5'-termini to yield aptamers with from ~20-200 Å (Angstrom) spacers ending in a primary amine moiety. The length and "water-like" properties of the spacer allow the aptamer to bind to gp120 in a manner identical to that observed in an uncoupled 2-piece system. A series of single cysteine mutations in the N and C termini and non-neutralizing face of gp120 are generated by standard mutagenesis techniques. Amine terminated aptamers are then covalently attached to free thiols on gp120 using a hetero-bifunctional crosslinker available from Pierce (Sulfo-LC-SPDP, sulfosuccinimidyl 6-[3'-(2-pyridyldithio)-propionamido] hexanoate). Aptamer/gp120 conjugates are then screened for the ability to bind to CCR5 peptide or to CCR5 expressing cells as described above. By testing multiple gp120 BaL mutants and aptamer spacer lengths the optimal configuration for biochemical activity is identified.

Example 6

Generation of Antibodies Against Aptamer/gp120 Immunogens

Aptamers demonstrating activity in in vitro functional assays are covalently coupled to gp120 and complexes assayed for the ability to induce neutralizing antibody responses. Immunogens are formulated with the saponin based QS21 adjuvant at final concentrations of 50-100 μg/ml and 100 μg/ml respectively (Evans et al., 2001 and McGaughey et al., 2003). At least six sets of immunization experiments can be performed in parallel. Guinea pigs are immunized with either: i.) optimized aptamer/gp120 conjugate, ii.) a scrambled sequence (nonfunctional) aptamer/gp120 conjugate, iii.) aptamer/gp 120 complex without covalent conjugation, iv.) scrambled sequence aptamer/gp120 complex without covalent conjugation, v.) gp120 only, or vi.) adjuvant only. Thus, the effects of the aptamer(s), the conjugation, and nucleic acid in comparison with gp120 alone as immunogens are evaluated. Various aptamer complexes are injected into guinea pigs to provoke an immune response. For each experiment, three animals receive 0.05 ml (50-100 μg) of vaccine in subcutaneous injection. Two booster immunizations take place at 3-week intervals, and animals are bled 10-28 days after immunizations. Serum antibodies against gp120 is quantified initially by gp120 ELISA (Moore et al., 1989).

Example 7

Cell-Based HIV Neutralization Assays

Neutralization assays are performed using U87.CD4.CCR5 cells (available from the NIH AIDS Research Reagent Database) (Bjomal et al., 1997 and Richman et al., 2003) transiently transfected with HIV-1 LTR driven β-galactosidase, and the non-fluorescent fluorogenic substrate, 5-chloromethylfluoroscein di-β-D-galactopyranoside (CMFDG) (Molecular Probes) in a single cycle HIV-1 infection assay. HIV infection results in expression of Tat which transactivates expression of the β-galactosidase gene which can be detected via production of fluorescein. Each dilution is tested in triplicate. Pre-immune sera is also tested as a control for nonspecific neutralization. An HIV-1 BaL strain is available for single cycle infectivity assays from Advanced Bioscience Laboratories (Gaithersburg, Md.). Viruses (50-100 50% tissue culture infective dose) in 50 μl of RPMI complete medium containing 20 U of interleukin-2 (Hoffman-LaRoche) is pre-incubated with an equal volume of serially diluted heat-inactivated sera (35 min at 56° C.) for 10 minutes at room temperature. This mixture is then incubated in 96-well flat bottom plates with transfected U87.CD4.CCR5 cells for 48 hours at 37° C. to allow for a single cycle of infection and production of β-glactosidase. Production of β-glactosidase can then be measured by addition of the fluorogenic substrate CMFDG and quantification of fluorescein fluorescence in a Packard Fusion fluorescence plate reader. Each dilution is tested in triplicate. Pre-immune sera is also tested as a control for nonspecific neutralization.

Example 8

In Vitro Assays for Evaluating Aptamer Stability

Serum stabilities of aptamers are assayed in vitro as described (Green et al., 1995). Briefly, 5'-$^{32}$P end-labeled aptamers are incubated at 2 nM in human serum at 37° C. Reactions are terminated at specific time points by addition of 87% formamide and analyzed for percent degradation by denaturing PAGE.

Example 9

Coupled Selection

In one embodiment, the selection for gp120 specific binding aptamers can be facilitated by linking the RNA pool to a capture (oligonucleotide) probe attached at the end of a spacer (e.g., a PEG spacer). The probe-spacer is attached to either a monoclonal antibody with a known locus specificity on gp120, or directly to gp120. In this manner, a low affinity aptamer that is capable of inducing a conformational shift in gp 120 can be more easily identified. In one embodiment, the probe-spacer is linked to a gp120-specific binding monoclonal antibody or fragment thereof through linking chemistries to the glycosyl residues on the antibody or fragment through linkers and linking methods known in the art. In one embodiment, the probe-spacer is linked directly to gp120 by linking to glycosyl residues on gp120 using the same linkers and linking chemistries also known in the art.

By pre-coupling pools to gp120, the initial requirements for high affinity binders are removed and aptamers that can mimic CD4 but have low intrinsic gp120 affinity can be enriched. Using monoclonal antibodies of known epitopes to attach the RNA pool to gp120 also provides an indication of where to engineer in a cysteine mutation for final covalent coupling of aptamer and gp120 in subsequent vaccine trials. Monoclonal antibodies or Fab fragments thereof that are chosen are non-neutralizing and do not interfere with either receptor or co-receptor binding. This method is compatible with activity based selection methods.

References cited above by author and year of publication are given their full citation below, and is each herein incorporated by reference in its entirety.

Barnett S W, Lu S, Srivastava I, Cherpelis S, Gettie A, Blanchard J, Wang S, Mboudjeka I, Leung L, Lian Y, Fong A, Buckner C, Ly A, Hilt S, Ulmer J, Wild C T, Mascola JR, Stamatatos L. (2001) "The ability of an oligomeric human immunodeficiency virus type 1 (HIV-1) envelope antigen to elicit neutralizing antibodies against primary HIV-1 isolates is improved following partial deletion of the second hypervariable region." J. Virol. 75: 5526-40.

Belshe R B, Bolognesi D P, Clements M L, Corey L, Dolin R, Mestecky J, Mulligan M, Stablein D, Wright P. (1994) "HIV infection in vaccinated volunteers." JAMA. 272: 431.

Burton D R. (1997) "A vaccine for HIV type 1: the antibody perspective." Proc Natl Acad Sci USA. 94: 10018-23.

Cohen J. (1994) "AIDS vaccine research. U.S. panel votes to delay real-world vaccine trials." Science. 264: 1839.

Conrad R C, Giver L, Tian Y, Ellington A D (1996) "In vitro selection of nucleic acid aptamers that bind proteins." Methods. Enzymol. 267: 336-66.

Cormier E G, Persuh M, Thompson D A D, Lin S W, Sakmar T P, Olsen W C, Dragic T (2000) "Specific interaction of CCR5 amino-terminal domain peptides containing sulfotyrosines with HIV-1 envelope glycoprotein gp120" PNAS. 97: 5762-67.

Cummins L L, Owens S R, Risen L M, Lesnik E A, Freier S M, McGee D, Guinosso C J, Cook P D (1995) "Characterization of fully 2'-modified oligoribonucleotide hetero- and homoduplex hybridization and nuclease sensitivity." Nucl. Acids. Res. 23: 2019-24.

Dougan H, Lyster D M, Vo V C, Stafford A, Weitz J I, Hobbs J B (2000) "Extending the lifetime of anticoagulant oligodeoxynucleotide aptamers in blood." Nucl. Med. Biol. 27: 286-97.

Doranz BJ, Baik SSW, Doms RW (1999) "Use of a gp120 binding assay to dissect the requirements and kinetics of human immunodeficiency virus fusion events" J. Virol. 73: 10346-58.

Emini EA, Schleif WA, Nunberg JH, Conley AJ, Eda Y, Tokiyoshi S, Putney SD, Matsushita S, Cobb KE, Jett C M (1992) "Prevention of HIV-1 infection in chimpanzees by gp120 V3 domain-specific monoclonal antibody." Nature. 355: 728-30.

Emini E. A. (2002) HIV Vaccines 2000: Prospects and Challenges. In "The Human Immunodeficiency Virus", Princeton University Press, Princeton, N.J. pp 481-509.

Evans TG et. al. (2001) "QS-21 promotes an adjuvant effect allowing for reduced antigen dose during HIV-1 envelope subunit immunization in humans" Vaccine. 19: 2080-91.

Fitzwater T, Polisky B (1996) "A SELEX primer" Methods Enzymol. 267: 275-301.

Fouts T, Godfrey K, Bobb K, Montefiori D, Hanson C V, Kalyanaraman V S, DeVico A, Pal R (2002) "Crosslinked HIV-1 envelope-CD4 receptor complexes elicit broadly cross-reactive neutralizing antibodies in rhesus macaques" PNAS. 99: 11842-47.

Gaschen B, Taylor J, Yusim K, Foley B, Gao F, Lang D, Novitsky V, Haynes B, Hahn B H, Bhattacharya T, Korber B. (2002) "Diversity considerations in HIV-1 vaccine selection." Science. 296: 2354-60.

Graham BS. (2002) "Clinical trials of HIV vaccines." Annu Rev Med. 53: 207-21.

Green LS, Jellinek D, Bell C, Beebe LA, Feistner BD, Gill SC, Jucker FM, Janjic N (1995) "Nuclease-resistant nucleic acid ligands to vascular permeability factor/vascular endothelial growth factor." Chem Biol. 2: 683-95.

Jellinek D, Green LS, Bell C, Janjic N (1994) "Inhibition of receptor binding by high-affinity RNA ligands to vascular endothelial growth factor." Biochemistry. 33: 10450-56.

Jellinek, D, L. S. Green; C. Bell; C. K. Lynott; N. Gill; C. Vargeese; G. Kirschenheuter; D. P. McGee; P. Abesinghe; W. A. Pieken, et al. (1995) "Potent 2'-amino-2'-deoxypyrimidine RNA inhibitors of basic fibroblast growth factor" Biochemistry 34:11363-11372.

Kahn J. O., Sinangil F, Baenziger J, Murcar N, Wynne D, Coleman R L, Steimer K S, Dekker C L, Chernoff D. (1994) "Clinical and immunologic responses to human immunodeficiency virus (HIV) type 1 SF2 gp120 subunit vaccine combined with MF59 adjuvant with or without muramyl tripeptide dipalmitoyl phosphatidylethanolamine in non-HIV-infected human volunteers." J Infect Dis. 170: 1288-91.

Kowalski M, Potz J, Basiripour L, Dorfinan T, Goh W C, Terwilliger E, Dayton A, Rosen C, Haseltine W, Sodroski J. (1987) "Functional regions of the envelope glycoprotein of human immunodeficiency virus type 1." Science. 237: 1351-5.

Kraus, W. James; A. N. Barclay., (1998) "Cutting edge: novel RNA ligands able to bind CD4 antigen and inhibit CD4$^+$ T lymphocyte function" Journal of Immunology 160:5209-5212.

Kwong PD, Wyatt R, Robinson J, Sweet RW, Sodroski J, Hendrickson WA (1998) "Structure of an HIV gp120 envelope glycoprotein in complex with the CD4 receptor and a neutralizing human antibody." Nature. 393: 648-59.

Kwong, PD, Doyle M L, Casper DJ, Cicala C, Leavitt SA, Majeed S, Steenbeke TD, Venturi M, Chaikin I, Fung M, Katinger H, Parren P, Robinson J, Van Ryk D, Wang L, Burton D, Freire E, Wyatt R, Sodroski J. Hendrickson W, Arthos J, (2002) "HIV-1 evades antibody-mediated neutralization through conformational masking of receptor-binding sites" Nature. 420: 678-82.

Langlois AJ, Desrosiers R C, Lewis MG, KewalRamani V N, Littman DR, Zhou JY, Manson K, Wyand M S, Bolognesi DP, Montefiori DC. (1998) "Neutralizing antibodies in sera from macaques immunized with attenuated simian immunodeficiency virus." J. Virol. 72: 6950-5.

Leonard C K, Spellman M W, Riddle L, Harris RJ, Thomas JN, Gregory TJ. (1990) "Assignment of intrachain disulfide bonds and characterization of potential glycosylation sites of the type 1 recombinant human immunodeficiency virus envelope glycoprotein (gp120) expressed in Chinese hamster ovary cells." J Biol. Chem. 265: 10373-82.

Lu M, Blacklow S C, Kim P S. (1995) "A trimeric structural domain of the HIV-1 transmembrane glycoprotein." Nat Struct Biol. 2: 1075-82.

Martin L, Stricher F, Misse D, Sironi F, Pugniere M, Barthe P, Prado-Gotor R, Freulon I, Magne X, Roumestand C, Menez A, Lusso P, Veas F, Vita C (2003) "Rational design of a CD4 mimic that inhibits HIV-1 entry and exposes cryptic neutralization epitopes" Nature Biotechnology. 21: 71-76.

Mascola JR, Snyder S W, Weislow O S, Belay S M, Belshe R B, Schwartz DH, Clements ML, Dolin R, Graham BS, Gorse GJ, Keefer M C, McElrath MJ, Walker MC, Wagner KF, McNeil JG, McCutchan FE, Burke DS. (1996) "Immunization with envelope subunit vaccine products elicits neutralizing antibodies against laboratory-adapted but not primary isolates of human immunodeficiency virus type 1. The National Institute of Allergy and Infectious Diseases AIDS Vaccine Evaluation Group." J Infect Dis. 173: 340-8.

McGaughey GB, Citron M, Danzeisen RC, Freidinger RM, Garsky VM, Hurni WM, Joyce JG, Liang X, Miller M, Sjiver J, Bogusky MJ (2003) "HIV-1 vaccine development: constrained peptide immunogens show improved binding to anti-HIV-1 gp41 MAb" Biochemistry. 42: 3214-23.

Moulard M, Phogat SK, Shu Y, Labrijn AF, Xiao X, Binley JM, Zhang MY, Sidorov IA, Broder CC, Robinson J, Parren PW, Burton DR, Dimitrov DS. (2002) "Broadly cross-reactive HIV-1-neutralizing human monoclonal Fab selected for binding to gp120-CD4-CCR5 complexes." Proc Natl Acad Sci USA. 99: 6913-8.

Nixon DF, Douek D, Kuebler P J, Jin X, Vesanen M, Bonhoeffer S, Cao Y, Koup RA, Ho DD, Markowitz M. (1999) "Molecular tracking of an Human Immunodeficiency Virus nef specific cytotoxic T-cell clone shows persistence of clone-specific T-cell receptor DNA but not mRNA following early combination antiretroviral therapy." Immunol Lett. 1999 March;66(1-3):219-28.

Pieken WA, Olsen DB, Benseler F, Aurup H, Eckstein F (1991) "Kinetic characterization of ribonuclease-resistant 2'-modified hammerhead ribozymes." Science. 253: 314-7.

Poignard P, Saphire EO, Parren PW, Burton DR. (2001) "gp120: Biologic aspects of structural features." Annu Rev Immunol. 19: 253-74.

Prince AM, Reesink H, Pascual D, Horowitz B, Hewlett I, Murthy KK, Cobb KE, Eichberg JW. (1991) "Prevention of HIV infection by passive immunization with HIV immunoglobulin." AIDS Res Hum Retroviruses. 7: 971-3.

Profy AT, Salinas PA, Eckler LI, Dunlop NM, Nara P L, Putney SD. (1990) "Epitopes recognized by the neutralizing antibodies of an HIV-1-infected individual." J. Immunol. 144: 4641-7.

Putkonen P, Thorstensson R, Ghavamzadeh L, Albert J, Hild K, Biberfeld G, Norrby E. (1991) "Prevention of HIV-2 and SIVsm infection by passive immunization in cynomolgus monkeys." Nature. 352: 436-8.

Richman DD, Wrin T, Little SJ, Petropoulos CJ (2003) "Rapid evolution of the neutralizing antibody response to HIV type 1 infection" PNAS. 100: 4144-49.

Rizzuto CD, Wyatt R, Hernandez-Ramos N, Sun Y, Kwong PD, Hendrickson WA, Sodroski J. (1998) "A conserved HIV gp120 glycoprotein structure involved in chemokine receptor binding." Science. 280: 1949-53.

Ruckman J, Green LS, Beeson J, Waugh S, Gillette WL, Henniger DD, Claesson-Welsh L, Janjic N (1998) "2'-fluoropyrimidine RNA-based aptamers to the 165-amino acid form of vascular endothelial growth factor (VEGF$_{165}$)." J. Biol. Chem. 273: 20556-67.

Sattentau QJ, Moore JP. (1991) "Conformational changes induced in the human immunodeficiency virus envelope glycoprotein by soluble CD4 binding." J Exp Med. 174: 407-15.

Sattentau QJ, Moore JP, Vignaux F, Traincard F, Poignard P. (1993) "Conformational changes induced in the envelope glycoproteins of the human and simian immunodeficiency viruses by soluble receptor binding." J. Virol. 67: 7383-93.

Sayer N, Ibrahim J, Turner K, Tahiri-Alaoui A, James W. (2002) "Structural characterization of a 2'F-RNA aptamer that binds a HIV-1 SU glycoprotein, gp120." Biochem Biophys Res Commun. 2002 May 10;293(3):924-31.

Starcich BR, Hahn BH, Shaw GM, McNeely PD, Modrow S, Wolf H, Parks ES, Parks W P, Josephs SF, Gallo RC, et al. (1986) "Identification and characterization of conserved and variable regions in the envelope gene of HTLV-III/LAV, the retrovirus of AIDS." Cell. 45: 63748.

Sullivan N, Sun Y, Binley J, Lee J, Barbas CF 3rd, Parren PW, Burton DR, Sodroski J. (1998) "Determinants of human immunodeficiency virus type 1 envelope glycoprotein activation by soluble CD4 and monoclonal antibodies." J. Virol. 72: 6332-8.

Thali M, Moore JP, Furman C, Charles M, Ho DD, Robinson J, Sodroski J. (1993) "Characterization of conserved human immunodeficiency virus type 1 gp120 neutralization epitopes exposed upon gp120-CD4 binding." J. Virol. 67: 3978-88.

Trkola A, Dragic T, Arthos J, Binley J M, Olson WC, Allaway GP, Cheng-Mayer C, Robinson J, Maddon P J, Moore JP. (1996) "CD4-dependent, antibody-sensitive interactions between HIV-1 and its co-receptor CCR-5." Nature. 384: 184-7.

Trkola A, Purtscher M, Muster T, Ballaun C, Buchacher A, Sullivan N, Srinivasan K, Sodroski J, Moore JP, Katinger H. (1996) "Human monoclonal antibody 2G12 defines a distinctive neutralization epitope on the gp120 glycoprotein of human immunodeficiency virus type 1." J. Virol. 70: 1100-8.

Tucker C E, Chen L S, Judkins MB, Farmer JA, Gill SG, Drolet DW (1999) "Detection and plasma pharmacokinetics of an anti-vascular endothelial growth factor oligonucleotide ptamer (NX1838) in rhesus monkeys." J. Chromatography B. 732: 203-12.

Wantanabe M (2003) "Skeptical scientists skewer VaxGen statistics" Nature Medicine. 9: 376-77.

Wei X, Decker JM, Wang S, Hui H, Kappes JC, Wu X, Salazar-Gonzalez JF, Salazar MG, Kilby JM, Saag MS, Komarova NL, Nowak MA, Hahn BH, Kwong PD, Shaw GM (2003) "Antibody neutralization and escape by HIV-1" Nature. 422: 307-12.

Wu L, Gerard NP, Wyatt R, Choe H, Parolin C, Ruffing N, Borsetti A, Cardoso AA, Desjardin E, Newman W, Gerard C, Sodroski J. (1996) "CD4-induced interaction of primary HIV-1 gp120 glycoproteins with the chemokine receptor CCR-5." Nature. 384: 179-83.

Wu L, Paxton WA, Kassam N, Ruffing N, Rottman JB, Sullivan N, Choe H, Sodroski J, Newman W, Koup RA, Mackay CR (1997) "CCR5 levels and expression pattern correlate with infectability by macrophage-tropic HIV-1, in vitro" J. Exp. Med. 185: 1681-91.

Zhang W, Canziani G, Plugariu C, Wyatt R, Sodroski J, Sweet R, Kwong P, Hendrickson W, Chaiken I. (1999) "Conformational changes of gp120 in epitopes near the CCR5 binding site are induced by CD4 and a CD4 miniprotein mimetic." Biochemistry. 38: 9405-16.

Zhang W, Godillot AP, Wyatt R, Sodroski J, Chaiken I. (2001) "Antibody 17b binding at the co-receptor site weakens the kinetics of the interaction of envelope glycoprotein gp120 with CD4." Biochemistry. 40: 1662-70.

The invention having now been described by way of written description and examples, those of skill in the art will recognize that the invention can be practiced in a variety of embodiments and that the foregoing description and examples are for purposes of illustration and not limitation of the following claims.

---

What is claimed is:

1. A method for identifying an aptamer regulator comprising the steps:
   a) providing a target and a target partner that do not bind to each other in the absence of an aptamer regulator;
   b) contacting a mixture of nucleic acids with the target partner under conditions that favor specific binding between the nucleic acids and the target partner;
   c) partitioning the bound nucleic acids from the unbound nucleic acids, and retaining the unbound nucleic acids;
   d) contacting the unbound nucleic acids with the target and the target partner;
   e) partitioning nucleic acids bound to a target-target partner complex from unbound nucleic acids, wherein binding of a nucleic acid to the target induces a conformational change in the target that increases the binding affinity of the target for the target partner relative to when the target is not bound by the nucleic acid;
   f) retaining the nucleic acids bound to the target-target partner complex; and
   g) removing the retained nucleic acids that are bound to the target in the target-target partner complex,
   thereby identifying an aptamer regulator that binds to the target and induces a conformational change in the target that increases the binding affinity of the target for the target partner relative to the affinity of the target for the target partner without the aptamer regulator, wherein the binding of the aptamer regulator to the target is a prerequisite for target-target partner complex formation.

2. The method of claim 1, wherein the mixture of nucleic acids is a target-specific pool of nucleic acids having high affinity and specificity for the target.

3. The method of claim 2, wherein the target-specific pool of nucleic acids is diversified.

4. The method of claim 1, wherein the target partner is immobilized.

5. The method of claim 1, wherein the removing is by eluting the nucleic acids with an agonist competitor to the target.

6. The method of claim 1, wherein the removing is by contacting the bound nucleic acids with excess free target.

7. The method of claim 1, wherein the method further comprises the step of amplifying the retained nucleic acids and repeating steps a) to b).

8. The method of claim 1, wherein the method further comprises the step of screening the nucleic acids retained in step d) for a desired functional activity.

* * * * *

SEQUENCE LISTING

```
<160> NUMBER OF SEQ ID NOS: 231

<210> SEQ ID NO 1
<211> LENGTH: 24
<212> TYPE: DNA
<213> ORGANISM: Artificial
<220> FEATURE:
<223> OTHER INFORMATION: DNA template sequence

<400> SEQUENCE: 1
gcctgttgtg agcctcctgt cgaa                                                24

<210> SEQ ID NO 2
<211> LENGTH: 40
<212> TYPE: DNA
<213> ORGANISM: Artificial
<220> FEATURE:
<223> OTHER INFORMATION: DNA Template Sequence

<400> SEQUENCE: 2
ttgagcgttt attcttgtct ccctatagtg agtcgtatta                               40

<210> SEQ ID NO 3
<211> LENGTH: 40
<212> TYPE: DNA
<213> ORGANISM: Artificial
<220> FEATURE:
<223> OTHER INFORMATION: PCR Primer

<400> SEQUENCE: 3
taatacgact cactataggg agacaagaat aaacgctcaa                               40

<210> SEQ ID NO 4
<211> LENGTH: 24
<212> TYPE: DNA
<213> ORGANISM: Artificial
<220> FEATURE:
<223> OTHER INFORMATION: PCR Primer

<400> SEQUENCE: 4
gcctgttgtg agcctcctgt cgaa                                                24

<210> SEQ ID NO 5
```

```
<211> LENGTH: 16
<212> TYPE: DNA
<213> ORGANISM: Artificial
<220> FEATURE:
<223> OTHER INFORMATION: DNA Template Sequence

<400> SEQUENCE: 5
ggagccttcc tccgga                                                          16

<210> SEQ ID NO 6
<211> LENGTH: 17
<212> TYPE: DNA
<213> ORGANISM: Artificial
<220> FEATURE:
<223> OTHER INFORMATION: DNA Template Sequence

<400> SEQUENCE: 6
tccggtttcc cgagctt                                                         17

<210> SEQ ID NO 7
<211> LENGTH: 33
<212> TYPE: DNA
<213> ORGANISM: Artificial
<220> FEATURE:
<223> OTHER INFORMATION: PCR Primer

<400> SEQUENCE: 7
taatacgact cactatagga gccttcctcc gga                                       33

<210> SEQ ID NO 8
<211> LENGTH: 17
<212> TYPE: DNA
<213> ORGANISM: Artificial
<220> FEATURE:
<223> OTHER INFORMATION: PCR Primer

<400> SEQUENCE: 8
aagctcggga aaccgga                                                         17

<210> SEQ ID NO 9
<211> LENGTH: 86
<212> TYPE: DNA
<213> ORGANISM: Artificial
<220> FEATURE:
<223> OTHER INFORMATION: Cloned DNA Sequence

<400> SEQUENCE: 9
gggagacaag aataaacgct caattgggtg accgacaatt atgggagtca gcttgttgag         60
agttcgacag ggggctcaca acaggc                                              86

<210> SEQ ID NO 10
<211> LENGTH: 86
<212> TYPE: DNA
<213> ORGANISM: Artificial
<220> FEATURE:
<223> OTHER INFORMATION: Cloned DNA Sequence

<400> SEQUENCE: 10
gggagacaag aataaacgct caatagggtg accgacaata atgggagtca aactgttgtg         60
tgttcgacag gaggctcaca acaggc                                              86

<210> SEQ ID NO 11
<211> LENGTH: 88
<212> TYPE: DNA
<213> ORGANISM: Artificial
```

<220> FEATURE:
<223> OTHER INFORMATION: Cloned DNA Sequence

<400> SEQUENCE: 11
gggagacaag aataaacgct caactgtcgt attattttta gcggtctcaa ctaattgtgg    60 cttttcgac aggaggctca caacaggc    88

<210> SEQ ID NO 12
<211> LENGTH: 88
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (55)..(55)
<223> OTHER INFORMATION: n is a, c, g, or t

<400> SEQUENCE: 12
gggagacaag aataaacgct caactgtcgt attattttta gcggtctcaa ctagntgtgg    60 cttttcgac aggaggctca caacaggc    88

<210> SEQ ID NO 13
<211> LENGTH: 87
<212> TYPE: DNA
<213> ORGANISM: Artificial
<220> FEATURE:
<223> OTHER INFORMATION: Cloned DNA Sequence

<400> SEQUENCE: 13
gggagacaag aataaaccct caaccttcgc gttttgtcaa agtattttg aaggaattgt    60 gacttcgaca ggaggctcac aacaggc    87

<210> SEQ ID NO 14
<211> LENGTH: 87
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 14
gggagacaag aatnancnct caaccttcgc gttttgtcaa agtattttg aaggaattgt    60 gacttcgaca ggaggctcac aacaggc    87

<210> SEQ ID NO 15
<211> LENGTH: 88
<212> TYPE: DNA
<213> ORGANISM: Artificial
<220> FEATURE:
<223> OTHER INFORMATION: PCR Primer
<220> FEATURE:
<221> NAME/KEY: misc_feature
<222> LOCATION: (55)..(56)
<223> OTHER INFORMATION: n is a, c, g, or t
<220> FEATURE:

<221> NAME/KEY: misc_feature
<222> LOCATION: (59)..(59)
<223> OTHER INFORMATION: n is a, c, g, or t

<400> SEQUENCE: 15
gggagacaag aataaacgct caactgtcgt attattttta gcggtctcaa ctaanngtng    60 cttttttcgac aggaggctca caacaggc                                      88

<210> SEQ ID NO 16
<211> LENGTH: 87
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t

<400> SEQUENCE: 16
gggagacaag aatnaacgct caaccttcgc gttttgtcaa agtattttg aaggaattgt     60 gacttcnaca ggaggctcac aacaggn                                        87

<210> SEQ ID NO 17
<211> LENGTH: 88
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t

<400> SEQUENCE: 17
gggagacaag aatnnaccct caactgtcgn attattttca gcggnctcaa ctaattgtgg    60 cttttttcgac aggaggctca caacaggn                                      88

<210> SEQ ID NO 18
<211> LENGTH: 87
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (55)..(55)
<223> OTHER INFORMATION: n is a, c, g, or t
<220> FEATURE:
<221> NAME/KEY: misc_feature
<222> LOCATION: (57)..(59)
<223> OTHER INFORMATION: n is a, c, g, or t

<400> SEQUENCE: 18
gggagacaag aataaacgct caaccttcgc gttttgtcaa agtattttg aaggnannnt    60 gacttcgaca ggaggctcac aacaggc                                       87

<210> SEQ ID NO 19
<211> LENGTH: 89
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (55)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t

<400> SEQUENCE: 19
gggagacaag aataaacgct caactgtcgt attattttta gcggtctcaa ctaannngtn    60 acttttcga caggaggctc acaacaggc                                       89

<210> SEQ ID NO 20
<211> LENGTH: 87
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t

<400> SEQUENCE: 20
gggagacaag aataaacgct caaccttcgc gnttngtcaa agtatttnng anggaaaagn    60
ganttngaca ggaggctcnc aacaggc                                       87

<210> SEQ ID NO 21

```
<211> LENGTH: 87
<212> TYPE: DNA
<213> ORGANISM: Artificial
<220> FEATURE:
<223> OTHER INFORMATION: Cloned DNA Sequence

<400> SEQUENCE: 21
gggagacaag aataaacgct caacgtactg gttattcctg gttagcgtaa agtagtaagt    60
gagttcgaca ggaggctcac aacaggc                                       87

<210> SEQ ID NO 22
<211> LENGTH: 87
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (53)..(53)
<223> OTHER INFORMATION: n is a, c, g, or t

<400> SEQUENCE: 22
gggagacaag aataaacgct caagtaagat agcaggttat agaggcagaa canaatgtga    60
gttttcgaca ggaggctcac aacaggc                                       87

<210> SEQ ID NO 23
<211> LENGTH: 87
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (58)..(58)
<223> OTHER INFORMATION: n is a, c, g, or t

<400> SEQUENCE: 23
gggagacaag aataaacgct caactgagtg aggaaatgng ggagcatctt acggggganaa    60 ttgttcgaca ggaggctcac aacaggc                                       87

<210> SEQ ID NO 24
<211> LENGTH: 88
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 24
gggagacaag aataaacgct caataagagg ttaaagtgag acagnctaat tagatgggaa    60
ntagttcgac aggaggctca caacaggc                                      88

<210> SEQ ID NO 25
<211> LENGTH: 87
<212> TYPE: DNA
<213> ORGANISM: Artificial
```

<220> FEATURE:
<223> OTHER INFORMATION: Cloned DNA Sequence

<400> SEQUENCE: 25
gggagacaag aataaacgct caatgggagg tgagcgtaga tggggatatt atgcgttgcg    60
tgattcgaca ggaggctcac aacaggc    87

<210> SEQ ID NO 26
<211> LENGTH: 87
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (14)..(15)
<223> OTHER INFORMATION: n is a, c, g, or t

<400> SEQUENCE: 26
gggagacaag aatnnaccct caacttatct gaggaaatac ggatcttatt gcatttagcg    60
acgttcgaca ggaggctcac aacaggc    87

<210> SEQ ID NO 27
<211> LENGTH: 88
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 27
gggagacaag aatnancgct caagatttga cacacagtaa aaatagtac agtaagtgag    60 tgccttcgac aggaggctca caacaggc    88

<210> SEQ ID NO 28
<211> LENGTH: 87
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (40)..(42)
<223> OTHER INFORMATION: n is a, c, g, or t
<220> FEATURE:
<221> NAME/KEY: misc_feature
<222> LOCATION: (46)..(46)

<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t

<400> SEQUENCE: 28
gggagacaag aataancgct caaagtttcn antnacctgn nnttantcnt ncatgtgcna    60
tctttcgaca ggaggctcac aacaggc                                       87

<210> SEQ ID NO 29
<211> LENGTH: 73
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t

<400> SEQUENCE: 29
gganccttcc tccggaggtn ttnatattnc attacaaggg gnaaanntct tttggntccg    60
gtttcccgan ctt                                                      73

<210> SEQ ID NO 30
<211> LENGTH: 73
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature

```
<222> LOCATION: (43)..(43)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t

<400> SEQUENCE: 30
ggagccttcc tccggactta cagcacaant taaatttacg ggnaanctcg tccccgtccg    60
gtttcccgag ctt                                                       73

<210> SEQ ID NO 31
<211> LENGTH: 74
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 31
ggagccttcc tcnggcnctt gtgtgttaaa atttttattg cgcttttttg tttctcgtcc    60
ggtttcccga gcta                                                      74

<210> SEQ ID NO 32
<211> LENGTH: 73
<212> TYPE: DNA
<213> ORGANISM: Artificial
<220> FEATURE:
<223> OTHER INFORMATION: Cloned DNA Sequence

<400> SEQUENCE: 32
ggagccttcc tccggatcgt gatcattttc tccaatgatt atacgtttat ttactgtccg    60
gtttcccgag ctt                                                       73

<210> SEQ ID NO 33
<211> LENGTH: 71
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 33
agccttcctc cggaaattat tancgnttct attagacggn naangcgttt taggtccggt    60
ttcccgagct t                                                         71
```

```
<210> SEQ ID NO 34
<211> LENGTH: 73
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (42)..(43)
<223> OTHER INFORMATION: n is a, c, g, or t

<400> SEQUENCE: 34
ggagccttcc tccggacggg ataaataaaa tacatagtan gnnaacaggg tgttggtccg    60
gtttcccgag ctt                                                      73

<210> SEQ ID NO 35
<211> LENGTH: 73
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t

<400> SEQUENCE: 35
ggagccttcc tccggaaatc ggcatantnn acagtcatan ggnanntgtt ctcccatccg    60
gtttcccgag ctt                                                      73

<210> SEQ ID NO 36
<211> LENGTH: 73
<212> TYPE: DNA
<213> ORGANISM: Artificial
<220> FEATURE:
<223> OTHER INFORMATION: Cloned DNA Sequence

<400> SEQUENCE: 36
ggagccttcc tccggaccac tatttcgtat cggctttata tatatccgat tgcgcgtccg    60
gtttcccgag ctt                                                      73

<210> SEQ ID NO 37
<211> LENGTH: 88
<212> TYPE: DNA
<213> ORGANISM: Artificial
<220> FEATURE:
<223> OTHER INFORMATION: Cloned DNA Sequence

<400> SEQUENCE: 37
```

```
gggagacaag aataaacgct caatcctgta gagtttttat tcggttgatg ggcactgttt    60
tttattcgac aggaggctca caacaggc                                      88

<210> SEQ ID NO 38
<211> LENGTH: 88
<212> TYPE: DNA
<213> ORGANISM: Artificial
<220> FEATURE:
<223> OTHER INFORMATION: Cloned DNA Sequence

<400> SEQUENCE: 38
gggagacaag aataaacgct caatcctgta gagtttttat tcggttgatg ggcactgttt    60
tttattcgac aggaggctca caacaggc                                      88

<210> SEQ ID NO 39
<211> LENGTH: 88
<212> TYPE: DNA
<213> ORGANISM: Artificial
<220> FEATURE:
<223> OTHER INFORMATION: Cloned DNA Sequence

<400> SEQUENCE: 39
gggagacaag aataaacgct caatcctgta gagttcttat tcggttgatg ggcactgttt    60
tttattcgac aggaggctca caacaggc                                      88

<210> SEQ ID NO 40
<211> LENGTH: 88
<212> TYPE: DNA
<213> ORGANISM: Artificial
<220> FEATURE:
<223> OTHER INFORMATION: Cloned DNA Sequence

<400> SEQUENCE: 40
gggagacaag aataaacgct caatcctgta gagtttttat tcggttgatg ggcactgttt    60
tttattcgac aggaggctca caacaggc                                      88

<210> SEQ ID NO 41
<211> LENGTH: 89
<212> TYPE: DNA
<213> ORGANISM: Artificial
<220> FEATURE:
<223> OTHER INFORMATION: Cloned DNA Sequence

<400> SEQUENCE: 41
gggagacaag aataaacgct caatcctgta gagtttttat tcggttgatg ggcactgttt    60
ttttattcga caggaggctc acaacaggc                                     89

<210> SEQ ID NO 42
<211> LENGTH: 88
<212> TYPE: DNA
<213> ORGANISM: Artificial
<220> FEATURE:
<223> OTHER INFORMATION: Cloned DNA Sequence

<400> SEQUENCE: 42
gggagacaag aataaacgct caagcctgtg gagtttttat tcggttgatg ggcactgttt    60
tttattcgac aggaggctca caacaggc                                      88

<210> SEQ ID NO 43
<211> LENGTH: 88
<212> TYPE: DNA
```

```
<213> ORGANISM: Artificial
<220> FEATURE:
<223> OTHER INFORMATION: Cloned DNA Sequence

<400> SEQUENCE: 43
gggagacaag aataaacgct caagcctgta gagttttat tcggttgatg ggcactgttt    60
tttattcgac aggaggctca caacaggc                                      88

<210> SEQ ID NO 44
<211> LENGTH: 88
<212> TYPE: DNA
<213> ORGANISM: Artificial
<220> FEATURE:
<223> OTHER INFORMATION: Cloned DNA Sequence

<400> SEQUENCE: 44
gggagacaag aataaacgct caatcctgta gagcttttat tcggttgatg agcactgttt    60
tttattcgac aggaggctca caacaggc                                      88

<210> SEQ ID NO 45
<211> LENGTH: 88
<212> TYPE: DNA
<213> ORGANISM: Artificial
<220> FEATURE:
<223> OTHER INFORMATION: Cloned DNA Sequence

<400> SEQUENCE: 45
gggagacaag aataaacgct caatcctgta gagcttttat tcggttgatg agcactgttt    60
tttattcgac aggaggctca caacaggc                                      88

<210> SEQ ID NO 46
<211> LENGTH: 88
<212> TYPE: DNA
<213> ORGANISM: Artificial
<220> FEATURE:
<223> OTHER INFORMATION: Cloned DNA Sequence

<400> SEQUENCE: 46
gggagacaag aataaacgct caagcctgta gagcttttat tcggttgatg ggcactgttt    60
tttattcgac aggaggctca caacaggc                                      88

<210> SEQ ID NO 47
<211> LENGTH: 88
<212> TYPE: DNA
<213> ORGANISM: Artificial
<220> FEATURE:
<223> OTHER INFORMATION: Cloned DNA Sequence

<400> SEQUENCE: 47
gggagacaag aataaacgct caatcctgta gagtttttta ttcggttgat gggcactgtt    60
ttttattcga caggaggctc acaacagg                                      88

<210> SEQ ID NO 48
<211> LENGTH: 89
<212> TYPE: DNA
<213> ORGANISM: Artificial
<220> FEATURE:
<223> OTHER INFORMATION: Cloned DNA Sequence

<400> SEQUENCE: 48
gggagacaag aataaacgct caatcctgta gagtttttta ttcggttgat gggcactgtt    60
ttttattcga caggaggctc acaacaggc                                     89
```

<210> SEQ ID NO 49
<211> LENGTH: 88
<212> TYPE: DNA
<213> ORGANISM: Artificial
<220> FEATURE:
<223> OTHER INFORMATION: Cloned DNA Sequence

<400> SEQUENCE: 49
gggagacaag aataaacgct caagcctgta gagtttttat tcggttgatg ggcgctgttt    60
tttattcgac aggaggctca caacaggc                                       88

<210> SEQ ID NO 50
<211> LENGTH: 86
<212> TYPE: DNA
<213> ORGANISM: Artificial
<220> FEATURE:
<223> OTHER INFORMATION: Cloned DNA Sequence

<400> SEQUENCE: 50
gggagacaag aataaacgct caatagggtg accgacaata atgggagtca aactgttgtg    60
tgttcgacag gaggctcaca acaggc                                         86

<210> SEQ ID NO 51
<211> LENGTH: 86
<212> TYPE: DNA
<213> ORGANISM: Artificial
<220> FEATURE:
<223> OTHER INFORMATION: Cloned DNA Sequence

<400> SEQUENCE: 51
gggagacaag aataaacgct caatagggtg accgacaata atgggagtca aactgttgtg    60
tgttcgacag gaggctcaca acaggc                                         86

<210> SEQ ID NO 52
<211> LENGTH: 86
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (24)..(24)
<223> OTHER INFORMATION: n is a, c, g, or t

<400> SEQUENCE: 52
gggagacaag aataaacgct caanagggtg accgacaata atgggagtca aactgttgtg    60
tgttcgacag gaggctcaca acaggc                                         86

<210> SEQ ID NO 53
<211> LENGTH: 86
<212> TYPE: DNA
<213> ORGANISM: Artificial
<220> FEATURE:
<223> OTHER INFORMATION: Cloned DNA Sequence

<400> SEQUENCE: 53
gggagacaag aataaacgct caattgggtg accgacaatt atgggagtca gcttgttgag    60
agttcgacag gaggctcaca acaggc                                         86

<210> SEQ ID NO 54
<211> LENGTH: 86
<212> TYPE: DNA

<213> ORGANISM: Artificial
<220> FEATURE:
<223> OTHER INFORMATION: Cloned DNA Sequence

<400> SEQUENCE: 54

```
gggagacaag aataaacgct caattgggtg accgacaatt atgggagtca gcttgttgag    60
agttcgacag gaggctcaca acaggc                                         86
```

<210> SEQ ID NO 55
<211> LENGTH: 86
<212> TYPE: DNA
<213> ORGANISM: Artificial
<220> FEATURE:
<223> OTHER INFORMATION: Cloned DNA Sequence

<400> SEQUENCE: 55

```
gggagacaag aataaacgct caattgggtg accgacaatt atgggagtca gcttgttgag    60
agttcgacag gaggctcaca acaggc                                         86
```

<210> SEQ ID NO 56
<211> LENGTH: 86
<212> TYPE: DNA
<213> ORGANISM: Artificial
<220> FEATURE:
<223> OTHER INFORMATION: Cloned DNA Sequence

<400> SEQUENCE: 56

```
gggagacaag aataaacgct caattgggtg accgacaatt atgggagtca gcttgttgag    60
agttcgacag gaggctcaca acaggc                                         86
```

<210> SEQ ID NO 57
<211> LENGTH: 86
<212> TYPE: DNA
<213> ORGANISM: Artificial
<220> FEATURE:
<223> OTHER INFORMATION: Cloned DNA Sequence

<400> SEQUENCE: 57

```
gggagacaag aataaacgct caattgggtg accgacaatt atgggagtca gcttgttgag    60
agttcgacag gaggctcaca acaggc                                         86
```

<210> SEQ ID NO 58
<211> LENGTH: 87
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t

<400> SEQUENCE: 58

```
gggagacaag aataaacgct caatagggtg accgacaatn atgggagtca nncngttgat    60
gtgttcgaca ggaggctcac aacaggc                                        87
```

```
<210> SEQ ID NO 59
<211> LENGTH: 87
<212> TYPE: DNA
<213> ORGANISM: Artificial
<220> FEATURE:
<223> OTHER INFORMATION: Cloned DNA Sequence

<400> SEQUENCE: 59
gggagacaag aataaacgct caatgttgaa gtgtttagta agtgaagccg ctgttttagt    60
ttgttcgaca ggaggctcac aacaggc                                       87

<210> SEQ ID NO 60
<211> LENGTH: 85
<212> TYPE: DNA
<213> ORGANISM: Artificial
<220> FEATURE:
<223> OTHER INFORMATION: Cloned DNA Sequence

<400> SEQUENCE: 60
gggagacaag aataaacgct caataggtg accgacaaga tgggagtcca attgttgtga    60
gttcgacagg aggctcacaa caggc                                         85

<210> SEQ ID NO 61
<211> LENGTH: 87
<212> TYPE: DNA
<213> ORGANISM: Artificial
<220> FEATURE:
<223> OTHER INFORMATION: Cloned DNA Sequence

<400> SEQUENCE: 61
gggagacaag aataaacgct caaacagtgt agctcgtcga ttgctagggt gtccgacaga    60
acattcgaca ggaggctcac acaggca                                       87

<210> SEQ ID NO 62
<211> LENGTH: 87
<212> TYPE: DNA
<213> ORGANISM: Artificial
<220> FEATURE:
<223> OTHER INFORMATION: Cloned DNA Sequence

<400> SEQUENCE: 62
gggagacaag aataaacgct caagtgagtc ttccatcgat tttcttgggt gtccgacaga    60
gcattcgaca ggaggctcac aacaggc                                       87

<210> SEQ ID NO 63
<211> LENGTH: 87
<212> TYPE: DNA
<213> ORGANISM: Artificial
<220> FEATURE:
<223> OTHER INFORMATION: Cloned DNA Sequence

<400> SEQUENCE: 63
gggagacaag aataaacgct caaagagccg tgatcgttat cgaatgggtg tccgacgatt    60
cgtttcgaca ggaggctcac aacaggc                                       87

<210> SEQ ID NO 64
<211> LENGTH: 60
<212> TYPE: DNA
<213> ORGANISM: Artificial
<220> FEATURE:
<223> OTHER INFORMATION: Cloned DNA Sequence

<400> SEQUENCE: 64
```

```
gggagacaag aataaacgct caacataatg tgaagcttcg acaggaggct cacaacaggc    60
```

<210> SEQ ID NO 65
<211> LENGTH: 60
<212> TYPE: DNA
<213> ORGANISM: Artificial
<220> FEATURE:
<223> OTHER INFORMATION: Cloned DNA Sequence

<400> SEQUENCE: 65

```
gggagacaag aataaacgct caacataatg tgaagcttcg acaggaggct cacaacaggc    60
```

<210> SEQ ID NO 66
<211> LENGTH: 60
<212> TYPE: DNA
<213> ORGANISM: Artificial
<220> FEATURE:
<223> OTHER INFORMATION: Cloned DNA Sequence

<400> SEQUENCE: 66

```
gggagacaag aataaacgct caacataatg tgaagcttcg acaggaggct cacaacaggc    60
```

<210> SEQ ID NO 67
<211> LENGTH: 60
<212> TYPE: DNA
<213> ORGANISM: Artificial
<220> FEATURE:
<223> OTHER INFORMATION: Cloned DNA Sequence

<400> SEQUENCE: 67

```
gggagacaag aataaacgct caacataatg tgaagcttcg acaggaggct cacaacaggc    60
```

<210> SEQ ID NO 68
<211> LENGTH: 86
<212> TYPE: DNA
<213> ORGANISM: Artificial
<220> FEATURE:
<223> OTHER INFORMATION: Cloned DNA Sequence

<400> SEQUENCE: 68

```
gggagacaag aataaacgct caatggggtg accgacaatt atgggagtca gcttgttgag    60
agttcgacag gaggctcaca acaggc                                        86
```

<210> SEQ ID NO 69
<211> LENGTH: 86
<212> TYPE: DNA
<213> ORGANISM: Artificial
<220> FEATURE:
<223> OTHER INFORMATION: Cloned DNA Sequence

<400> SEQUENCE: 69

```
gggagacaag aataaacgct caattgggtg accgacaatt atgggagtca gcttgttgag    60
agttcgacag gaggctcaca acaggc                                        86
```

<210> SEQ ID NO 70
<211> LENGTH: 86
<212> TYPE: DNA
<213> ORGANISM: Artificial
<220> FEATURE:
<223> OTHER INFORMATION: Cloned DNA Sequence

<400> SEQUENCE: 70

```
gggagacaag aataaacgct caattgggtg accgacaatt atgggagtca gcttgttgag    60
agttcgacag gaggctcaca acaggc                                        86
```

<210> SEQ ID NO 71
<211> LENGTH: 86
<212> TYPE: DNA
<213> ORGANISM: Artificial
<220> FEATURE:
<223> OTHER INFORMATION: Cloned DNA Sequence

<400> SEQUENCE: 71
aggagacaag aataaacgct caattgggtg accgacaatt atgggagtca gcttgttgag    60
agttcgacag gaggctcaca acaggc    86

<210> SEQ ID NO 72
<211> LENGTH: 86
<212> TYPE: DNA
<213> ORGANISM: Artificial
<220> FEATURE:
<223> OTHER INFORMATION: Cloned DNA Sequence

<400> SEQUENCE: 72
gggagacaag aataaacgct caattgggtg accgacaatt atgggagtca gcttgttgag    60
agttcgacag gaggctcaca acaggc    86

<210> SEQ ID NO 73
<211> LENGTH: 86
<212> TYPE: DNA
<213> ORGANISM: Artificial
<220> FEATURE:
<223> OTHER INFORMATION: Cloned DNA Sequence

<400> SEQUENCE: 73
gggagacaag aataaacgct caattgggtg accgacaatt atgggagtca gcttgttgag    60
agttcgacag gaggctcaca acaggc    86

<210> SEQ ID NO 74
<211> LENGTH: 86
<212> TYPE: DNA
<213> ORGANISM: Artificial
<220> FEATURE:
<223> OTHER INFORMATION: Cloned DNA Sequence

<400> SEQUENCE: 74
gggagacaag aataaacgct caattgggtg accgacaatt atgggagtca gcttgttgag    60
agttcgacag gaggctcaca acaggc    86

<210> SEQ ID NO 75
<211> LENGTH: 86
<212> TYPE: DNA
<213> ORGANISM: Artificial
<220> FEATURE:
<223> OTHER INFORMATION: Cloned DNA Sequence

<400> SEQUENCE: 75
gggagacaag aataaacgct caattgggtg accgacaatt atgggagtca gcttgttgag    60
agttcgacag gaggctcaca acaggc    86

<210> SEQ ID NO 76
<211> LENGTH: 86
<212> TYPE: DNA
<213> ORGANISM: Artificial
<220> FEATURE:
<223> OTHER INFORMATION: Cloned DNA Sequence

<400> SEQUENCE: 76
gggagacaag aataaacgct caattgggtg accgacaatt atgggagtca gcttgttgag    60
agttcgacag gaggctcaca acaggc    86

<210> SEQ ID NO 77
<211> LENGTH: 86
<212> TYPE: DNA
<213> ORGANISM: Artificial
<220> FEATURE:
<223> OTHER INFORMATION: Cloned DNA Sequence

<400> SEQUENCE: 77
gggagacaag aataaacgct caattgggtg accgacaatt atgggagtca gcttgttgag    60
agttcgacag gaggctcaca acaggc    86

<210> SEQ ID NO 78
<211> LENGTH: 86
<212> TYPE: DNA
<213> ORGANISM: Artificial
<220> FEATURE:
<223> OTHER INFORMATION: Cloned DNA Sequence

<400> SEQUENCE: 78
gggagacaag aataaacgct caattgggtg accgacaatt atgggagtca gcttgttgag    60
agttcgacag gaggctcaca acaggc    86

<210> SEQ ID NO 79
<211> LENGTH: 86
<212> TYPE: DNA
<213> ORGANISM: Artificial
<220> FEATURE:
<223> OTHER INFORMATION: Cloned DNA Sequence

<400> SEQUENCE: 79
gggagacaag aataaacgct caattgggtg accgacaatt atgggagtca gcttgttgag    60
agttcgacag gaggctcaca acaggc    86

<210> SEQ ID NO 80
<211> LENGTH: 86
<212> TYPE: DNA
<213> ORGANISM: Artificial
<220> FEATURE:
<223> OTHER INFORMATION: Cloned DNA Sequence

<400> SEQUENCE: 80
gggagacaag aataaacgct caattgggtg accgacaatt atgggagtca gcttgttgag    60
agttcgacag gaggctcaca acaggc    86

<210> SEQ ID NO 81
<211> LENGTH: 86
<212> TYPE: DNA
<213> ORGANISM: Artificial
<220> FEATURE:
<223> OTHER INFORMATION: Cloned DNA Sequence

<400> SEQUENCE: 81
gggagacaag aataaacgct caattgggtg accgacaatt atgggagtca gcttgttgag    60
agttcgacag gaggctcaca acaggc    86

<210> SEQ ID NO 82
<211> LENGTH: 86

```
<212> TYPE: DNA
<213> ORGANISM: Artificial
<220> FEATURE:
<223> OTHER INFORMATION: Cloned DNA Sequence

<400> SEQUENCE: 82
gggagacaag aataaacgct caattgggtg accgacaatt atgggagtca gcttgttgag      60
agttcgacag gaggctcaca acaggc                                          86

<210> SEQ ID NO 83
<211> LENGTH: 86
<212> TYPE: DNA
<213> ORGANISM: Artificial
<220> FEATURE:
<223> OTHER INFORMATION: Cloned DNA Sequence

<400> SEQUENCE: 83
gggagacaag aataaacgct caatagggtg accgacaata atgggagtca gactgttgtg      60
tgttcgacag gaggctcaca acaggc                                          86

<210> SEQ ID NO 84
<211> LENGTH: 86
<212> TYPE: DNA
<213> ORGANISM: Artificial
<220> FEATURE:
<223> OTHER INFORMATION: Cloned DNA Sequence

<400> SEQUENCE: 84
gggagacaag aataaacgct caatagggtg accgacaata atgggagtca gactgttgtg      60
tgttcgacag gaggctcaca acaggc                                          86

<210> SEQ ID NO 85
<211> LENGTH: 86
<212> TYPE: DNA
<213> ORGANISM: Artificial
<220> FEATURE:
<223> OTHER INFORMATION: Cloned DNA Sequence

<400> SEQUENCE: 85
gggagacaag aataaacgct caatagggtg accgacaata atgggagtca gactgttgtg      60
tgttcgacag gaggctcaca acaggc                                          86

<210> SEQ ID NO 86
<211> LENGTH: 86
<212> TYPE: DNA
<213> ORGANISM: Artificial
<220> FEATURE:
<223> OTHER INFORMATION: Cloned DNA Sequence

<400> SEQUENCE: 86
gggagacaag aataaacgct caatagggtg accgacaata atgggagtca gactgttgtg      60
tgttcgacag gaggctcaca acaggc                                          86

<210> SEQ ID NO 87
<211> LENGTH: 87
<212> TYPE: DNA
<213> ORGANISM: Artificial
<220> FEATURE:
<223> OTHER INFORMATION: Cloned DNA Sequence

<400> SEQUENCE: 87
gggagacaag aataaacgct caaattgggt gaccgacaat tatgggagtc agcttgttga      60
```
gagttcgaca ggaggctcac aacaggc    87

<210> SEQ ID NO 88
<211> LENGTH: 87
<212> TYPE: DNA
<213> ORGANISM: Artificial
<220> FEATURE:
<223> OTHER INFORMATION: Cloned DNA Sequence

<400> SEQUENCE: 88
gggagacaag aataaacgct caataggggt gaccgacaat aatgggagtc aaactgttgt    60
gtgttcgaca ggaggctcac aacaggc    87

<210> SEQ ID NO 89
<211> LENGTH: 86
<212> TYPE: DNA
<213> ORGANISM: Artificial
<220> FEATURE:
<223> OTHER INFORMATION: Cloned DNA Sequence

<400> SEQUENCE: 89
gggagacaag aataaacgct caataggtg accgacaata atgggagtca aactgttgtg    60
tgttcgacag gaggctcaca acaggc    86

<210> SEQ ID NO 90
<211> LENGTH: 86
<212> TYPE: DNA
<213> ORGANISM: Artificial
<220> FEATURE:
<223> OTHER INFORMATION: Cloned DNA Sequence

<400> SEQUENCE: 90
gggagacaag aataaacgct caataggtg accgacaata atgggagtca aactgttgtg    60
tgttcgacag gaggctcaca acaggc    86

<210> SEQ ID NO 91
<211> LENGTH: 86
<212> TYPE: DNA
<213> ORGANISM: Artificial
<220> FEATURE:
<223> OTHER INFORMATION: Cloned DNA Sequence

<400> SEQUENCE: 91
gggagacaag aataaacgct caataggtg accgacaata atgggagtca aactgttgtg    60
tgttcgacag gaggctcaca acaggc    86

<210> SEQ ID NO 92
<211> LENGTH: 86
<212> TYPE: DNA
<213> ORGANISM: Artificial
<220> FEATURE:
<223> OTHER INFORMATION: Cloned DNA Sequence

<400> SEQUENCE: 92
gggagacaag aataaacgct caatggggtg accgacaata atgggagtca aactgttgtg    60
tgttcgacag gaggctcaca acaggc    86

<210> SEQ ID NO 93
<211> LENGTH: 86
<212> TYPE: DNA
<213> ORGANISM: Artificial
<220> FEATURE:
<223> OTHER INFORMATION: Cloned DNA Sequence

<400> SEQUENCE: 93
gggagacaag aataaacgct caatggggtg accgacaata atgggagtca aactgttgtg      60
tgttcgacag gaggctcaca acaggc      86

<210> SEQ ID NO 94
<211> LENGTH: 86
<212> TYPE: DNA
<213> ORGANISM: Artificial
<220> FEATURE:
<223> OTHER INFORMATION: Cloned DNA Sequence

<400> SEQUENCE: 94
gggagacaag aataaacgct caatggggtg accgacaata atgggagtca aactgttgtg      60
tgttcgacag gaggctcaca acaggc      86

<210> SEQ ID NO 95
<211> LENGTH: 86
<212> TYPE: DNA
<213> ORGANISM: Artificial
<220> FEATURE:
<223> OTHER INFORMATION: Cloned DNA Sequence

<400> SEQUENCE: 95
gggagacaag aataaacgct caattgggtg actgacaatt atgggagtca gcttgttgag      60
agttcgacag gaggctcaca acaggc      86

<210> SEQ ID NO 96
<211> LENGTH: 86
<212> TYPE: DNA
<213> ORGANISM: Artificial
<220> FEATURE:
<223> OTHER INFORMATION: Cloned DNA Sequence

<400> SEQUENCE: 96
gggagacaag aataaacgct caatagggtg accgacaata atgggagtca agctgttgtg      60
tgttcgacag gaggctcaca acaggc      86

<210> SEQ ID NO 97
<211> LENGTH: 86
<212> TYPE: DNA
<213> ORGANISM: Artificial
<220> FEATURE:
<223> OTHER INFORMATION: Cloned DNA Sequence

<400> SEQUENCE: 97
gggagacaag aataaacgct caatagggtg accgacaata atgggagtca agctgttgtg      60
tgttcgacag gaggctcaca acaggc      86

<210> SEQ ID NO 98
<211> LENGTH: 86
<212> TYPE: DNA
<213> ORGANISM: Artificial
<220> FEATURE:
<223> OTHER INFORMATION: Cloned DNA Sequence

<400> SEQUENCE: 98
gggagacaag aataaacgct caattgggtg accgacaatt atgggagtca gctcgttgag      60
agttcgacag gaggctcaca acaggc      86

<210> SEQ ID NO 99

```
<211> LENGTH: 86
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (24)..(24)
<223> OTHER INFORMATION: n is a, c, g, or t

<400> SEQUENCE: 99
gggagacaag aataaacgct caanagggtg accgacaata atgggagtca aactgttgtg    60
tgttcgacag gaggctcaca acaggc                                         86

<210> SEQ ID NO 100
<211> LENGTH: 86
<212> TYPE: DNA
<213> ORGANISM: Artificial
<220> FEATURE:
<223> OTHER INFORMATION: Cloned DNA Sequence

<400> SEQUENCE: 100
gggagacaag aataaacgct caattgggtg accgacattt atgggagtca gcttgttgag    60
agttcgacag gaggctcaca acaggc                                         86

<210> SEQ ID NO 101
<211> LENGTH: 85
<212> TYPE: DNA
<213> ORGANISM: Artificial
<220> FEATURE:
<223> OTHER INFORMATION: Cloned DNA Sequence

<400> SEQUENCE: 101
gggagacaag aataaacgct caattgggtg accgacaatt atgggagtca gcttgtgaga    60
gttcgacagg aggctcacaa caggc                                          85

<210> SEQ ID NO 102
<211> LENGTH: 86
<212> TYPE: DNA
<213> ORGANISM: Artificial
<220> FEATURE:
<223> OTHER INFORMATION: Cloned DNA Sequence

<400> SEQUENCE: 102
gggagacaag aataaacgct caattgggtg gccgacaatt atgggagtca gcttgttgag    60
agttcgacag gaggctcaca acaggc                                         86

<210> SEQ ID NO 103
<211> LENGTH: 86
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (61)..(61)
<223> OTHER INFORMATION: n is a, c, g, or t

<400> SEQUENCE: 103
gggagacaag aataaacgct caatggggtg accgacaata atgggagtca aactgttgtg    60
ngttcgacag gaggctcaca acaggc                                         86

<210> SEQ ID NO 104
<211> LENGTH: 87
```

```
<212> TYPE: DNA
<213> ORGANISM: Artificial
<220> FEATURE:
<223> OTHER INFORMATION: Cloned DNA Sequence

<400> SEQUENCE: 104
gggagacaag aataaacgct caattgggtg accgacaatt atgggagtca aacttgttga      60
gagttcgaca ggaggctcac aacaggc                                         87

<210> SEQ ID NO 105
<211> LENGTH: 86
<212> TYPE: DNA
<213> ORGANISM: Artificial
<220> FEATURE:
<223> OTHER INFORMATION: Cloned DNA Sequence

<400> SEQUENCE: 105
gggagacaag aataaacgct caatggggtg accgacaata atgggagtcc aattgttgtg      60
tgttcgacag gaggctcaca acaggc                                          86

<210> SEQ ID NO 106
<211> LENGTH: 86
<212> TYPE: DNA
<213> ORGANISM: Artificial
<220> FEATURE:
<223> OTHER INFORMATION: Cloned DNA Sequence

<400> SEQUENCE: 106
gggagacaag aataaacgct caatggggtg accgacaata atgggagtcc aattgttgtg      60
tgttcgacag gaggctcaca acaggc                                          86

<210> SEQ ID NO 107
<211> LENGTH: 86
<212> TYPE: DNA
<213> ORGANISM: Artificial
<220> FEATURE:
<223> OTHER INFORMATION: Cloned DNA Sequence

<400> SEQUENCE: 107
gggagacaag aataaacgct caatggggtg accgacaata atgggagtcc aattgttgtg      60
tgttcgacag gaggctcaca acaggc                                          86

<210> SEQ ID NO 108
<211> LENGTH: 86
<212> TYPE: DNA
<213> ORGANISM: Artificial
<220> FEATURE:
<223> OTHER INFORMATION: Cloned DNA Sequence

<400> SEQUENCE: 108
gggagacaag aataaacgct caataggtg accgataata atgggagtca aactgttgtg       60
tgttcgacag gaggctcaca acaggc                                          86

<210> SEQ ID NO 109
<211> LENGTH: 86
<212> TYPE: DNA
<213> ORGANISM: Artificial
<220> FEATURE:
<223> OTHER INFORMATION: Cloned DNA Sequence

<400> SEQUENCE: 109
agggagacaa gataaacgct caataggtg accgacaata gtgggagtca aactgttgtg       60
```
tgttcgacag gaggctcaca acaggc                                              86

<210> SEQ ID NO 110
<211> LENGTH: 86
<212> TYPE: DNA
<213> ORGANISM: Artificial
<220> FEATURE:
<223> OTHER INFORMATION: Cloned DNA Sequence

<400> SEQUENCE: 110
gggagacaag aataaacgct caacggggtg accgacaata atgggagtcc aattgttgtg        60
tgttcgacag gaggctcaca acaggc                                              86

<210> SEQ ID NO 111
<211> LENGTH: 86
<212> TYPE: DNA
<213> ORGANISM: Artificial
<220> FEATURE:
<223> OTHER INFORMATION: Cloned DNA Sequence

<400> SEQUENCE: 111
gggagacaag aataaacgct caatggggtg accgacaatt atgggagtct aaatgttgtg        60
atttcgacag gaggctcaca acaggc                                              86

<210> SEQ ID NO 112
<211> LENGTH: 86
<212> TYPE: DNA
<213> ORGANISM: Artificial
<220> FEATURE:
<223> OTHER INFORMATION: Cloned DNA Sequence

<400> SEQUENCE: 112
gggagacaag aataaacgct caattgggtg accgacattt atgggagtcc aatcgttgtg        60
aattcgacag gaggctcaca acaggc                                              86

<210> SEQ ID NO 113
<211> LENGTH: 88
<212> TYPE: DNA
<213> ORGANISM: Artificial
<220> FEATURE:
<223> OTHER INFORMATION: Cloned DNA Sequence

<400> SEQUENCE: 113
gggagacaag aataaacgct caatcctgta gagtttttat tcggttgatg ggcactgttt        60
tttattcgac aggaggctca caacaggc                                            88

<210> SEQ ID NO 114
<211> LENGTH: 88
<212> TYPE: DNA
<213> ORGANISM: Artificial
<220> FEATURE:
<223> OTHER INFORMATION: Cloned DNA Sequence

<400> SEQUENCE: 114
gggagacaag aataaacgct caatcctgta gagtttttat tcggttgatg ggcactgttt        60
tttattcgac aggaggctca caacaggc                                            88

<210> SEQ ID NO 115
<211> LENGTH: 89
<212> TYPE: DNA
<213> ORGANISM: Artificial
<220> FEATURE:
<223> OTHER INFORMATION: Cloned DNA Sequence

```
<400> SEQUENCE: 115
gggagacaag aataaacgct caatcctgta gagtttttta ttcggttgat gggcactgtt    60 tttattcga caggaggctc acacaggca                                       89

<210> SEQ ID NO 116
<211> LENGTH: 86
<212> TYPE: DNA
<213> ORGANISM: Artificial
<220> FEATURE:
<223> OTHER INFORMATION: Cloned DNA Sequence

<400> SEQUENCE: 116
gggagacaag aataaacgct caattgggtg accgacaatt atgggagtca gcttgttgag    60
agttcgacag ggggctcaca acaggc                                         86

<210> SEQ ID NO 117
<211> LENGTH: 86
<212> TYPE: DNA
<213> ORGANISM: Artificial
<220> FEATURE:
<223> OTHER INFORMATION: Cloned DNA Sequence

<400> SEQUENCE: 117
gggagacaag aataaacgct caattgggtg accgacaatt atgggagtca gcttgttgag    60
agttcgacag gaggctcaca acaggc                                         86

<210> SEQ ID NO 118
<211> LENGTH: 86
<212> TYPE: DNA
<213> ORGANISM: Artificial
<220> FEATURE:
<223> OTHER INFORMATION: Cloned DNA Sequence

<400> SEQUENCE: 118
gggagacaag aataaacgct caattgggtg accgacaatt atgggagtca gcttgttgag    60
agttcgacag gaggctcaca acaggc                                         86

<210> SEQ ID NO 119
<211> LENGTH: 86
<212> TYPE: DNA
<213> ORGANISM: Artificial
<220> FEATURE:
<223> OTHER INFORMATION: Cloned DNA Sequence

<400> SEQUENCE: 119
gggagacaag aataaacgct caattgggtg accgacaatt atgggagtca gcttgttgag    60
agttcgacag gaggctcaca acaggc                                         86

<210> SEQ ID NO 120
<211> LENGTH: 86
<212> TYPE: DNA
<213> ORGANISM: Artificial
<220> FEATURE:
<223> OTHER INFORMATION: Cloned DNA Sequence

<400> SEQUENCE: 120
gggagacaag aataaacgct caattgggtg accgacaatt atgggagtca gcttgttgag    60
agttcgacag gaggctcaca acaggc                                         86

<210> SEQ ID NO 121
```

```
<211> LENGTH: 86
<212> TYPE: DNA
<213> ORGANISM: Artificial
<220> FEATURE:
<223> OTHER INFORMATION: Cloned DNA Sequence

<400> SEQUENCE: 121
gggagacaag aataaacgct caattgggtg accgacaatt atgggagtca gcttgttgag      60
agttcgacag gaggctcaca acaggc                                          86

<210> SEQ ID NO 122
<211> LENGTH: 86
<212> TYPE: DNA
<213> ORGANISM: Artificial
<220> FEATURE:
<223> OTHER INFORMATION: Cloned DNA Sequence

<400> SEQUENCE: 122
gggagacaag aataaacgct caattgggtg accgacaatt atgggagtca gcttgttgag      60
agttcgacag gaggctcaca acaggc                                          86

<210> SEQ ID NO 123
<211> LENGTH: 86
<212> TYPE: DNA
<213> ORGANISM: Artificial
<220> FEATURE:
<223> OTHER INFORMATION: Cloned DNA Sequence

<400> SEQUENCE: 123
gggagacaag aataaacgct caattgggtg accgacaatt atgggagtca gcttgttgag      60
agttcgacag gaggctcaca acaggc                                          86

<210> SEQ ID NO 124
<211> LENGTH: 85
<212> TYPE: DNA
<213> ORGANISM: Artificial
<220> FEATURE:
<223> OTHER INFORMATION: Cloned DNA Sequence

<400> SEQUENCE: 124
gggagacaag aataacgctc aattgggtga ccgacaatta tgggagtcag cttgttgaga      60
gttcgacagg aggctcacaa caggc                                           85

<210> SEQ ID NO 125
<211> LENGTH: 86
<212> TYPE: DNA
<213> ORGANISM: Artificial
<220> FEATURE:
<223> OTHER INFORMATION: Cloned DNA Sequence

<400> SEQUENCE: 125
gggagacaag aataaacgct caattgggtg accgacaatt atgggagtca gcttgttgag      60
agttcgacag gaggctcaca acaggc                                          86

<210> SEQ ID NO 126
<211> LENGTH: 86
<212> TYPE: DNA
<213> ORGANISM: Artificial
<220> FEATURE:
<223> OTHER INFORMATION: Cloned DNA Sequence

<400> SEQUENCE: 126
gggagacaag aataaacgct caattgggtg accgacaatt atgggagtca gcttgttgag      60
```
agttcgacag gaggctcaca acaggc                                          86

```
<210> SEQ ID NO 127
<211> LENGTH: 86
<212> TYPE: DNA
<213> ORGANISM: Artificial
<220> FEATURE:
<223> OTHER INFORMATION: Cloned DNA Sequence

<400> SEQUENCE: 127
```
gggagacaag aataaacgct caattgggtg accgacaatt atgggagtca gcttgttgag      60
agttcgacag gaggctcaca acaggc                                          86

```
<210> SEQ ID NO 128
<211> LENGTH: 86
<212> TYPE: DNA
<213> ORGANISM: Artificial
<220> FEATURE:
<223> OTHER INFORMATION: Cloned DNA Sequence

<400> SEQUENCE: 128
```
gggagacaag aataaacgct caattgggtg accgacaatt atgggagtca gcttgttgag      60
agttcgacag gaggctcaca acaggc                                          86

```
<210> SEQ ID NO 129
<211> LENGTH: 86
<212> TYPE: DNA
<213> ORGANISM: Artificial
<220> FEATURE:
<223> OTHER INFORMATION: Cloned DNA Sequence

<400> SEQUENCE: 129
```
gggagacaag aataaacgct caattgggtg accgacaatt atgggagtca gcttgttgag      60
agttcgacag gaggctcaca acaggc                                          86

```
<210> SEQ ID NO 130
<211> LENGTH: 86
<212> TYPE: DNA
<213> ORGANISM: Artificial
<220> FEATURE:
<223> OTHER INFORMATION: Cloned DNA Sequence

<400> SEQUENCE: 130
```
gggagacaag aataaacgct caattgggtg accgacaatt atgggagtca gcttgttgag      60
agttcgacag gaggctcaca acaggc                                          86

```
<210> SEQ ID NO 131
<211> LENGTH: 86
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (52)..(52)
<223> OTHER INFORMATION: n is a, c, g, or t

<400> SEQUENCE: 131
```
gggagacaag aataaacgct caattgggtg accgacaatt atgggagtca gnttgttgag      60
agttcgacag gaggctcaca acaggc                                          86

```
<210> SEQ ID NO 132
```

```
<211> LENGTH: 86
<212> TYPE: DNA
<213> ORGANISM: Artificial
<220> FEATURE:
<223> OTHER INFORMATION: Cloned DNA Sequence

<400> SEQUENCE: 132
gggagacaag aataaacgct caattgggtg gccgacaatt atgggagtca gcttgttgag    60
agttcgacag gaggctcaca acaggc                                        86

<210> SEQ ID NO 133
<211> LENGTH: 86
<212> TYPE: DNA
<213> ORGANISM: Artificial
<220> FEATURE:
<223> OTHER INFORMATION: Cloned DNA Sequence

<400> SEQUENCE: 133
gggagacaag aataaacgct caatagggtg accgacaata atgggagtca gactgttgtg    60
tgttcgacag gaggctcaca acaggc                                        86

<210> SEQ ID NO 134
<211> LENGTH: 86
<212> TYPE: DNA
<213> ORGANISM: Artificial
<220> FEATURE:
<223> OTHER INFORMATION: Cloned DNA Sequence

<400> SEQUENCE: 134
gggagacaag aataaacgct caattgggtg accgaccatt atgggagtca gcttgttgag    60
agttcgacag gaggctcaca acaggc                                        86

<210> SEQ ID NO 135
<211> LENGTH: 86
<212> TYPE: DNA
<213> ORGANISM: Artificial
<220> FEATURE:
<223> OTHER INFORMATION: Cloned DNA Sequence

<400> SEQUENCE: 135
gggagacaag aataaacgct caatagggtg accgacaata atgggagtca gactgttgtg    60
tgttcgacag gaggctcaca acaggc                                        86

<210> SEQ ID NO 136
<211> LENGTH: 86
<212> TYPE: DNA
<213> ORGANISM: Artificial
<220> FEATURE:
<223> OTHER INFORMATION: Cloned DNA Sequence

<400> SEQUENCE: 136
gggagacaag aataaacgct caatagggtg accgacaata atgggagtca gactgttgtg    60
tgttcgacag gaggctcaca acaggc                                        86

<210> SEQ ID NO 137
<211> LENGTH: 86
<212> TYPE: DNA
<213> ORGANISM: Artificial
<220> FEATURE:
<223> OTHER INFORMATION: Cloned DNA Sequence

<400> SEQUENCE: 137
gggagacaag aataaacgct caaatgggtg accgacaatt atgggagtca gcttgttgag    60
```
agttcgacag gaggctcaca acaggc 86

<210> SEQ ID NO 138
<211> LENGTH: 86
<212> TYPE: DNA
<213> ORGANISM: Artificial
<220> FEATURE:
<223> OTHER INFORMATION: Cloned DNA Sequence

<400> SEQUENCE: 138
gggagacaag aataaacgct caatcgggtg accgacagtt atgggagtca gcttgttgag 60
agttcgacag gaggctcaca acaggc 86

<210> SEQ ID NO 139
<211> LENGTH: 86
<212> TYPE: DNA
<213> ORGANISM: Artificial
<220> FEATURE:
<223> OTHER INFORMATION: Cloned DNA Sequence

<400> SEQUENCE: 139
gggagacaag aataaacgct caatcgggtg accgacagtt atgggagtca gcttgttgag 60
agttcgacag gaggctcaca acaggc 86

<210> SEQ ID NO 140
<211> LENGTH: 86
<212> TYPE: DNA
<213> ORGANISM: Artificial
<220> FEATURE:
<223> OTHER INFORMATION: Cloned DNA Sequence

<400> SEQUENCE: 140
gggagacaag aataaacgct caatagggtg accgacaata atgggagtca aactgttgtg 60
tgttcgacag gaggctcaca acaggc 86

<210> SEQ ID NO 141
<211> LENGTH: 86
<212> TYPE: DNA
<213> ORGANISM: Artificial
<220> FEATURE:
<223> OTHER INFORMATION: Cloned DNA Sequence

<400> SEQUENCE: 141
gggagacaag aataaacgct caatagggtg accgacaata atgggagtca aactgttgtg 60
tgttcgacag gaggctcaca acaggc 86

<210> SEQ ID NO 142
<211> LENGTH: 86
<212> TYPE: DNA
<213> ORGANISM: Artificial
<220> FEATURE:
<223> OTHER INFORMATION: Cloned DNA Sequence

<400> SEQUENCE: 142
gggagacaag aataaacgct caatagggtg accgacaata atgggagtca agctgttgtg 60
tgttcgacag gaggctcaca acaggc 86

<210> SEQ ID NO 143
<211> LENGTH: 86
<212> TYPE: DNA
<213> ORGANISM: Artificial
<220> FEATURE:

<223> OTHER INFORMATION: Cloned DNA Sequence

<400> SEQUENCE: 143
gggagacaag aataaacgct caataggggtg accgacaata atgggagtca agctgttgtg    60
tgttcgacag gaggctcaca acaggc    86

<210> SEQ ID NO 144
<211> LENGTH: 86
<212> TYPE: DNA
<213> ORGANISM: Artificial
<220> FEATURE:
<223> OTHER INFORMATION: Cloned DNA Sequence

<400> SEQUENCE: 144
gggagacaag aataaacgct caataggggtg accgacaata atgggagtca agctgttgtg    60
tgttcgacag gaggctcaca acaggc    86

<210> SEQ ID NO 145
<211> LENGTH: 86
<212> TYPE: DNA
<213> ORGANISM: Artificial
<220> FEATURE:
<223> OTHER INFORMATION: Cloned DNA Sequence

<400> SEQUENCE: 145
gggagacaag aataaacgct caataggggtg accgacaata atgggagtca agctgttgtg    60
tgttcgacag gaggctcaca acaggc    86

<210> SEQ ID NO 146
<211> LENGTH: 86
<212> TYPE: DNA
<213> ORGANISM: Artificial
<220> FEATURE:
<223> OTHER INFORMATION: Cloned DNA Sequence

<400> SEQUENCE: 146
gggagacaag aataaacgct caataggggtg accgacaata atgggagtca agctgttgtg    60
tgttcgacag gaggctcaca acaggc    86

<210> SEQ ID NO 147
<211> LENGTH: 86
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (27)..(27)
<223> OTHER INFORMATION: n is a, c, g, or t

<400> SEQUENCE: 147
gggagacaag aataaacgct caattgngtg accgacaata atgggagtca gactgttgtg    60
tgttcgacag gaggctcaca acaggc    86

<210> SEQ ID NO 148
<211> LENGTH: 86
<212> TYPE: DNA
<213> ORGANISM: Artificial
<220> FEATURE:
<223> OTHER INFORMATION: Cloned DNA Sequence

<400> SEQUENCE: 148
gggagacaag aataaacgct caatggggtg accgacaata atgggagtcc aattgttgtg    60

```
tgttcgacag gaggctcaca acaggc                                            86

<210> SEQ ID NO 149
<211> LENGTH: 86
<212> TYPE: DNA
<213> ORGANISM: Artificial
<220> FEATURE:
<223> OTHER INFORMATION: Cloned DNA Sequence

<400> SEQUENCE: 149
gggagacaag aataaacgct caatggggtg accgacaata atgggagtcc aattgttgtg       60
tgttcgacag gaggctcaca acaggc                                            86

<210> SEQ ID NO 150
<211> LENGTH: 86
<212> TYPE: DNA
<213> ORGANISM: Artificial
<220> FEATURE:
<223> OTHER INFORMATION: Cloned DNA Sequence

<400> SEQUENCE: 150
gggagacaag aataaacgct caatagggtg accgacaata gtgggagtca aactgttgtg       60
tgttcgacag gaggctcaca acaggc                                            86

<210> SEQ ID NO 151
<211> LENGTH: 86
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 151
gggagacaag aataaacgct caattgggtg accgacnata atgggagtcc nattgttgtg       60
tgttcgacag gaggctcaca acaggc                                            86

<210> SEQ ID NO 152
<211> LENGTH: 86
<212> TYPE: DNA
<213> ORGANISM: Artificial
<220> FEATURE:
<223> OTHER INFORMATION: Cloned DNA Sequence

<400> SEQUENCE: 152
gggagacaag aataaacgct caatggggtg accgacaatt atgggagtct aaatgttgtg       60
atttcgacag ggggctcaca acaggc                                            86

<210> SEQ ID NO 153
<211> LENGTH: 86
<212> TYPE: DNA
<213> ORGANISM: Artificial
<220> FEATURE:
<223> OTHER INFORMATION: Cloned DNA Sequence

<400> SEQUENCE: 153
gggagacaag aataaacgct caatagggtg accgacaaca atgggagtta agctgttgtg       60
```

```
tgttcgacag gaggctcaca acaggc                                           86

<210> SEQ ID NO 154
<211> LENGTH: 86
<212> TYPE: DNA
<213> ORGANISM: Artificial
<220> FEATURE:
<223> OTHER INFORMATION: Cloned DNA Sequence

<400> SEQUENCE: 154
gggagacaag aataaacgct caatggggtg accgacaatt atgggagtct aaacgttgtg     60
atttcgacag gaggctcaca acaggc                                           86

<210> SEQ ID NO 155
<211> LENGTH: 85
<212> TYPE: DNA
<213> ORGANISM: Artificial
<220> FEATURE:
<223> OTHER INFORMATION: Cloned DNA Sequence

<400> SEQUENCE: 155
gggagacaag aataaacgct caatggggtg accgacaatt atgggagtct aaatgttgtg     60
attcgacagg aggctcacaa caggc                                            85

<210> SEQ ID NO 156
<211> LENGTH: 87
<212> TYPE: DNA
<213> ORGANISM: Artificial
<220> FEATURE:
<223> OTHER INFORMATION: Cloned DNA Sequence

<400> SEQUENCE: 156
gggagacaag aataaacgct caaacctgtc gttgatatgt ttagttctta gttgtgtgtg     60
gctttcgaca ggaggctcac aacaggc                                          87

<210> SEQ ID NO 157
<211> LENGTH: 88
<212> TYPE: DNA
<213> ORGANISM: Artificial
<220> FEATURE:
<223> OTHER INFORMATION: Cloned DNA Sequence

<400> SEQUENCE: 157
gggagacaag aataaacgct caatcctgta gagtttttat tcggttgatg ggcactgttt     60
tttattcgac aggaggctca caacaggc                                         88

<210> SEQ ID NO 158
<211> LENGTH: 88
<212> TYPE: DNA
<213> ORGANISM: Artificial
<220> FEATURE:
<223> OTHER INFORMATION: Cloned DNA Sequence

<400> SEQUENCE: 158
gggagacaag aataaacgct caatcctgta gagtttttat tcggttgatg ggcactgttt     60
tttattcgac aggaggctca caacaggc                                         88

<210> SEQ ID NO 159
<211> LENGTH: 88
<212> TYPE: DNA
<213> ORGANISM: Artificial
<220> FEATURE:
<223> OTHER INFORMATION: Cloned DNA Sequence
```

```
<400> SEQUENCE: 159
gggagacaag aataaacgct caatcctgta gagtttttat tcggttgatg ggcactgttt    60
tttattcgac aggaggctca caacaggc                                      88

<210> SEQ ID NO 160
<211> LENGTH: 89
<212> TYPE: DNA
<213> ORGANISM: Artificial
<220> FEATURE:
<223> OTHER INFORMATION: Cloned DNA Sequence

<400> SEQUENCE: 160
gggagacaag aataaacgct caatcctgta gagtctttta ttcggttgat gggcactgtt    60
ttttattcga caggaggctc acaacaggc                                     89

<210> SEQ ID NO 161
<211> LENGTH: 87
<212> TYPE: DNA
<213> ORGANISM: Artificial
<220> FEATURE:
<223> OTHER INFORMATION: Cloned DNA Sequence

<400> SEQUENCE: 161
gggagacaag aataaacgct caacctgtca tgggacgttt aactactgct ggggtacctg    60
taattcgaca ggaggctcac aacaggc                                       87

<210> SEQ ID NO 162
<211> LENGTH: 73
<212> TYPE: DNA
<213> ORGANISM: Artificial
<220> FEATURE:
<223> OTHER INFORMATION: Cloned DNA Sequence

<400> SEQUENCE: 162
ggagccttcc tccggaagtc aagagtaaca cagggaatgc gtactcttct tatttgtccg    60
gtttcccgag ctt                                                      73

<210> SEQ ID NO 163
<211> LENGTH: 73
<212> TYPE: DNA
<213> ORGANISM: Artificial
<220> FEATURE:
<223> OTHER INFORMATION: Cloned DNA Sequence

<400> SEQUENCE: 163
ggagccttcc tccggaagtc aagagtaaca cagggaatgc gtactcttct tatttgtccg    60
gtttcccgag ctt                                                      73

<210> SEQ ID NO 164
<211> LENGTH: 73
<212> TYPE: DNA
<213> ORGANISM: Artificial
<220> FEATURE:
<223> OTHER INFORMATION: Cloned DNA Sequence

<400> SEQUENCE: 164
ggagccttcc tccggaagtc aagagtaaca cagggaatgc gtactcttct tatttgtccg    60
gtttcccgag ctt                                                      73

<210> SEQ ID NO 165
```

```
<211> LENGTH: 73
<212> TYPE: DNA
<213> ORGANISM: Artificial
<220> FEATURE:
<223> OTHER INFORMATION: Cloned DNA Sequence

<400> SEQUENCE: 165
ggagccttcc tccggaagtc aagagtaaca cagggaatgc gtactcttct tatttgtccg      60
gtttcccgag ctt                                                        73

<210> SEQ ID NO 166
<211> LENGTH: 73
<212> TYPE: DNA
<213> ORGANISM: Artificial
<220> FEATURE:
<223> OTHER INFORMATION: Cloned DNA Sequence

<400> SEQUENCE: 166
ggagccttcc tccggaagtc aagagtaaca cagggaatgc gtactcttct tatttgtccg      60
gtttcccgag ctt                                                        73

<210> SEQ ID NO 167
<211> LENGTH: 73
<212> TYPE: DNA
<213> ORGANISM: Artificial
<220> FEATURE:
<223> OTHER INFORMATION: Cloned DNA Sequence

<400> SEQUENCE: 167
ggagccttcc tccggaagtc aagagtaaca cagggaatgc gtactcttct tatttgtccg      60
gtttcccgag ctt                                                        73

<210> SEQ ID NO 168
<211> LENGTH: 73
<212> TYPE: DNA
<213> ORGANISM: Artificial
<220> FEATURE:
<223> OTHER INFORMATION: Cloned DNA Sequence

<400> SEQUENCE: 168
ggagccttcc tccggaagtc aagagtaaca cagggaatgc gtactcttct tatttgtccg      60
gtttcccgag ctt                                                        73

<210> SEQ ID NO 169
<211> LENGTH: 73
<212> TYPE: DNA
<213> ORGANISM: Artificial
<220> FEATURE:
<223> OTHER INFORMATION: Cloned DNA Sequence

<400> SEQUENCE: 169
ggagccttcc tccggaagtc aagagtaaca cagggaatgc gtactcttct tatttgtccg      60
gtttcccgag ctt                                                        73

<210> SEQ ID NO 170
<211> LENGTH: 73
<212> TYPE: DNA
<213> ORGANISM: Artificial
<220> FEATURE:
<223> OTHER INFORMATION: Cloned DNA Sequence

<400> SEQUENCE: 170
ggagccttcc tccggaagtc aagagtaaca cagggaatgc gtactcttct tatttgtccg      60
```

```
gtttcccgag ctt                                                          73

<210> SEQ ID NO 171
<211> LENGTH: 73
<212> TYPE: DNA
<213> ORGANISM: Artificial
<220> FEATURE:
<223> OTHER INFORMATION: Cloned DNA Sequence

<400> SEQUENCE: 171
ggagccttcc tccggaagtc aagagtaaca cagggaatgc gtactcttct tatttgtccg       60
gtttcccgag ctt                                                          73

<210> SEQ ID NO 172
<211> LENGTH: 73
<212> TYPE: DNA
<213> ORGANISM: Artificial
<220> FEATURE:
<223> OTHER INFORMATION: Cloned DNA Sequence

<400> SEQUENCE: 172
ggagccttcc tccggaagtc aagagtaaca cagggaatgc gtactcttct tatttgtccg       60
gtttcccgag ctt                                                          73

<210> SEQ ID NO 173
<211> LENGTH: 73
<212> TYPE: DNA
<213> ORGANISM: Artificial
<220> FEATURE:
<223> OTHER INFORMATION: Cloned DNA Sequence

<400> SEQUENCE: 173
ggagccttcc tccggaagtc aagagtaaca cagggaatgc gtactcttct tatttgtccg       60
gtttcccgag ctt                                                          73

<210> SEQ ID NO 174
<211> LENGTH: 73
<212> TYPE: DNA
<213> ORGANISM: Artificial
<220> FEATURE:
<223> OTHER INFORMATION: Cloned DNA Sequence

<400> SEQUENCE: 174
ggagccttcc tccggaagtc aagagtaaca cagggaatgc gtactcttct tatttgtccg       60
gtttcccgag ctt                                                          73

<210> SEQ ID NO 175
<211> LENGTH: 73
<212> TYPE: DNA
<213> ORGANISM: Artificial
<220> FEATURE:
<223> OTHER INFORMATION: Cloned DNA Sequence

<400> SEQUENCE: 175
ggagccttcc tccggaagtc aagagtagca cagggaatgc gtactcttct tatttgtccg       60
gtttcccgag ctt                                                          73

<210> SEQ ID NO 176
<211> LENGTH: 73
<212> TYPE: DNA
<213> ORGANISM: Artificial
<220> FEATURE:
```

<223> OTHER INFORMATION: Cloned DNA Sequence

<400> SEQUENCE: 176
ggagccttcc tccggaagtc aagagtagca cagggaatgc gtactcttct tatttgtccg    60
gtttcccgag ctt    73

<210> SEQ ID NO 177
<211> LENGTH: 73
<212> TYPE: DNA
<213> ORGANISM: Artificial
<220> FEATURE:
<223> OTHER INFORMATION: Cloned DNA Sequence

<400> SEQUENCE: 177
ggagccttcc tccggaagtc aagagtagca cagggaatgc gtactcttct tatttgtccg    60
gtttcccgag ctt    73

<210> SEQ ID NO 178
<211> LENGTH: 73
<212> TYPE: DNA
<213> ORGANISM: Artificial
<220> FEATURE:
<223> OTHER INFORMATION: Cloned DNA Sequence

<400> SEQUENCE: 178
ggagccttcc tccggaagtc aagagtagca cagggaatgc gtactcttct tatttgtccg    60
gtttcccgag ctt    73

<210> SEQ ID NO 179
<211> LENGTH: 73
<212> TYPE: DNA
<213> ORGANISM: Artificial
<220> FEATURE:
<223> OTHER INFORMATION: Cloned DNA Sequence

<400> SEQUENCE: 179
ggagccttcc tccggaagtc aagagtagca cagggaatgc gtactcttct tatttgtccg    60
gtttcccgag ctt    73

<210> SEQ ID NO 180
<211> LENGTH: 73
<212> TYPE: DNA
<213> ORGANISM: Artificial
<220> FEATURE:
<223> OTHER INFORMATION: Cloned DNA Sequence

<400> SEQUENCE: 180
ggagccttcc tccggaagtc aagagtagca cagggaatgc gtactcttct tatttgtccg    60
gtttcccgag ctt    73

<210> SEQ ID NO 181
<211> LENGTH: 73
<212> TYPE: DNA
<213> ORGANISM: Artificial
<220> FEATURE:
<223> OTHER INFORMATION: Cloned DNA Sequence

<400> SEQUENCE: 181
ggagccttcc tccggaagtc aagagtagca cagggaatgc gtactcttct tatttgtccg    60
gtttcccgag ctt    73

```
<210> SEQ ID NO 182
<211> LENGTH: 73
<212> TYPE: DNA
<213> ORGANISM: Artificial
<220> FEATURE:
<223> OTHER INFORMATION: Cloned DNA Sequence

<400> SEQUENCE: 182
ggagccttcc tccggaagtc aagagtagca cagggaatgc gtactcttct tatttgtccg    60
gtttcccgag ctt                                                       73

<210> SEQ ID NO 183
<211> LENGTH: 73
<212> TYPE: DNA
<213> ORGANISM: Artificial
<220> FEATURE:
<223> OTHER INFORMATION: Cloned DNA Sequence

<400> SEQUENCE: 183
ggagccttcc tccggaagtc aagagtagca cagggaatgc gtactcttct tatttgtccg    60
gtttcccgag ctt                                                       73

<210> SEQ ID NO 184
<211> LENGTH: 73
<212> TYPE: DNA
<213> ORGANISM: Artificial
<220> FEATURE:
<223> OTHER INFORMATION: Cloned DNA Sequence

<400> SEQUENCE: 184
ggagccttcc tccggaagtc aagagtagca cagggaatgc gtactcttct tatttgtccg    60
gtttcccgag ctt                                                       73

<210> SEQ ID NO 185
<211> LENGTH: 73
<212> TYPE: DNA
<213> ORGANISM: Artificial
<220> FEATURE:
<223> OTHER INFORMATION: Cloned DNA Sequence

<400> SEQUENCE: 185
ggagccttcc tccggaagcc aagagtaaca cagggaatgc gtactcttct tatttgtccg    60
gtttcccgag ctt                                                       73

<210> SEQ ID NO 186
<211> LENGTH: 73
<212> TYPE: DNA
<213> ORGANISM: Artificial
<220> FEATURE:
<223> OTHER INFORMATION: Cloned DNA Sequence

<400> SEQUENCE: 186
ggagccttcc tccggaggtc aagagtagca cagggaatgc gtactcttct tatttgtccg    60
gtttcccgag ctt                                                       73

<210> SEQ ID NO 187
<211> LENGTH: 73
<212> TYPE: DNA
<213> ORGANISM: Artificial
<220> FEATURE:
<223> OTHER INFORMATION: Cloned DNA Sequence

<400> SEQUENCE: 187
```

```
ggagccttcc tccggaagtc aagagtaaca cagggaacgc gtactcttct tatttgtccg    60
gtttcccgag ctt                                                       73

<210> SEQ ID NO 188
<211> LENGTH: 73
<212> TYPE: DNA
<213> ORGANISM: Artificial
<220> FEATURE:
<223> OTHER INFORMATION: Cloned DNA Sequence

<400> SEQUENCE: 188
ggagccttcc tccggaagtc aagagtaaca cagggaacgc gtactcttct tatttgtccg    60
gtttcccgag ctt                                                       73

<210> SEQ ID NO 189
<211> LENGTH: 73
<212> TYPE: DNA
<213> ORGANISM: Artificial
<220> FEATURE:
<223> OTHER INFORMATION: Cloned DNA Sequence

<400> SEQUENCE: 189
ggagccttcc tccggaagtc aagagtagca cagggaatgc gctctcttct tatttgtccg    60
gtttcccgag ctt                                                       73

<210> SEQ ID NO 190
<211> LENGTH: 73
<212> TYPE: DNA
<213> ORGANISM: Artificial
<220> FEATURE:
<223> OTHER INFORMATION: Cloned DNA Sequence

<400> SEQUENCE: 190
ggagccttcc tccggattcc ggacctgttt acgcaatatg aattatttgc gtcgcctccg    60
gtttcccgag ctt                                                       73

<210> SEQ ID NO 191
<211> LENGTH: 73
<212> TYPE: DNA
<213> ORGANISM: Artificial
<220> FEATURE:
<223> OTHER INFORMATION: Cloned DNA Sequence

<400> SEQUENCE: 191
ggagccttcc tccggattcc ggacctgttt acgcaatatg aattatttgc gtcgcctccg    60
gtttcccgag ctt                                                       73

<210> SEQ ID NO 192
<211> LENGTH: 73
<212> TYPE: DNA
<213> ORGANISM: Artificial
<220> FEATURE:
<223> OTHER INFORMATION: Cloned DNA Sequence

<400> SEQUENCE: 192
ggagccttcc tccggattcc ggacctgttt acgcaatatg aattatttgc gtcgcctccg    60
gtttcccgag ctt                                                       73

<210> SEQ ID NO 193
<211> LENGTH: 73
<212> TYPE: DNA
<213> ORGANISM: Artificial
```

```
<220> FEATURE:
<223> OTHER INFORMATION: Cloned DNA Sequence

<400> SEQUENCE: 193
ggagccttcc tccggattcc ggacctgttt acgcaatatg aattatttgc gtcgcctccg    60
gtttcccgag ctt                                                       73

<210> SEQ ID NO 194
<211> LENGTH: 73
<212> TYPE: DNA
<213> ORGANISM: Artificial
<220> FEATURE:
<223> OTHER INFORMATION: Cloned DNA Sequence

<400> SEQUENCE: 194
ggagccttcc tccggattcc ggacctgttt acgcaatatg aattatttgc gtcgcctccg    60
gtttcccgag ctt                                                       73

<210> SEQ ID NO 195
<211> LENGTH: 46
<212> TYPE: DNA
<213> ORGANISM: Artificial
<220> FEATURE:
<223> OTHER INFORMATION: Cloned DNA Sequence

<400> SEQUENCE: 195
ggagccttcc tccggattcc ggacctgttt acgcaatatg aattat                   46

<210> SEQ ID NO 196
<211> LENGTH: 73
<212> TYPE: DNA
<213> ORGANISM: Artificial
<220> FEATURE:
<223> OTHER INFORMATION: Cloned DNA Sequence

<400> SEQUENCE: 196
ggagccttcc tccggattcc ggacctgttt acgcaatatg aattatttgc gtcgcctccg    60
gtttcccgag ctt                                                       73

<210> SEQ ID NO 197
<211> LENGTH: 73
<212> TYPE: DNA
<213> ORGANISM: Artificial
<220> FEATURE:
<223> OTHER INFORMATION: Cloned DNA Sequence

<400> SEQUENCE: 197
ggagccttcc tccggattcc ggacctgttt acgcaatatg aattatttgc gtcgcctccg    60
gtttcccgag ctt                                                       73

<210> SEQ ID NO 198
<211> LENGTH: 73
<212> TYPE: DNA
<213> ORGANISM: Artificial
<220> FEATURE:
<223> OTHER INFORMATION: Cloned DNA Sequence

<400> SEQUENCE: 198
ggagccttcc tccggattcc ggacctgttt acgcaatatg aattatttgc gtcgcctccg    60
gtttcccgag ctt                                                       73

<210> SEQ ID NO 199
```

```
<211> LENGTH: 73
<212> TYPE: DNA
<213> ORGANISM: Artificial
<220> FEATURE:
<223> OTHER INFORMATION: Cloned DNA Sequence

<400> SEQUENCE: 199
ggagccttcc tccggattcc ggacctgttt acgcaatatg aattatttgc gtcgcctccg    60
gtttcccgag ctt                                                      73

<210> SEQ ID NO 200
<211> LENGTH: 73
<212> TYPE: DNA
<213> ORGANISM: Artificial
<220> FEATURE:
<223> OTHER INFORMATION: Cloned DNA Sequence

<400> SEQUENCE: 200
ggagccttcc tccggactcc ggacctgttt acgcaatatg aattatttgc gtcgcctccg    60
gtttcccgag ctt                                                      73

<210> SEQ ID NO 201
<211> LENGTH: 73
<212> TYPE: DNA
<213> ORGANISM: Artificial
<220> FEATURE:
<223> OTHER INFORMATION: Cloned DNA Sequence

<400> SEQUENCE: 201
ggagccttcc tccggattcc ggacctgttt acgcgatatg aattatttgc gtcgcctccg    60
gtttcccgag ctt                                                      73

<210> SEQ ID NO 202
<211> LENGTH: 73
<212> TYPE: DNA
<213> ORGANISM: Artificial
<220> FEATURE:
<223> OTHER INFORMATION: Cloned DNA Sequence

<400> SEQUENCE: 202
ggagccttcc tccggattcc ggacctgttt acgcgatatg aattatttgc gtcgcctccg    60
gtttcccgag ctt                                                      73

<210> SEQ ID NO 203
<211> LENGTH: 73
<212> TYPE: DNA
<213> ORGANISM: Artificial
<220> FEATURE:
<223> OTHER INFORMATION: Cloned DNA Sequence

<400> SEQUENCE: 203
ggagccttcc tccggagtag tctacgaatg attggaaacg cattcgtact tttgtgtccg    60
gtttcccgag ctt                                                      73

<210> SEQ ID NO 204
<211> LENGTH: 73
<212> TYPE: DNA
<213> ORGANISM: Artificial
<220> FEATURE:
<223> OTHER INFORMATION: Cloned DNA Sequence

<400> SEQUENCE: 204
ggagccttcc tccggagtag tctacgactg attggaaacg cattcgtact tatgtgtccg    60
```
gtttcccgag ctt                                                        73

<210> SEQ ID NO 205
<211> LENGTH: 73
<212> TYPE: DNA
<213> ORGANISM: Artificial
<220> FEATURE:
<223> OTHER INFORMATION: Cloned DNA Sequence

<400> SEQUENCE: 205
ggagccttcc tccggagtag tctacgactg attggaaacg cattcgtact tttgtgtccg      60
gtttcccgag ctt                                                        73

<210> SEQ ID NO 206
<211> LENGTH: 73
<212> TYPE: DNA
<213> ORGANISM: Artificial
<220> FEATURE:
<223> OTHER INFORMATION: Cloned DNA Sequence

<400> SEQUENCE: 206
ggagccttcc tccggagtag tctacgactg attggaaacg cattcgtact tttgtgtccg      60
gtttcccgag ctt                                                        73

<210> SEQ ID NO 207
<211> LENGTH: 73
<212> TYPE: DNA
<213> ORGANISM: Artificial
<220> FEATURE:
<223> OTHER INFORMATION: Cloned DNA Sequence

<400> SEQUENCE: 207
ggagccttcc tccggagtag tctacgactg attggaaacg cattcgtact tttgtgtccg      60
gtttcccgag ctt                                                        73

<210> SEQ ID NO 208
<211> LENGTH: 73
<212> TYPE: DNA
<213> ORGANISM: Artificial
<220> FEATURE:
<223> OTHER INFORMATION: Cloned DNA Sequence

<400> SEQUENCE: 208
ggagccttcc tccggagtag tctacgactg attggaaacg cattcgtact tttgtgtccg      60
gtttcccgag ctt                                                        73

<210> SEQ ID NO 209
<211> LENGTH: 73
<212> TYPE: DNA
<213> ORGANISM: Artificial
<220> FEATURE:
<223> OTHER INFORMATION: Cloned DNA Sequence
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:

```
<221> NAME/KEY: misc_feature
<222> LOCATION: (54)..(54)
<223> OTHER INFORMATION: n is a, c, g, or t

<400> SEQUENCE: 209
ngagccttcc tccggattcc ggacctgttt acncaatatg aattatttnc gtcncctccg      60
gtttcccgag ctt                                                        73

<210> SEQ ID NO 210
<211> LENGTH: 74
<212> TYPE: DNA
<213> ORGANISM: Artificial
<220> FEATURE:
<223> OTHER INFORMATION: Cloned DNA Sequence

<400> SEQUENCE: 210
ggagccttcc tccggagtaa atacggatac gcgcaaattg aaatcgtagt gtgcatatcc      60
ggtttcccga gctt                                                       74

<210> SEQ ID NO 211
<211> LENGTH: 73
<212> TYPE: DNA
<213> ORGANISM: Artificial
<220> FEATURE:
<223> OTHER INFORMATION: Cloned DNA Sequence

<400> SEQUENCE: 211
ggagccttcc tccggataca atacttgggg cacaacaagt tattatcttt ccggggtccg      60
gtttcccgag ctt                                                        73

<210> SEQ ID NO 212
<211> LENGTH: 73
<212> TYPE: DNA
<213> ORGANISM: Artificial
<220> FEATURE:
<223> OTHER INFORMATION: Cloned DNA Sequence

<400> SEQUENCE: 212
ggagccttcc tccggatgcg aaagtatgat ggtctttact tttgaacatc ctgtggtccg      60
gtttcccgag cta                                                        73

<210> SEQ ID NO 213
<211> LENGTH: 76
<212> TYPE: DNA
<213> ORGANISM: Artificial
<220> FEATURE:
<223> OTHER INFORMATION: Cloned DNA Sequence

<400> SEQUENCE: 213
ggagccttcc tccggaaacc gttatcaaaa aaaacacgat ctgctctatc gcttgttcgt      60
ccggtttccc gagctt                                                     76

<210> SEQ ID NO 214
<211> LENGTH: 73
<212> TYPE: DNA
<213> ORGANISM: Artificial
<220> FEATURE:
<223> OTHER INFORMATION: Cloned DNA Sequence

<400> SEQUENCE: 214
ggagccttcc tccggaaacc catgttggca attcatttc acagtacttg ttggcgtccg       60
gtttcccgag ctt                                                        73
```

<210> SEQ ID NO 215
<211> LENGTH: 72
<212> TYPE: DNA
<213> ORGANISM: Artificial
<220> FEATURE:
<223> OTHER INFORMATION: Cloned DNA Sequence

<400> SEQUENCE: 215
ggagccttcc tccggaaacg gcaagtgtat atgtccggtc ttttagtaca cttggtccgg      60
tttcccgagc tt                                                         72

<210> SEQ ID NO 216
<211> LENGTH: 73
<212> TYPE: DNA
<213> ORGANISM: Artificial
<220> FEATURE:
<223> OTHER INFORMATION: Cloned DNA Sequence

<400> SEQUENCE: 216
ggagccttcc tccggatcag ccacagttaa aaatagcttg tttgtgctta tctgggtccg      60
gtttcccgag ctt                                                        73

<210> SEQ ID NO 217
<211> LENGTH: 73
<212> TYPE: DNA
<213> ORGANISM: Artificial
<220> FEATURE:
<223> OTHER INFORMATION: Cloned DNA Sequence

<400> SEQUENCE: 217
ggagccttcc tccggaaata cggtttgcta aaagcatctt ccatccattg agttggtccg      60
gtttcccgag ctt                                                        73

<210> SEQ ID NO 218
<211> LENGTH: 73
<212> TYPE: DNA
<213> ORGANISM: Artificial
<220> FEATURE:
<223> OTHER INFORMATION: Cloned DNA Sequence

<400> SEQUENCE: 218
ggagccttcc tccggaaata cggtttgcta aaagcatctt ccatccattg agatggtccg      60
gtttcccgag ctt                                                        73

<210> SEQ ID NO 219
<211> LENGTH: 75
<212> TYPE: DNA
<213> ORGANISM: Artificial
<220> FEATURE:
<223> OTHER INFORMATION: Cloned DNA Sequence

<400> SEQUENCE: 219
ggagccttcc tccggattgc cgtctagcaa atagtttttc cgaaactagt ccggagtgtc      60
cggtttcccg agctt                                                      75

<210> SEQ ID NO 220
<211> LENGTH: 75
<212> TYPE: DNA
<213> ORGANISM: Artificial
<220> FEATURE:
<223> OTHER INFORMATION: Cloned DNA Sequence -continued

```
<400> SEQUENCE: 220
ggagccttcc tccggaaacg cttatgcaat taagcatccg actcatttgt cttttgggtc    60
cggtttcccg agctt                                                    75

<210> SEQ ID NO 221
<211> LENGTH: 73
<212> TYPE: DNA
<213> ORGANISM: Artificial
<220> FEATURE:
<223> OTHER INFORMATION: Cloned DNA Sequence

<400> SEQUENCE: 221
ggagccttcc tccggaaatc cggtaaagat caccaatgtt tctagtgtgt tcgtggtccg    60
gtttcccgag ctt                                                      73

<210> SEQ ID NO 222
<211> LENGTH: 73
<212> TYPE: DNA
<213> ORGANISM: Artificial
<220> FEATURE:
<223> OTHER INFORMATION: Cloned DNA Sequence

<400> SEQUENCE: 222
ggagccttcc tccggaaact tgacacgact gcaatttgtg ttacgcagtc tgttggtccg    60
gtttcccgag ctt                                                      73

<210> SEQ ID NO 223
<211> LENGTH: 73
<212> TYPE: DNA
<213> ORGANISM: Artificial
<220> FEATURE:
<223> OTHER INFORMATION: Cloned DNA Sequence

<400> SEQUENCE: 223
ggagccttcc tccggaaatc gacatagtcc gctaattttt gctcgttagt cagctgtccg    60
gtttcccgag ctt                                                      73

<210> SEQ ID NO 224
<211> LENGTH: 72
<212> TYPE: DNA
<213> ORGANISM: Artificial
<220> FEATURE:
<223> OTHER INFORMATION: Cloned DNA Sequence

<400> SEQUENCE: 224
ggagccttcc tccggaaacc cgcatcatag gcgattggat agcaatccac ctacatccgg    60
tttcccgagc tt                                                       72

<210> SEQ ID NO 225
<211> LENGTH: 55
<212> TYPE: RNA
<213> ORGANISM: Artificial
<220> FEATURE:
<223> OTHER INFORMATION: Aptamer structure

<400> SEQUENCE: 225
gggauaaacg cucaaccgaa gcgcgacgac uagacgucaa uuuaucaacc uucga         55

<210> SEQ ID NO 226
<211> LENGTH: 82
<212> TYPE: RNA
<213> ORGANISM: Artificial
```

```
<220> FEATURE:
<223> OTHER INFORMATION: Isolated clone sequence

<400> SEQUENCE: 226
gggagacaag aauaaacgcu caaccgaagc gcgacgacua gacgucaauu uaucaaccuu    60
cgacaggagg cucacaacag gc                                            82

<210> SEQ ID NO 227
<211> LENGTH: 42
<212> TYPE: RNA
<213> ORGANISM: Artificial
<220> FEATURE:
<223> OTHER INFORMATION: Truncated isolated clone sequence

<400> SEQUENCE: 227
auaaacgcuc aaccgaagcg cgacgacuag acgucaauuu au                      42

<210> SEQ ID NO 228
<211> LENGTH: 16
<212> TYPE: RNA
<213> ORGANISM: Artificial
<220> FEATURE:
<223> OTHER INFORMATION: Chemically synthesized portion of diverse pool

<400> SEQUENCE: 228
ggacacauac ucuaca                                                   16

<210> SEQ ID NO 229
<211> LENGTH: 55
<212> TYPE: RNA
<213> ORGANISM: Artificial
<220> FEATURE:
<223> OTHER INFORMATION: Chemically synthesized portion of diverse pool

<400> SEQUENCE: 229
gggauaaacg cucaaccgaa gcgcgacgac uagacgucaa uuuaucaacc uucga        55

<210> SEQ ID NO 230
<211> LENGTH: 20
<212> TYPE: RNA
<213> ORGANISM: Artificial
<220> FEATURE:
<223> OTHER INFORMATION: Chemically synthesized portion of diverse pool

<400> SEQUENCE: 230
uuaacccagc acgccucgua                                               20

<210> SEQ ID NO 231
<211> LENGTH: 21
<212> TYPE: PRT
<213> ORGANISM: Artificial
<220> FEATURE:
<223> OTHER INFORMATION: Biotinylated sulfotyrosine-CCR5 peptide
<220> FEATURE:
<221> NAME/KEY: MOD_RES
<222> LOCATION: (9)..(9)
<223> OTHER INFORMATION: SULFATATION
<220> FEATURE:
<221> NAME/KEY: misc_feature
<222> LOCATION: (9)..(9)
<223> OTHER INFORMATION: Xaa is tyrosine
<220> FEATURE:
<221> NAME/KEY: MOD_RES
<222> LOCATION: (13)..(13)
<223> OTHER INFORMATION: SULFATATION
<220> FEATURE:
<221> NAME/KEY: misc_feature
<222> LOCATION: (13)..(13)
```

```
<223> OTHER INFORMATION: Xaa is tyrosine

<400> SEQUENCE: 231

Asp Tyr Gln Val Ser Ser Pro Ile Xaa Asp Ile Asn Xaa Tyr Thr Ser
1               5                   10                  15

Glu Gly Ala Gly Lys
            20
```